(12) United States Patent
Chang et al.

(10) Patent No.: US 9,267,949 B2
(45) Date of Patent: Feb. 23, 2016

(54) ALKYLAMINO BODIPY DYES AS SELECTIVE FLUORESCENT PROBES FOR PROTEINS AND MOUSE EMBRYONIC STEM CELLS

(75) Inventors: Young-Tae Chang, Singapore (SG); Marc Vendrell Escobar, Singapore (SG); Duanting Zhai, Singapore (SG); Nam-Young Kang, Singapore (SG); Yogeswari Chandran, Singapore (SG)

(73) Assignees: National University of Singapore, Singapore (SG); Agency for Science, Technology and Research, Singapore (SG)

( * ) Notice: Subject to any disclaimer, the term of this patent is extended or adjusted under 35 U.S.C. 154(b) by 0 days.

(21) Appl. No.: 14/126,340

(22) PCT Filed: Jun. 15, 2012

(86) PCT No.: PCT/SG2012/000215
§ 371 (c)(1),
(2), (4) Date: Dec. 13, 2013

(87) PCT Pub. No.: WO2012/173575
PCT Pub. Date: Dec. 20, 2012

(65) Prior Publication Data
US 2014/0121129 A1 May 1, 2014

Related U.S. Application Data

(60) Provisional application No. 61/497,145, filed on Jun. 15, 2011.

(51) Int. Cl.
*G01N 33/58* (2006.01)
*C07F 5/02* (2006.01)
*C09B 57/00* (2006.01)
*C09B 23/14* (2006.01)

(52) U.S. Cl.
CPC ............... *G01N 33/582* (2013.01); *C07F 5/02* (2013.01); *C09B 23/14* (2013.01); *C09B 57/00* (2013.01)

(58) Field of Classification Search
CPC ....................................................... C07F 5/022
See application file for complete search history.

(56) References Cited

U.S. PATENT DOCUMENTS

| | | | |
|---|---|---|---|
| 2010/0291547 A1 | 11/2010 | Chen et al. | |
| 2011/0054187 A1 | 3/2011 | Rurack et al. | |
| 2014/0359794 A1 | 12/2014 | Chang et al. | |

FOREIGN PATENT DOCUMENTS

| | | |
|---|---|---|
| CN | 101020787 A | 8/2007 |
| CN | 101565554 | 10/2009 |
| JP | 2002025636 A | 1/2002 |
| JP | 2008239615 A | 10/2008 |
| WO | WO 2012/173575 | 12/2012 |

OTHER PUBLICATIONS

Aijun, C., "Synthesis, spectral properties and photostability of novel boron-dipyrromethene dyes", *Journal of Photochemistry and Photobiology A: Chemistry*, 186(1):85-92 (2007).
Bozdemir O.A., et al., "Selective manipulation of ICT and PET processes in styryl-Bodipy derivatives: applications in molecular logic and fluorescence sensing of metal ions"., *Journal of American Chemical Society*, 132(23): 8029-8036 (2010).
Coskun, A. et al., "Ion Sensing Coupled to Resonance Energy Transfer: A Highly Selective and Sensitive Ratiometric Fluorescent Chemosensor for Ag(I) by a Modular Approach", *J. Am. Chem. Soc.*, 127, p. 10464-10465 (2005).
Das, R.K., et al., "Target Identification: A Challenging Step in Forward Chemical Genetics", IBC, 3(3):1-16 (2011).
Descalzo, A.B., et al., "Red/near-infrared boron-dipyrromethene dyes as strongly emitting fluorophores", *Annals of the New York Academy of Sciences*, pp. 164-171 (2008).
Dumont, Y., et al., "BODIPY-conjugated neuropeptide Y ligands: new fluorescent tools to tag Y1, Y2, Y4 and Y5 receptor subtypes", *British Journal of Pharmacology*, 146(8):1069-1081 (2005).
Gomez-Duran, C.F., et al., "8-PropargylaminoBODIPY: unprecedented blue-emitting pyrromethene dye. Synthesis, photophysics and laser properties", *Chem. Commun.*, 46:5103-5105 (2010).
Han., J., et al., 3- and 5-Functionalized BODIPYs via Liebeskind-Srogl reaction, *Org. Biomol. Chem*, 7: 34-36 (2009).
Hoogendoorn et al., "Synthesis of pH-Activatable Red Fluorescent BODIPY Dyes With Distinct Functionalities," Organic Letters, 13(20): 5656-5659 (Sep. 26, 2011), See Abstract, Compounds of Schemes 1 and Figure 2.
International Search Report for International Application No. PCT/SG2012/000483, "Bodipy Structure Fluorescence Probes for Diverse Biological Applications", Date of mailing: Feb. 8, 2013.
International Preliminary Report on Patentability for International Application No. PCT/SG2012/000483, "Bodipy Structure Fluorescence Probes for Diverse Biological Applications", Date of mailing: Jun. 24, 2014.
International Preliminary Report on Patentability for Int'l Application No. PCT/SG2012/00483, entitled: "Bodipy Structure Fluorescence Probes for Diverse Biological Applications," Date of Mailing: Jul. 3, 2014.
Johnson, I.D., et al., "Fluorescent Membrane Probes Incorporating Dipyrrometheneboron Difluoride Fluorophores", 198(2): 228-237 (1991).
Kang, N.Y., et al., "Diversity-driven chemical probe development for biomolecules: beyond hypothesis-driven approach", *Chem So. Rev.*, 40: 3613-3626 (2011).
Karolin, J., et al., "Fluorescence and Absorption Spectroscopic Properties of Dipyrrometheneboron Difluoride (BODIPY) Derivatives in Liquids, Lipid Membranes, and Proteins", *J. Am. Chem. Soc.*, 116: 7801-7806 (1994).

(Continued)

*Primary Examiner* — Brian McDowell
(74) *Attorney, Agent, or Firm* — Hamilton, Brook, Smith & Reynolds, P.C.

(57) ABSTRACT

The present invention discloses a series of alkylamino BODIPY dyes, methods for preparing a library of alkyl-amino BODIPY dyes via solid-phase synthesis, and the use of the alkyl-amino BODIPY dyes as fluorescent sensors for protein detection, cell imaging and cytometry applications, and staining of certain cell line.

11 Claims, 14 Drawing Sheets

(56) References Cited

OTHER PUBLICATIONS

Kim, Y.K., et al., "Control of Muscle Differentiation by a Mitochondria-Targeted Fluorophore", *J. Am. Chem. Soc.*, 132: 576-579 (2010).
Kollmannsberger M., et al., "Ultrafast Charge Transfer in Amino-Substituted Boron Dipyrromethene Dyes and Its Inhibition by Cation Complexation: A New Design Concept for Highly Sensitive Fluorescent Probes", *J. Phys. Chem. A.*, 102: 10211-10220 (1998).
Lager, E., et al., "Novel meso-Polyarylamine-BODIPY Hybrids: Synthesis and Study of Their Optical Properties", *J. Org. Chem.*, 74: 2053-2058 (2009).
Lavis, L. D., et al., "Bright Ideas for Chemical Biology", *ACS Chem. Biol.*, 3(3): 142-155 (2008).
Lee, et al., "BODIPY-diacrylate Imaging Probes for Targeted Proteins Inside Live Cells," *Chem. Commun.*, 47: 4508-4510 (Mar. 8, 2011), See Abstract, Scheme 1.
Lee, et al., "Synthesis of BODIPY Library and Its Application to the Development of Live Cell Glucagon Imaging Probe," *J. Am. Chem. Soc.*, 131(29): 10077-10082 (2009), See Abstract, Scheme 1.
Lee, H.Y., "BODIPY-functionalized gold nanoparticles as a selective fluoro-chromogenic chemosensor for imaging Cu2+ in living cells", *Analyst*, 135(8): 2022-2027 (2010).
Lee, J. S., et al., "Accelerating fluorescent sensor discovery: unbiased screening of a diversity-oriented BODIPY library", *Chem Commun.*, 47: 2339-2341 (2011).
Leen, V., et al., "Direct functionalization of BODIPY dyes by oxidative nucleophilic hydrogen substitution at the 3- or 3,5-positions", *Chem. Commun.*, 46: 4908-4910 (2010).
Leen, V., et al., "A versatile, modular synthesis of monofunctionalized BODIPY dyes", *W. Chem. Commun.*, 45: 4515-4517 (2009).
Li, Q., et al., "Styryl-based compounds as potential in vivo imaging agents for beta-amyloid plaques", *Chembiochem*, 8(14): 1679-87 (2007).
Li Z., et al., "First Synthesis of Free Cholesterol-BODIPY Conjugates", *J. Org. Chem.*, 71:1718-1721 (2006).
Louder, et al., "BODIPY Dyes and Their Derivatives: Synthesis and Spectroscopic Properties," Chem. Rev., 107: 4891-4932 (2007), See whole document.
Loudet, A., et al., "BODIPY Dyes and Their Derivatives: Syntheses and Spectroscopic Properties", *Chem. Rev.*, 107, pp. 4891-4932 (2007).
Lukowiak, B., et al., "Identification and Purification of Functional Human-cells by a New Specific Zinc-fluorescent Probe," *J. Histochem. Cytochem.*, 49: 519-528 (2001).
Mula, et al., "Dual BODIPY Fluorophores Linked by Polyethyleneglycol Spacers," Tetrahedron Letters, 50(46): 6383-6388 (2009), See Abstract, Compounds 1-18.
Nicolaou, K. C., et al., "A Mild Method for the Synthesis of 2-Ketopyrroles from Carboxylic Acids", *Tetrahedron Lett.*, 22: 4647-4650 (1981).
Ono, M., "Development of dual functional SPEC/fluorescent probes for imaging cerebral beta-amyloid plaques", *Bioorganic & Medicinal Chemistry Letters* 20(13): 3885-3888 (2010).
Peng X., et al., "A Selective Fluorescent Sensor for Imaging $Cd^{2+}$ in Living Cells", *J. Am. Chem. Soc.*, 129, 1500-1501 (2007).
Polazzi, E., "Microglia and Neuroprotection: from in vivo studies to therapeutic applications", *Prog. Neurobiol.*, 92(3): 293-315 (Nov. 2010) (Epub. Jul. 4, 2010).
Qin, W., et al., "Synthesis, spectroscopy, crystal structure, electrochemistry, and quantum chemical and molecular dynamics calculations of a 3-anilino difluoroboron dipyrromethene dye", *Journal of Physical Chemistry A.*, 113(2): 439-447 (2009).
Qin, W., et al., "Solvent-dependent photophysical properties of borondipyrromethene dyes in solution", *Chem. Phys. Lett.*, 420: 562-568 (2006).
Ramachary, D. B., et al., "Towards Organo-Click Chemistry: Development of Organocatalytic Multicomponent Reactions Through Combinations of Aldol, Wittig, Knoevenagel, Michael, Diels-Alder and Huisgen Cycloaddition Reactions", *Chemistry*, 10:5323-5331 (2004).
Rich, R. L., et al., "Survey of the year 2007 commercial optical biosensor literature", *J. Mol. Recognit.*, 21: 355-400 (2008).
Rohand, T. et al., "Functionalisation of Fluorescent BODIPY dyes by nucleophilic substitution", *Chem. Commun*. 42: 266-268 (2006).
Rohand, T. et al., "Palladium-Catalyzed Coupling Reactions for the Functionalization of BODIPY Dyes with Fluorescence Spanning the Visible Spectrum", *J. Org. Chem*, p. 4658-4663 (2006).
Rurack, K., et al., "Molecular-Switching in the Near Infrared (NIR) with a Functionalized Boron-Dipyrromethene Dye", *Angew. Chem. Int. Ed.*, 40(2): 385-387 (2001).
Soumyaditya M., et al., "Dual Bodipy fluorophores linked by polyethyleneglycol spacers", *Tetrahedron Letters*, 50(46): 6383-6388 (2009).
Sunahara, H., et al., "Design and Synthesis of a Library of BODIPY-Based Environmental Polarity Sensors Utilizing Photoinduced Electron-Transfer-Controlled Fluorescence ON/OFF Switching", *J. Am. Chem. Soc.*, 129: 5597-5604 (2007).
Takahashi, N., et al., "Two-photon excitation imaging of pancreatic islets with various fluorescent probes", *Diabetes*, Suppl 1, S25-S28 (2002).
Ulrich, G. et al., "The Chemistry of Fluorescent BODIPY Dyes: Versatility Unsurpassed," Angew. Chem. Int. Ed., 47: 1184-1201 (2008), See whole document.
Ulrich, G. et al., "The Chemistry of Fluorescent Bodipy Dyes: Versatility Unsurpassed", *Chem. Int. Ed.*, 46: 2-20 (2007).
Vendrell, M., et al., "Diversity-oriented fluorescence library approaches for probe discovery and development", *Current Opinion in Chemical Biology*, 14(3): 383-389 (2010).
Wang, Yan-Wei, et al., "A colorimetric and fluorescent turn-on chemosensor for $Al^{3+}$ and its applicant in bioimaging", *Tetrahedron Letters*, 50(45): 6169-6172 (2009).
Written Opinion for International Application No. PCT/SG2012/000483, entitled: "Bodipy Structure Fluorescence Probes for Diverse Biological Applications," Date of Mailing: Feb. 8, 2013.
Wustner, D., et al., "Quantitative assessment of sterol traffic in living cells by dual labeling with dehydroergosterol and BODIPY-cholesterol", *Chemistry and Physics Lipids*, 164(3) 221-235 (2011).
Yogo, T. et al., "Highly Efficient and Photostable Photosensitizer Based on BODIPY Chromophore", *J. Am. Chem. Soc.*, 127, p. 12162-12163 (2005).
Yu, Y.H., et al., "Mono- and di(dimethylamino)styryl-substituted borondipyrromethene and borondi indomethene dyes with intense near-infrared fluorescence", *Chemistry, an Asian Journal*, 1(1-2): 176-197 (2006).
Thivierge, C., et al., "Spectral Dispersion and Water Solubilization of BODIPY Dyes via Palladium-Catalyzed C-H Functionalization", *American Chemical Society*, 9(11): 2135-2138 (2007).
International Search Report and the Written Opinion of the International Searching Authority mailed Sep. 12, 2012 of International Application No. PCT/SG2012/000215 filed on Jun. 15, 2012.
Jung, G. et al., "Solvent-dependent steady-state fluorescence spectroscopy for searching ESPT-dyes: solvatochromism of HPTS revisited", *Physical Chemistry Chemical Physics*, 11(9): 1416-1426 (2009).
Vendrell, M. et al., "Solid-phase synthesis of BODIPY dyes and development of an immunoglobulin Fluorescent sensor", *Chemical Communications*, 47(29): 8424-8426 (2011).

ALKYLAMINO BODIPY DYES AS SELECTIVE FLUORESCENT PROBES FOR PROTEINS AND MOUSE EMBRYONIC STEM CELLS

RELATED APPLICATION(S)

This application is the U.S. National Stage of International Application No. PCT/SG2012/000215, filed Jun. 15, 2012, which designates the U.S., published in English, and claims the benefit of U.S. Provisional Application No. 61/497,145, filed on Jun. 15, 2011. The entire teachings of the above application(s) are incorporated herein by reference.

BACKGROUND OF THE INVENTION

The development of small molecule sensors for the selective detection and imaging of proteins and certain cell types has great implications for biomedical and basic research. In particular, small molecule fluorophores have received significant attention as sensors in flow cytometry and fluorescence microscopy. Identification of small molecule fluorophores able to selectively discriminate one protein from a complex mixture is a challenge in this field. Similarly, the development of a sensor capable of selectively staining certain cell types is highly desirable in cell-imaging research.

BODIPY (4,4-difluoro-4-bora-3a,4a-diaza-s-indacene) has been widely used as a fluorophore due to its high photostability and extinction coefficient, high quantum yield and narrow excitation/emission bandwidth.[1-3] In order to develop fluorescent sensors and probes,[4-7] several chemical reactions have been adapted to the BODIPY scaffold. Mono- and difunctionalized BODIPY derivatives can be prepared by solution-phase chemistry using nucleophilic and oxidative nucleophilic hydrogen substitutions,[8-10] Knoevenagel condensations,[11,12] Liebeskind-Srogl reactions,[13,14] and palladium-catalyzed couplings[15-18] amongst others. However, solution-phase syntheses of BODIPY dyes often encompass tedious purification steps with typically low recovery yields. This limitation may have little impact on the synthesis of individual compounds, but it seriously hampers the combinatorial derivatization of the BODIPY scaffold,[19-21] requiring labor intensive purification processes. Solid-phase methodologies have been successfully applied to the diversification of fluorescent scaffolds that involve challenging purification steps, but the adaptability of the BODIPY structure to solid-phase chemistry has been questioned due to its lability under both basic and acidic conditions.[22]

Due to the current limitations associated with solid-phase synthesis of BODIPY scaffolds, and due to their potential to operate as selective sensors in protein and cell detection and imaging, it is highly desirable to develop a combinatorial solid-phase synthesis of the BODIPY scaffold.

SUMMARY OF THE INVENTION

New methodologies for solid-phase synthesis of alkylamino BODIPY dyes are described herein, and include the development of selective fluorescent probes for proteins (i.e., immunoglobulins) and cell-types (i.e. mouse embryonic stem cells), and their use in target identification approaches by conjugation to chemical or photoreactive tags. These can be used as ratiometric sensors.

The present invention discloses the first solid-phase synthesis of an alkylamino BODIPY library in high purities after minimum purification steps. The alkylamino BODIPY dyes were further derivatized with chemical and photoreactive tags and the resulting compounds were assayed in two screening platforms: 1) in vitro spectral analysis against diverse purified proteins; 2) high-throughput fluorescence microscopy against a panel of different cell types. These two screenings led to the discovery of an alkylamino BODIPY immunoglobulin fluorescent sensor (Ig Orange, formula (II)), and to an acetylated alkylamino BODIPY dye (CDy9, formula (IV)) which proved to selectively stain mouse embryonic stem cells (mESC) with an excellent potential for cell imaging and flow cytometry applications.

In one embodiment of the invention, an alkylamino BODIPY dye is disclosed having the structure of formula (I).

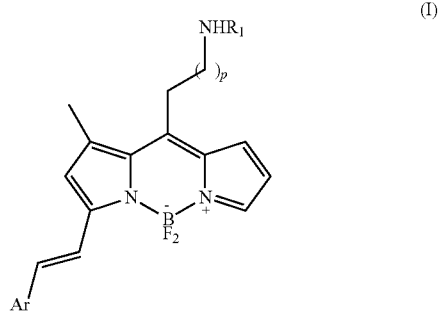

wherein:
Ar is

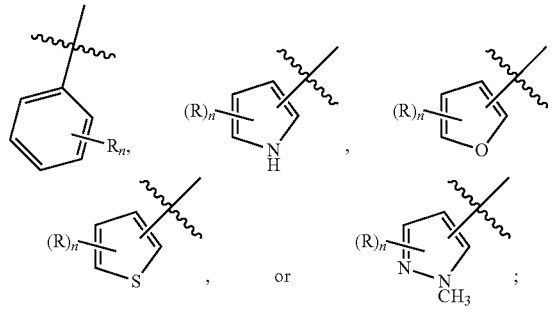

each R is independently selected from H, OH, halogen, nitro, amino, $(C_1-C_6)$alkyl, $(C=O)(C_0-C_6)$alkyl, $(C=O)O(C_0-C_6)$alkyl, $NH(C=O)(C_0-C_6)$alkyl, $OCF_3$, $CH=CH(C_0-C_6)$alkyl aryl, $O(C_1-C_6)$alkenyl, $(C_0-C_6)$alkylCH=O, $O(C_1-C_6)$alkyl, $S(C_1-C_6)$alkyl, $S(C_1-C_6)$haloalkyl, $O(C_1-C_6)$haloalkyl, $OCHF_2$, $O(C_0-C_6)$alkylamino, $(C_6-C_{10})$aryl, $(C_5-C_{10})$heteroaryl, $(C_5-C_{10})$heterocyclyl, $(C_1-C_6)$alkyl aryl, $O(C_0-C_6)$alkyl aryl, $O(CH_2)_m CHCH_2$ or 1-5-membered polycyclyl, wherein each 1-5-membered polycycle optionally and independently contains 1-2 ring heteroatoms selected from oxygen, nitrogen and sulfur;
n is 1, 2, 3 or 4;
m is 0, 1, 2, 3 or 4;
p is 1, 2, 3, 4, or 5;
wherein, when n is 2 or greater, the R substituents may be optionally taken together to form a fused polycyclic aromatic ring system;
and wherein each R is optionally substituted with 1-4 $R_2$ substituents independently selected from:
$(C_1-C_6)$alkyl, halo$(C_0-C_6)$alkyl, hydroxy$(C_0-C_6)$alkyl, $(C_6-C_{10})$aryl, halo $(C_6-C_{10})$aryl, hydroxy$(C_6-C_{10})$aryl, O($C_1$-$C_6$)alkyl, O($C_1$-$C_6$)haloalkyl, ($C_3$-$C_8$)cycloalkyl, halo($C_6$-$C_{10}$)aryl($C_1$-$C_6$)alkoxy, halogen, amino, ($C_1$-$C_6$)alkoxy($C_6$-$C_{10}$)aryl($C_1$-$C_6$)alkoxy, nitro, hydroxy, halogen, ($C_0$-$C_6$)alkyl($C_6$-$C_{10}$)aryl($C_0$-$C_6$)alkoxy, ($C_5$-$C_{10}$)heterocycle, $OCF_3$, amino, O($C_1$-$C_6$)alkylamino, ($C_6$-$C_{10}$)aryl($C_2$-$C_6$)alkenyl, ($C_2$-$C_6$)alkenyl($C_1$-$C_6$)alkoxy, ($C_1$-$C_6$)sulfoxy, or (C=O)O($C_0$-$C_6$)alkyl; and $R_1$ is H, C=O($C_0$-$C_6$)haloalkyl, C=O($C_0$-$C_6$)alkyl, C=O($C_0$-$C_6$)alkylene or C=O($C_6$-$C_{10}$)aryl;

or a pharmaceutically acceptable salt thereof.

In one embodiment of the invention, R in formula (I) is CH=CH($C_0$-$C_6$)alkyl aryl, and n is 1. In a preferred embodiment of the invention, R is (CH=CH)phenyl. In another embodiment of the invention, each $R_2$ is independently selected from the group comprising H, halogen, ($C_1$-$C_6$)haloalkyl, or ($C_1$-$C_6$)alkyl. In a more preferred embodiment of the invention, an alkylamino BODIPY dye is disclosed, having the formula (II).

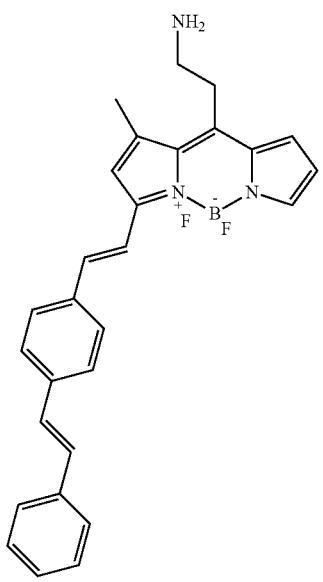

(II)

Also disclosed herein is a method for a solid phase synthesis of alkylamino BODIPY dyes having the structure of formula (I), and pharmaceutically acceptable salts thereof. In one aspect of the invention, this method comprises the steps of a) reacting an Fmoc-protected amino acid and pyrrole to form a 2-ketopyrrole of formula 1;

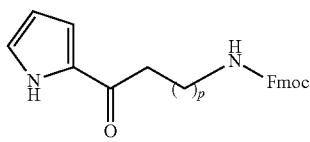

1 wherein p is an integer from 1 to 5;

b) condensing the 2-ketopyrrole of formula 1 with 2,4-dimethylpyrrole and an activating agent with in situ addition of $BF_3 \cdot OEt_2$ to obtain compound 2;

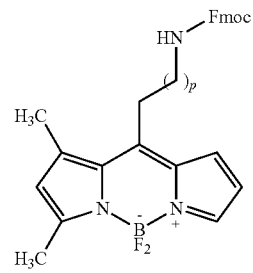

2 wherein p is an integer from 1 to 5;

c) reacting compound 2 with a base; d) quenching the reaction mixture of step c) with aqueous HCl to produce derivative 3;

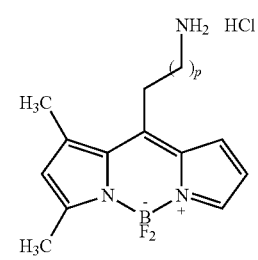

3 wherein p is an integer from 1 to 5;

e) loading the derivative of formula 3 on chlorotrityl chloride-polystyrene (CTC-PS) resin, so that the activated $C_3$-methyl group of the derivative is modified in a solid-phase adapted Knoevenagel-type reaction; and f) extracting the compounds of formula (I) from step e) by a solid-phase extraction.

In another embodiment of the invention, an alkylamino BODIPY dye having the structure of formula (III) is disclosed.

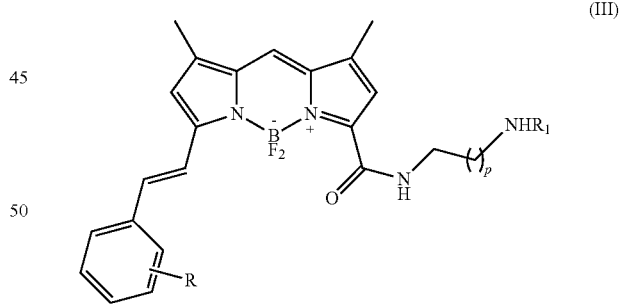

(III)

wherein:
each R is independently selected from H, OH, halogen, nitro, amino, ($C_1$-$C_6$)alkyl, (C=O)($C_0$-$C_6$)alkyl, NH(C=O)($C_0$-$C_6$)alkyl, $OCF_3$, CH=CH($C_0$-$C_6$)alkylaryl, $OC_1$-$C_6$ alkenyl, ($C_0$-$C_6$)alkylCH=O, O($C_1$-$C_6$)alkyl, S($C_1$-$C_6$)alkyl, S($C_1$-$C_6$)haloalkyl, O($C_1$-$C_6$)haloalkyl, $OCHF_2$, O($C_0$-$C_6$)alkylamino, ($C_6$-$C_{10}$)aryl, ($C_5$-$C_{10}$)heteroaryl, ($C_5$-$C_{10}$)heterocyclyl, ($C_1$-$C_6$)alkyl aryl, O($C_0$-$C_6$)alkyl aryl, O($CH_2$)$_m$$CHCH_2$ or 1-5 member polycyclyl, wherein each 1-5 member polycycle optionally and independently contains 1-2 ring heteroatoms selected from oxygen, nitrogen and sulfur;

n is 1, 2, 3 or 4;
m is 0, 1, 2, 3 or 4;
p is 1, 2, 3, 4, or 5;
wherein, when n is 2 or greater, the R substituents may be optionally taken together to form a fused polycyclic aromatic ring system;
and wherein each R is optionally substituted with 1-4 $R_2$ substituents independently selected from:
$(C_1-C_6)$alkyl, halo$(C_0-C_6)$alkyl, hydroxy$(C_0-C_6)$alkyl, $(C_6-C_{10})$aryl, halo$(C_6-C_{10})$aryl, hydroxy$(C_6-C_{10})$aryl, $O(C_1-C_6)$alkyl, $O(C_1-C_6)$haloalkyl, $(C_3-C_8)$cycloalkyl, halo$(C_6-C_{10})$aryl$(C_1-C_6)$alkoxy, halogen, amino, $(C_1-C_6)$alkoxy$(C_6-C_{10})$aryl$(C_1-C_6)$alkoxy, nitro, hydroxy, halogen, $(C_0-C_6)$alkyl$(C_6-C_{10})$aryl$(C_0-C_6)$alkoxy, $(C_5-C_{10})$heterocycle, $OCF_3$, amino, $O(C_1-C_6)$alkylamino, $(C_6-C_{10})$aryl$(C_2-C_6)$alkenyl, $(C_2-C_6)$alkenyl$(C_1-C_6)$alkoxy, $(C_1-C_6)$sulfoxy, $(C=O)O(C_0-C_6)$alkyl or $N(CH_3)(C_1-C_6)OH$;
$R_1$ is H, $C=O(C_0-C_6)$haloalkyl, $C=O(C_0-C_6)$alkyl, $C=O(C_0-C_6)$alkylene or $C=O(C_6-C_{10})$aryl;
or a pharmaceutically acceptable salt thereof.

In another aspect of the invention, the alkylamino BODIPY dye is represented by formula (IV):

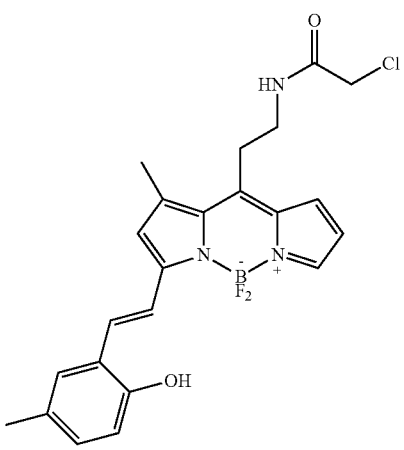

(IV)

Also described herein are methods of use for the alkylamino BODIPY compounds of the present invention. In one aspect, alkylamino BODIPY dyes having the structure of formula (I) are used as fluorescent sensors for the identification, detections, and fluorescence imaging of cells, as well as for cytometry applications. A method for protein detection by fluorescence analysis utilizing these compounds is presently disclosed. Similar to compounds of formula (I), compounds of formula (III) may be used for the identification, detections, and fluorescence imaging of cells, and cytometry applications. In one aspect of the invention, the compounds may be used to image mouse embryonic stem cells (mESC). Furthermore, compounds of formula (III) are also utilized in the detection of proteins by fluorescence analysis.

A method for staining cells utilizing a compound of formula (I) or (III) is also disclosed herein. In a particular embodiment of the invention, mouse embryonic stem cells (mESC) are stained.

The present invention also discloses a method for the solid phase synthesis of compounds of Formula (III), and pharmaceutically acceptable salts thereof. In one aspect of the invention, this method comprises the steps of a) reacting 3,5-dimethylpyrrole-2-carboxaldehyde with 2,4-dimethylpyrrole to prepare tetramethylBODIPY 4;

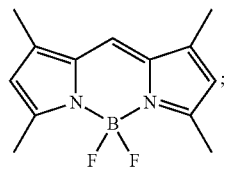

4 b) treating 4 with an oxidant to obtain compound 5;

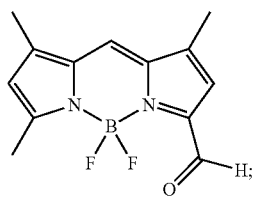

5 c) reacting compound 5 with a second oxidant to form derivative 6

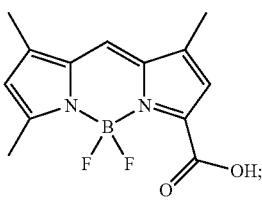

6 d) coupling 6 with alkylenediamine bound to chlorotrityl chloride-polystyrene (CTC-PS) resin, such that the activated $C_3$-methyl group of the derivative is modified in a solid-phase adapted Knoevenagel-type reaction; and
e) extracting the compound of Formula (III) from step d) by a solid-phase extraction.

Also disclosed herein are compounds in which the alkylamino moiety

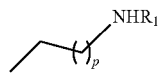

on the BODIPY dyes of formula (I) or the alkylamino group

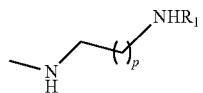

of formula (III) may be further modified by conjugation to chemically reactive or photoreactive tags.

The alkylamino BODIPY dyes of the invention are fabricated by the first reported solid phase synthesis. This method begins with simple starting materials, and generates the products in high yields after minimum purification, a significant departure from solution phase syntheses which typically require tedious purification and result in low material recovery. This synthetic route is highly tunable, allowing for the rapid generation of a library of alkylamino BODIPY dyes, a task which would have been restricted by previously reported syntheses. Furthermore, this scaffold is easily modified by the addition of chemically reactive or photoreactive tags, emphasizing its utility as a sensor in detection and imaging of proteins and cells. Compounds of the present invention are used as selective fluorescent turn-on probes for protein detection. Furthermore, certain compounds of the present invention are selective for staining mouse embryonic stem cells (mESC) over other differentiated cells types, which holds great utility for imaging, characterization, and isolation. This method is particularly advantageous over established methods because it is non-destructive and requires no genetically modified cells.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

FIG. 6b shows the determination of the region of human IgG for the binding to Ig Orange (BDM-69) by fluorescence increase of Ig Orange upon incubation with $F_{ab}$ and $F_c$ fragments of human $IgG_1$ and Job plot analysis. Values are represented as means (n=3) and error bars as standard deviations.

In FIG. 10a, mESC were selectively stained by CDy9 at 500 nM for 1 h (right) compared to mouse embryonic fibroblasts (MEF, left), and in FIG. 10b, CDy9 was analyzed by flow cytometry. Cells were loaded after 1 h incubation at 500 nM. Magnification 10×, fluorescent images (TRITC/TXRed filters for CDy9, DAPI for nuclear staining).

In FIG. 11a, differentiated mESC were no longer stained by CDy9 (500 nM, 1 h) upon differentiation, while in FIG. 11b CDy9 selectively stained only mESC and not any differentiated cell lineages such as mouse neuro stem cell (NS5), NS5-derived astrocytes, primary mouse neurons, mouse mixed glial cells, mouse fibroblast (3T3), mouse fibroblast-adipocytes (3T3-L1), mouse alpha TC-1cells, mouse beta TC-6 cells and mouse primary liver cells.

DETAILED DESCRIPTION OF THE INVENTION

Figure 1:
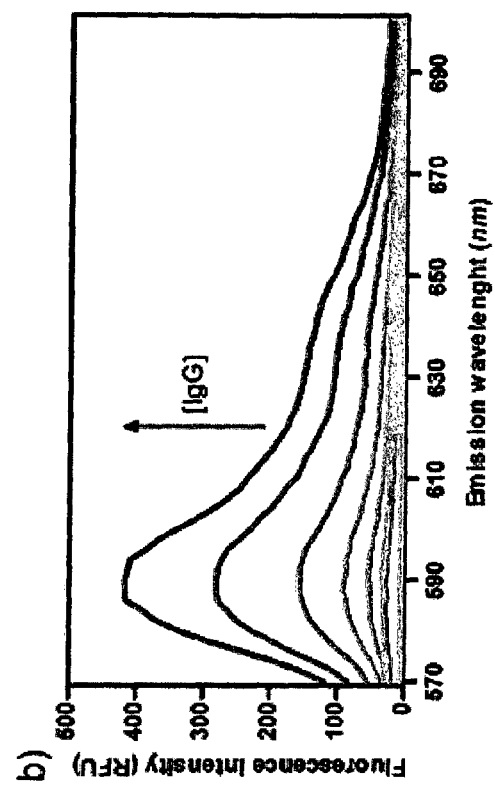
FIGS. 1a and 1b show the chemical structure of Ig Orange (BDM-69) and its fluorescence response against different proteins and peptides (20 mM HEPES buffer, pH 7.4; excitation wavelength: 510 nm, emission wavelength: 590 nm), and the fluorescence spectra of Ig Orange (BDM-69) upon increasing concentrations of human IgG (0, 1, 2, 4, 8, 17, 33 and 67 µM) in 20 mM HEPES buffer pH 7.4; excitation wavelength: 530 nm.
Figure 1:
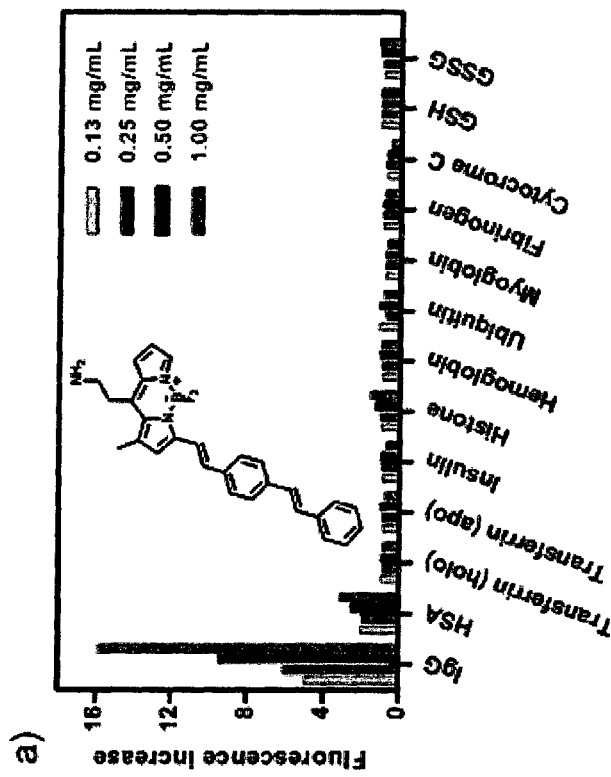

A description of example embodiments of the invention follows.

In this invention, we disclose the first solid-phase synthesis of an alkylamino BODIPY library. The synthesis was designed to include a solid-supported aminoalkyl BODIPY-scaffold as a common intermediate, which would be efficiently functionalized via a solid phase-adapted Knoevenagel reaction in order to generate a library of alkylamino BODIPY dyes. The alkylamino BODIPY dyes of the invention demonstrate diverse utility as sensors for detection and imaging applications in biomedical and basic research. Due to its high photostability and extinction coefficient, as well as its narrow excitation and emission bandwidth, the BODIPY scaffold is an effective fluorophore for use as a sensor with protein samples. Furthermore, these alkylamino BODIPY scaffolds hold potential for use in selective staining of certain lines of stem cells.

Synthesis of an Alkylamino BODIPY Library.

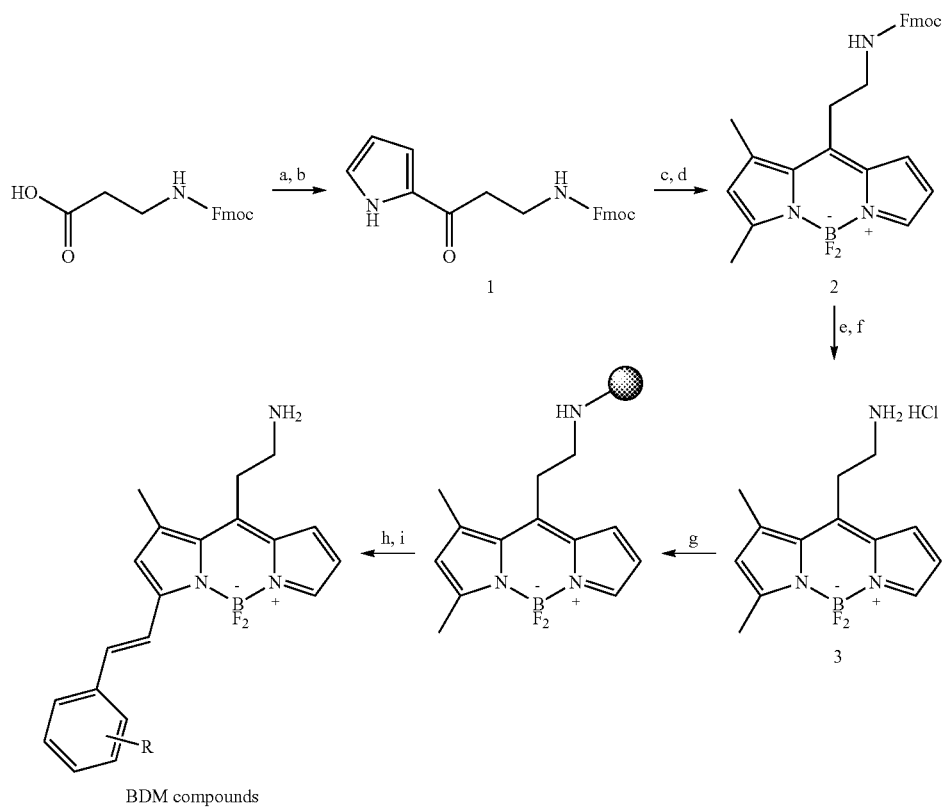

Scheme 1: Representative synthesis of the alkylamino BODIPY scaffold 3 and its derivatization in solid-phase to render substituted aminoethyl BODIPY compounds. Reagents and conditions: a) 2,2'-dipyridyldisulfide, dry tetrahydrofuran, room temperature, 20 h; b) pyrrole, CH$_3$MgBr, dry tetrahydrofuran, -78° C., 1 h; c) 2,4-dimethylpyrrole, POCl$_3$, CH$_2$Cl$_2$, 35° C., 20 h; d) BF$_3$·OEt$_2$, diisopropylethylamine, CH$_2$Cl$_2$, room temperature, 4 h; e) 1,8-Diazabicyclo[5.4.0]undec-7-ene, CH$_2$Cl$_2$, room temperature, 1 h; f) diluted HCl (aq); g) chlorotrityl chloride-polystyrene (CTC-PS) resin, diisopropylethylamine, N-methylpyrrolidone, room temperature, 20 h; h) RCHO, pyrrolidine, AcOH, dimethylsulfoxide-acetonitrile (1:1), 85° C., 5-10 min; i) trifluoroacetic acid-CH$_2$Cl$_2$ (0.5:99.5), room temerature, 2 × 10 min.

Scheme 1 shows a representative synthesis of an alkylamino-containing BODIPY scaffold 3, its binding to a solid support resin, and its solid-supported derivitization to a substituted alkylamino-BODIPY dye. The starting material in the invention is an N-Fmoc-alkylamino acid, where Fmoc is 9-fluorenylmethyloxycarbonyl. In some embodiments of the invention, the starting material can be N-Fmoc-7-aminoheptanoic acid, N-Fmoc-6-aminohexanoic acid, N-Fmoc-5-amino-pentanoic acid, N-Fmoc-4-aminobutanoic acid, or N-Fmoc-β-alanine. In a preferred embodiment of the invention, and as is shown in the representative synthesis of an alkylamino-containing BODIPY scaffold 3 in Scheme 1, the starting material for this transformation is N-Fmoc-β-alanine. In steps a-b, N-Fmoc-β-alanine is reacted with 2,2'-dipyridyldisulfide followed by reaction with pyrrole at about -78° C. to generate compound 1. In one aspect of the invention, the preceding transformations take place in an organic solvent selected from a list comprising toluene, tetrahydrofuran, diethyl ether, and dichloromethane, and in a preferred embodiment, the preceding transformation is carried out in tetrahydrofuran.

In steps c-d, the amide formed in the preceding reaction, of which 1 is representative, is then reacted with 2,4-dimethylpyrrole and an activating agent at about 35° C. in an organic solvent. In some embodiments of the invention, the activating reagent is trifluoroacetic acid or POCl$_3$. In preferred embodiment of the invention, the activating agent is POCl$_3$. In certain embodiments of the invention, the organic solvent is a chlorinated organic solvent such as dichloroethane, dichloromethane, or chloroform, and in a more preferred embodiment of the invention, the solvent is dichloromethane. Then, BF$_3$.OEt$_2$ is added in situ and a BODIPY derivative in generated, as is represented by 2 in Scheme 1. Next, in step e, the protecting group is removed from nitrogen by addition of a base. In one aspect of the invention, this is accomplished by the addition of piperidine, solid-supported piperidine or DBU (1,8-Diazabicycloundec-7-ene), and in a preferred embodiment, the deprotection results from the addition of DBU (1,8-Diazabicycloundec-7-ene). An acid salt of the amine is then generated in step f, which occurs by addition of an aqueous solution of an acid. In some embodiments of the invention, the acid can be hydrochloric acid, hydrobromic acid, hypochlorous acid, phosphoric acid, or acetic acid, while in preferred embodiments of the invention, the acid salt of the amine is formed from the addition of hydrochloric acid (HCl).

In step g, the amine salt is loaded onto a solid support resin. In a preferred embodiment, the salt is loaded onto a chlorotrityl chloride polystyrene (CTC-PS) resin. Next, in step h of Scheme 1, the activated $C_3$-methyl group of the BODIPY structure could be modified in a solid-phase adapted Knoevenagel-type reaction[24] by reaction with an aldehyde of the formula ArCHO, wherein:
Ar is

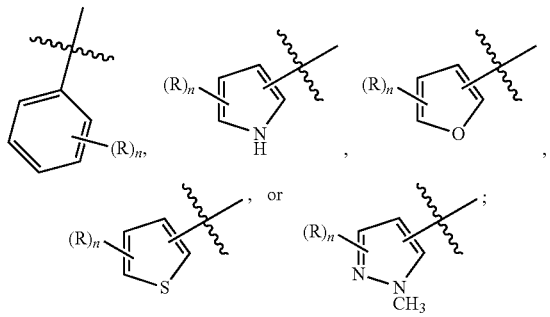

each R is independently selected from H, OH, halogen, nitro, amino, $(C_1-C_6)$alkyl, $(C=O)(C_0-C_6)$alkyl, $(C=O)O(C_0-C_6)$alkyl, $NH(C=O)(C_0-C_6)$alkyl, $OCF_3$, $CH=CH(C_0-C_6)$alkyl aryl, $O(C_1-C_6)$alkenyl, $(C_0-C_6)$alkylCH=O, $O(C_1-C_6)$alkyl, $S(C_1-C_6)$alkyl, $S(C_1-C_6)$haloalkyl, $O(C_1-C_6)$haloalkyl, $OCHF_2$, $O(C_0-C_6)$alkylamino, $(C_6-C_{10})$aryl, $(C_5-C_{10})$heteroaryl, $(C_5-C_{10})$heterocyclyl, $(C_1-C_6)$alkyl aryl, $O(C_0-C_6)$alkyl aryl, $O(CH_2)_mCHCH_2$ or 1-5 membered polycyclyl, wherein each 1-5-membered polycycle optionally and independently contains 1-2 ring heteroatoms selected from oxygen, nitrogen and sulfur;
n is 1, 2, 3 or 4;
m is 0, 1, 2, 3 or 4;
wherein, when n is 2 or greater, the R substituents may be optionally taken together to form a fused polycyclic aromatic ring system;
and wherein each R is optionally substituted with 1-4 $R_2$ substituents independently selected from:
$(C_1-C_6)$alkyl, halo$(C_0-C_6)$alkyl, hydroxy$(C_0-C_6)$alkyl, $(C_6-C_{10})$aryl, halo $(C_1-C_{10})$aryl, hydroxy$(C_6-C_{10})$aryl, $O(C_1-C_6)$alkyl, $O(C_1-C_6)$haloalkyl, $(C_3-C_8)$cycloalkyl, halo$(C_6-C_{10})$aryl$(C_1-C_6)$alkoxy, halogen, amino, $(C_1-C_6)$alkoxy$(C_6-C_{10})$aryl$(C_1-C_6)$alkoxy, nitro, hydroxy, halogen, $(C_0-C_6)$alkyl $(C_6-C_{10})$aryl$(C_0-C_6)$alkoxy, $(C_5-C_{10})$heterocycle, $OCF_3$, amino, $O(C_1-C_6)$alkylamino, $(C_6-C_{10})$aryl$(C_2-C_6)$alkenyl, $(C_2-C_6)$alkenyl$(C_1-C_6)$alkoxy, $(C_1-C_6)$sulfoxy, $(C=O)O(C_0-C_6)$alkyl or $N(CH_3)(C_1-C_6)OH$.

The cleavage conditions of step i are provided by about 0.5% trifluoroacetic acid in dichloromethane. A solid-phase extraction renders aminoethyl styryl-BODIPY compounds (BDM) with purities averaging about 91%. Example structures of BDM compounds and the characterization data is found in Table 1.

In another aspect of the invention, the incorporation of alkylamino moieties in the BODIPY core has been also accomplished in other positions of the BODIPY structure. This is demonstrated by Scheme 2, which shows a representative pathway for the synthesis of BDMD compounds. The synthesis of BDMD compounds begins by reacting 3,5-dimethylpyrrole-2-carboxaldehyde with 2,4-dimethylpyrrole to prepare tetramethyl BODIPY 4. Compound 4 is treated with an oxidant in step a to generate compound 5. In one aspect of the invention, the oxidant is selected from chloranil or DDQ (2,3-Dichloro-5,6-dicyano-1,4-benzoquinone). In a preferred embodiment of the invention, the oxidant is DDQ (2,3-Dichloro-5,6-dicyano-1,4-benzoquinone). Step b converts aldehyde 5 to carboxylic acid 6 by reacting with additional oxidant. In some preferred aspects of the invention, the oxidant to achieve this transformation is $NaClO_2$ with 2-methylbut-2-ene and $NaH_2PO_4$, or else potassium permanganate ($KMnO_4$).

In step c, carboxylic acid 6 is loaded onto a solid-supported resin containing an alkylenediamine linker. In a preferred embodiment of the invention, the acid is reacted with ethylenediamine-chlorotrityl chloride polystyrene (ethylenediamine-CTC-PS) resin. Analogous to the BDM compounds, in step d, the activated $C_3$-methyl group of the BODIPY structure could be modified in a solid-phase adapted Knoevenagel-type reaction[24] by reaction with an aldehyde of the formula (V).

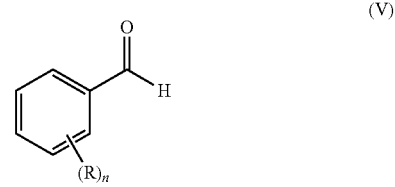

(V)

Wherein: each R is independently selected from H, OH, halogen, nitro, amino, $(C_1-C_6)$alkyl, $(C=O)(C_0-C_6)$alkyl, $(C=O)O(C_0-C_6)$alkyl, $NH(C=O)(C_0-C_6)$alkyl, $OCF_3$, $CH=CH(C_0-C_6)$alkyl aryl, $O(C_1-C_6)$alkenyl, $(C_0-C_6)$alkylCH=O, $O(C_1-C_6)$alkyl, $S(C_1-C_6)$alkyl, $S(C_1-C_6)$haloalkyl, $O(C_1-C_6)$haloalkyl, $OCHF_2$, $O(C_0-C_6)$alkylamino, $(C_6-C_{10})$aryl, $(C_5-C_{10})$heteroaryl, $(C_5-C_{10})$heterocyclyl, $(C_1-C_6)$alkyl aryl, $O(C_0-C_6)$alkyl aryl, $O(CH_2)_mCHCH_2$ or 1-5 membered polycyclyl, wherein each 1-5-membered polycycle optionally and independently contains 1-2 ring heteroatoms selected from oxygen, nitrogen and sulfur;
n is 1, 2, 3 or 4;
m is 0, 1, 2, 3 or 4;
wherein, when n is 2 or greater, the R substituents may be optionally taken together to form a fused polycyclic aromatic ring system;
and wherein each R is optionally substituted with 1-4 $R_2$ substituents independently selected from:
$(C_1-C_6)$alkyl, halo$(C_0-C_6)$alkyl, hydroxy$(C_0-C_6)$alkyl, $(C_6-C_{10})$aryl, halo $(C_6-C_{10})$aryl, hydroxy$(C_6-C_{10})$aryl, $O(C_1-C_6)$alkyl, $O(C_1-C_6)$haloalkyl, $(C_3-C_8)$cycloalkyl, halo$(C_6-C_{10})$aryl$(C_1-C_6)$alkoxy, halogen, amino, $(C_1-C_6)$alkoxy$(C_6-C_{10})$aryl$(C_1-C_6)$alkoxy, nitro, hydroxy, halogen, $(C_0-C_6)$alkyl $(C_6-C_{10})$aryl$(C_0-C_6)$alkoxy, $(C_5-C_{10})$heterocycle, $OCF_3$, amino, $O(C_1-C_6)$alkylamino, $(C_6-C_{10})$aryl$(C_2-C_6)$alkenyl, $(C_2-C_6)$alkenyl$(C_1-C_6)$alkoxy, $(C_1-C_6)$sulfoxy, $(C=O)O(C_0-C_6)$alkyl or $N(CH_3)(C_1-C_6)OH$;

The cleavage conditions of step e are provided by about 0.5% trifluoroacetic acid in dichloromethane.

Scheme 2.

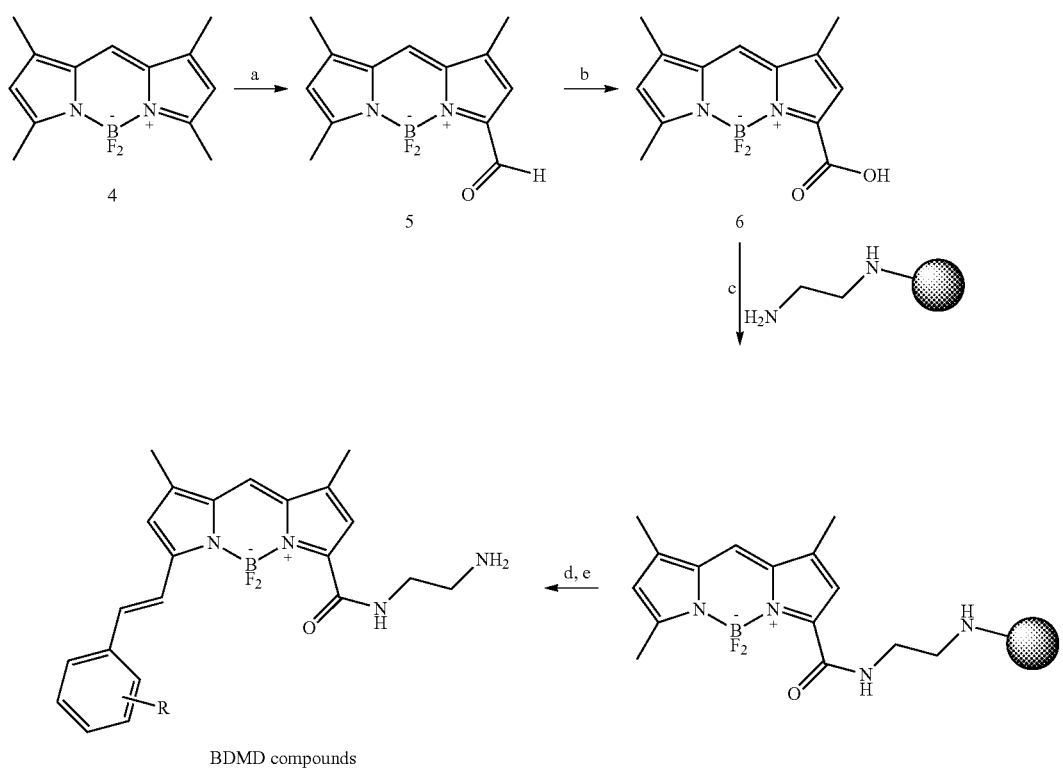

BDMD compounds

Scheme 2: Representative synthesis of the BODIPY scaffold 6 and its derivatization on solid-phase to render alkylamino BODIPY dyes (BDMD compounds) with different linker position. Reagents and conditions: a) 2,3-Dichloro-5,6-dicyano-1,4-benzoquinone, dry tetrahydrofuran, room temperature, 4 h; b) potassium permanganate, tetrahydrofuran; c) ethylenediamine-CTC-PS resin, diisopropylethylamine, N-methylpyrrolidone, r.t., 20 h; d) RCHO, pyrrolidine, AcOH, DMSO-ACN (1:1), 85° C., 5-10 min; e) TFA-DCM (0.5:99.5), r.t., 2 × 10 min.

The alkylamino linkers in both BDM and BDMD compounds of the present invention are particularly advantageous because they may be easily modified with chemically reactive or photoreactive tags. In some aspects of the invention, chemically reactive and photoreactive tags can be used for target identification studies, which is a key step and one of the bottlenecks of drug discovery and target validation programs. As depicted in Scheme 3, the BDM and BDMD compounds of the invention may undergo chemical modification of alkylamino moiety. In some aspects of the invention, this chemical modification is a purification-free, solid-phase approach that involves reaction of the amine groups with solid-supported reactive esters. In some aspects of the invention, the chemically reactive tag is in the form of an acetyl group, a chloroacetyl group, or an acryloyl group. In another aspect of the invention, the photoreactive tag is an alkyl- or aryl(trifluoromethyl)diazirine. In yet another aspect of the invention, any of the chemically reactive or photoreactive tags are utilized for the construction of FRET and/or ratiometric sensors.

Scheme 3.

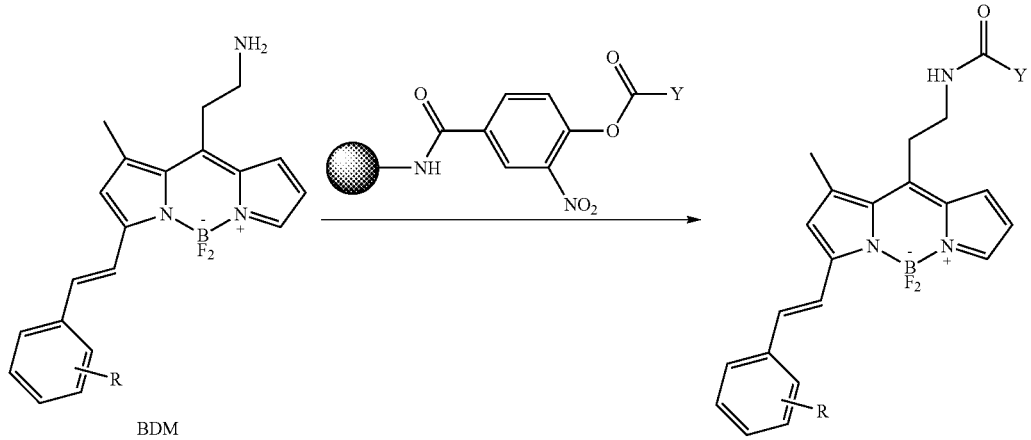

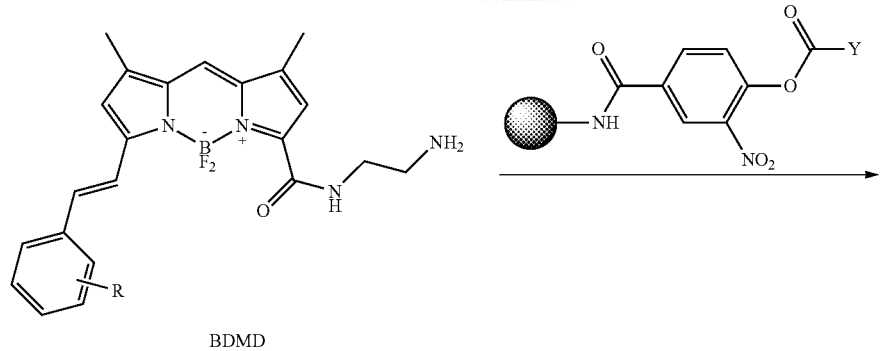

BDMD

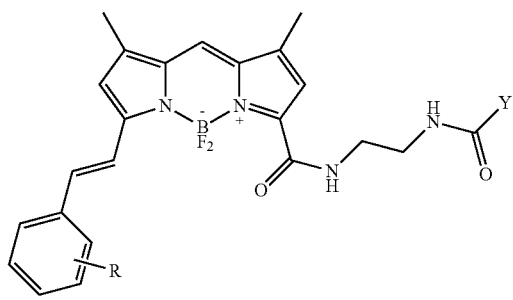

Y includes:

chemical reactive tags          photoreactive tags

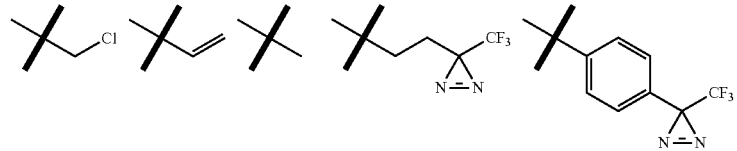

and fluorophores for FRET/ratiometric sensors

Scheme 3: Derivatization of BDM and BDMD compounds using a reactive ester support strategy. BDM and BDMD compounds may incorporate chemically reactive tags, photoreactive tags, or react with other acetylating reagents.

Use of BDM Compounds.

BDM compounds of the present invention show diverse spectroscopic properties ($\lambda_{abs}$: from about 536 to about 622 nm, $\lambda_{em}$: from about 561 to about 685 nm), with an average quantum yield around 0.3 that asserts their potential as fluorescent turn-on probes for proteins. In addition to acting as fluorescent sensors, the BDM compounds of the present invention are also particularly suitable for the imaging and staining of certain cell lines.

The discrimination of proteins in complex mixtures remains a challenging issue in sensor development. With the aim of discovering novel BODIPY-based fluorescent turn-on protein probes, the fluorescence properties of the whole library were examined against various proteins and peptides. A number of BDM compounds exhibit a turn-on effect upon incubation with different proteins/peptides, with BDM-69 demonstrating the best selectivity profile among the whole library (FIG. 1a). BDM-69 exhibits a remarkable 75-fold turn-on fluorescence increase in the presence of human IgG (FIG. 1b). On the basis of this selectivity pattern and fluorescence color, we named BDM-69 as Ig Orange.

Figure 6:
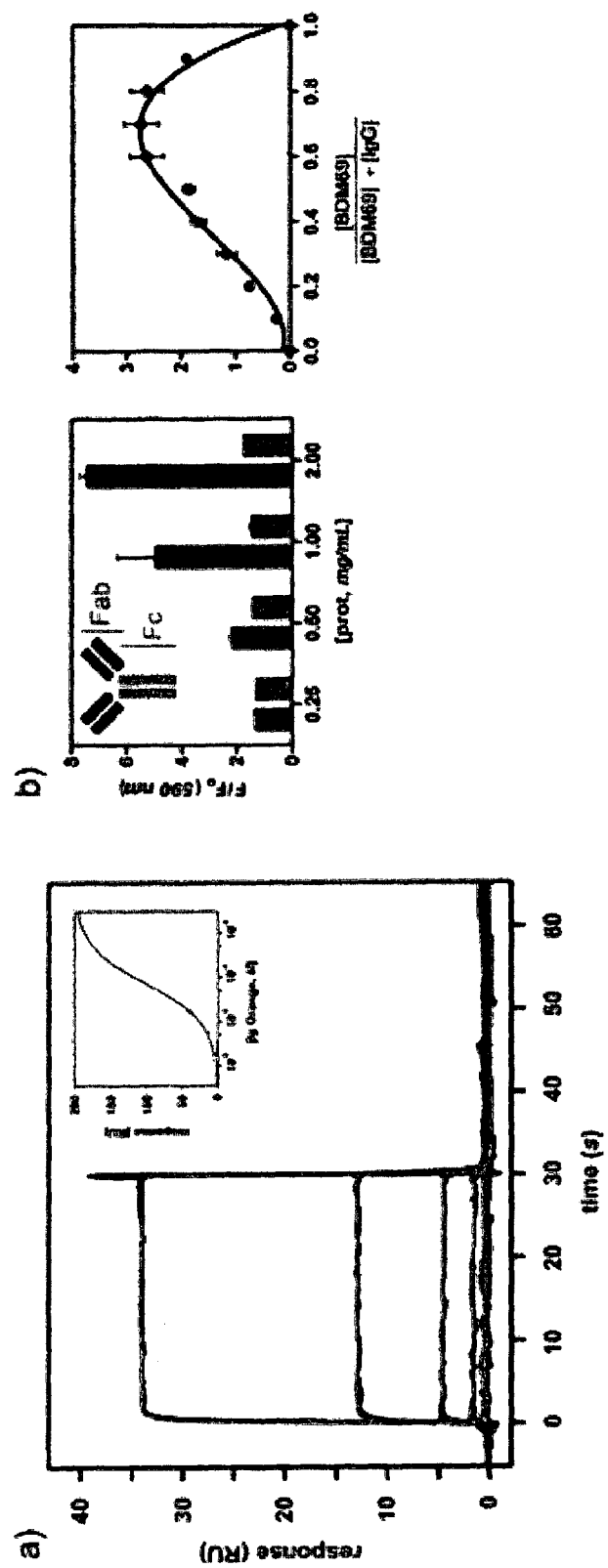
FIGS. 6a and 6b show binding sensorgrams of Ig Orange (0.07, 0.21, 0.62, 1.86, 5.57 and 16.70 µM) upon injection across an immobilized immunoglobulin chip, which were fit using the equilibrium responses of a steady-state model. The inset of FIG. 6a shows a fitting to an isotherm determined a $K_D$ value of 71.7±0.6 µM.
Figure 7:
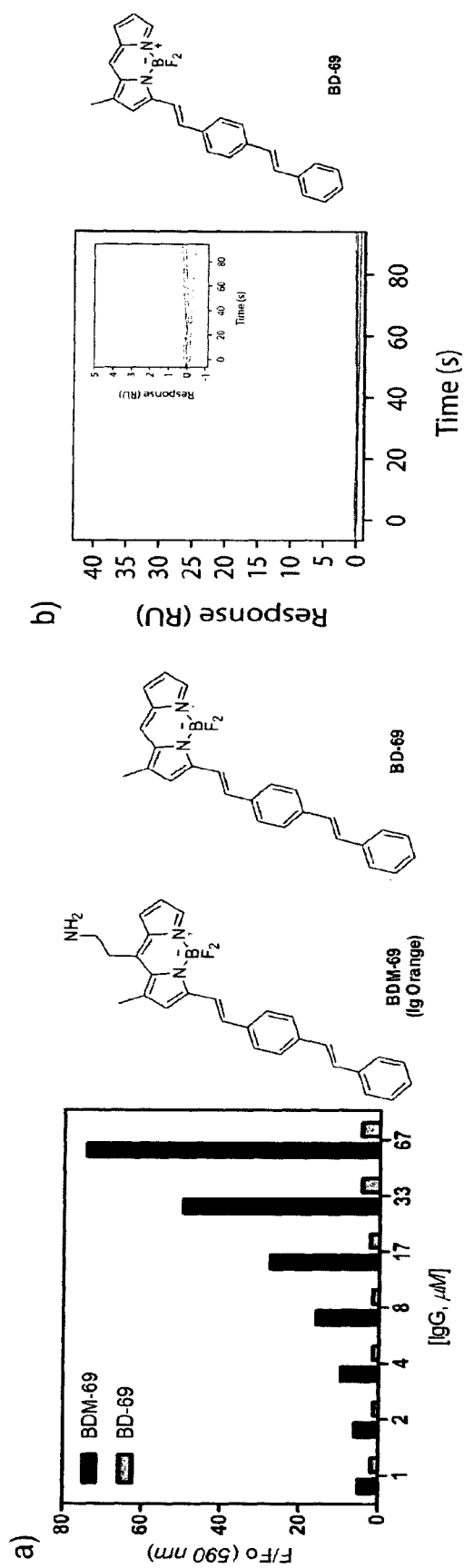
FIGS. 7a and 7b show the fluorescence response of Ig Orange (BDM-69) and BD-69 vs. human IgG, in which a 15-fold higher fluorescence increase was observed in the case of Ig Orange indicating the relevant contribution of the aminoethyl group in the interaction with human IgG, and also show binding sensorgrams of the aminoethyl-free compound (BD-69) upon injection across an immobilized immunoglobulin chip. Different concentrations of BD-69 were injected across a control surface and the immobilized surface serially for Ig Orange. The inset displays a zoom image of the sensorgrams.

The following experiments were aimed at determining the dissociation constant of the interaction between Ig Orange and human IgG. Surface Plasmon Resonance (SPR) has been extensively used to measure the binding constants between small molecules and biopolymers, 25 and we modified human IgG with biotin so that it could be immobilized on a neutravidin-coated sensor chip. Upon immobilization of the biotinylated protein on a neutravidin-coated sensor chip CM7, we performed Ig Orange titrations in duplicate with increasing concentrations of the small molecule. The resulting binding sensorgrams were fit using the equilibrium responses (steady-state model) with a KD value of 71.7±0.6 µM (FIG. 6a). Additional SPR experiments confirmed that both aminoethyl and stilbene moieties of Ig Orange were necessary for the interaction with the immunoglobulin, since the aminoethyl-free derivative of Ig Orange did not show any significant binding to human IgG (FIG. 7).

In order to identify the region of human IgG to which Ig Orange binds, we evaluated the fluorescence response of Ig Orange in the presence of human polyclonal IgG and monoclonal $IgG_1$, the most abundant subtype. Ig Orange underwent a similar turn-on effect in both cases, indicating that the binding took place at the backbone structure of the immunoglobulin rather than at the antigen-binding site. In view of this result, we analyzed the fluorescence increase after incubation with the separate $F_{ab}$ and $F_c$ fragments of the human monoclonal $IgG_1$. As shown in FIG. 6b, Ig Orange exhibited a preferred binding to the $F_{ab}$ region of the immunoglobulin when compared to the $F_c$ fragment. To confirm this observation and determine the stoichiometry of the complex between Ig Orange and the full immunoglobulin, we analyzed the interaction by means of a Job plot. A maximum fluorescence increase was detected for a 2:1 Ig Orange:immunoglobulin ratio, which supported our observation that the preferred binding region of Ig Orange corresponded to the $F_{ab}$ fragments of the immunoglobulin (FIG. 7b). In conclusion, the analysis of the fluorescence response of Ig Orange with the two $F_{ab}$ and $F_c$ fragments of an immunoglobulin pointed out that Ig Orange preferably bound to the $F_{ab}$ region of the backbone structure of the immunoglobulin, which is consistent with the 2:1 stoichiometry for the Ig Orange:immunoglobulin complex determined by Job plot analysis. With this first adaptation of the BODIPY scaffold to a solid-phase approach we accelerated the development of alkylamino BODIPY-based fluorescent probes, being Ig Orange the first immunoglobulin fluorescent sensor.

Figure 10:
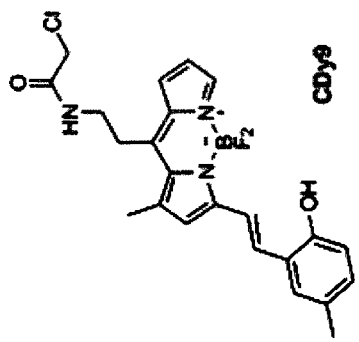
FIGS. 10a and 10b show mouse embryonic stem cell staining and flow cytometry by CDy9.
Figure 10:
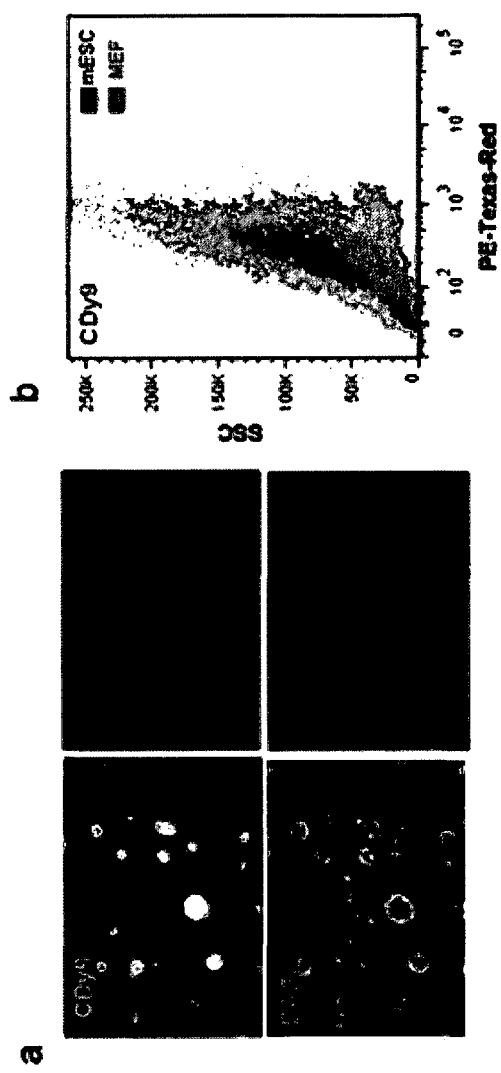

Alkylamino BODIPY probes may also be used to selectively stain mESC (mouse embryonic stem cells). To determine which BODIPY compounds of the invention are preferred probes, we assayed the staining properties of BDM compounds and their corresponding chloroacetylated derivatives in a high-throughput cell imaging-based screening. CDy9 was identified as the BODIPY compound that stained mESC and not MEF (mouse embryonic fibroblast) in the most selective manner (FIG. 10a). Furthermore, flow cytometry assays proved that CDy9 could be used for the isolation and characterization of mESC (FIG. 10b). In addition to its excellent potential for the imaging, isolation and characterization of mESC, CDy9 overcomes some limitations of the conventionally stem cell research tools for mESC identification such as antibodies or GFP/luciferase-based mESC reporters by providing a protocol that is non-destructive, simple and does not require genetically-modified cells.

Figure 11:
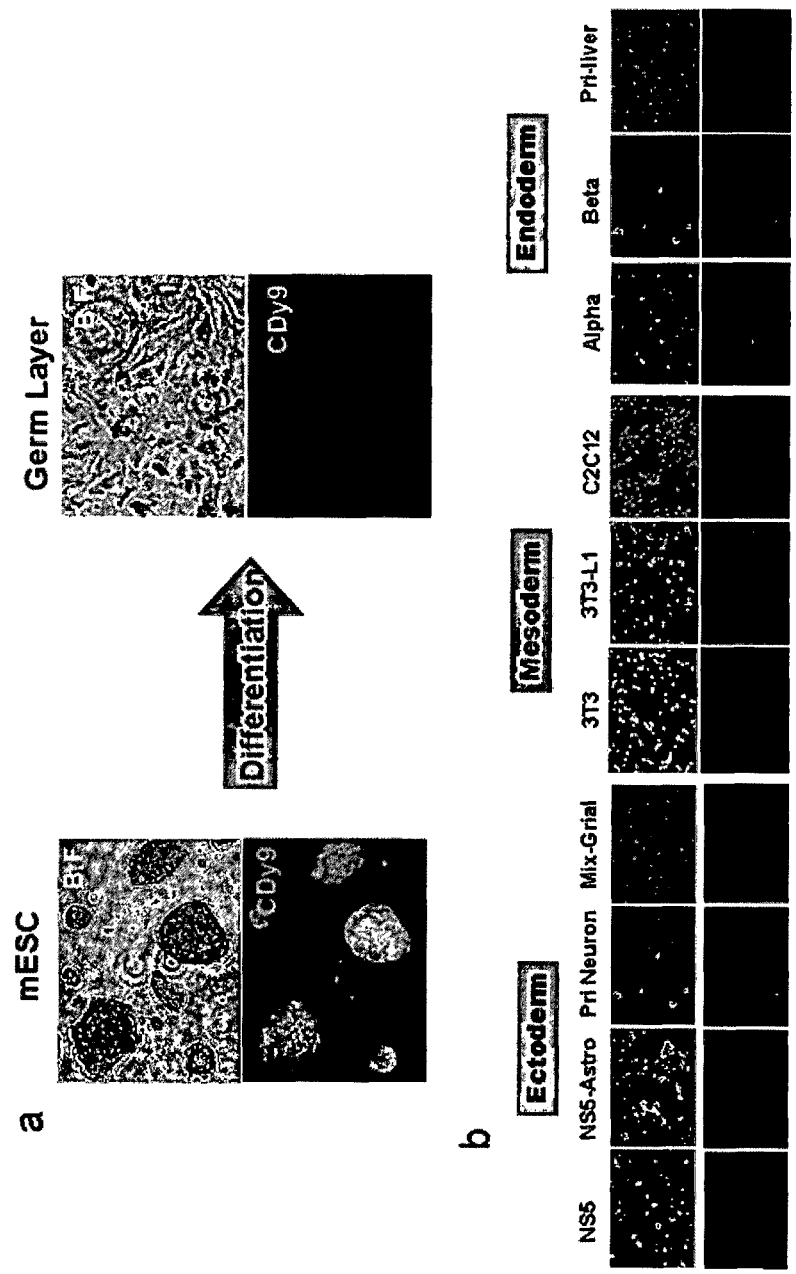
FIGS. 11a and 11b show selective staining of CDy9 in mESC against a wide panel of differentiated cell types.

After identifying the potential of CDy9 for mESC staining, we further evaluated its selectivity against a wide panel of different cell lines. Fluorescent mESC probes must ideally turn-on only in the presence of mESC and not fluoresce whenever mESC are differentiated into other lineages. As shown in FIG. 11a, CDy9 can selectively stain mESC and not those cells which undergo a differentiation process. In addition, we proved that CDy9 does not stain any of the three germ layers (ectoderm, mesoderm and endoderm) in which mESC can differentiate to. CDy9 showed no staining in a number of cell lines from the different germ layers (FIG. 11b, ectoderm: mouse neuro stem cell (NS5), NS5-derived astrocytes, primary mouse neurons and mouse mixed glial cells; mesoderm: mouse fibroblasts (3T3 and C2C12) and mouse fibroblast-adipocytes (3T3-L1); endoderm: mouse alpha TC-1cells, mouse beta TC-6cells and mouse primary liver cells), which demonstrates its general application as a fluorescent probe for the imaging, isolation and characterization of mESC.

The alkylamino BODIPY dyes of the invention show particular utility as selective fluorescent sensors for use with proteins and certain cell lines. Furthermore, they selectively stain mESC over MEF, which holds great potential for biomedical research applications.

TABLE 1

Chemical structures and characterization data for the BDM library.

| Code | Structure | Mcalc. | Mexp. | tR (min) | purity | λmax (ABS) | λmax (EM) | φ | mg |
|---|---|---|---|---|---|---|---|---|---|
| BDM-1 | 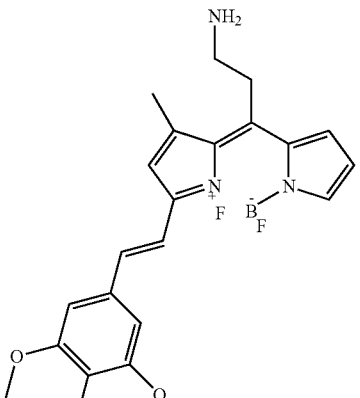 | 441.3 | 422.0 | 3.74 | 87% | 561 | 586 | 0.21 | 5.1 |

TABLE 1-continued
Chemical structures and characterization data for the BDM library.
| Code | Structure | Mcalc. | Mexp. | tR (min) | purity | λmax (ABS) | λmax (EM) | φ | mg |
|---|---|---|---|---|---|---|---|---|---|
| BDM-2 | 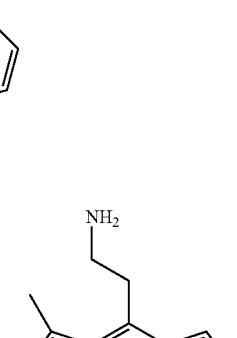 | 394.3 | 375.0 | 3.96 | 88% | 607 | 685 | 0.01 | 5.8 |
| BDM-3 | 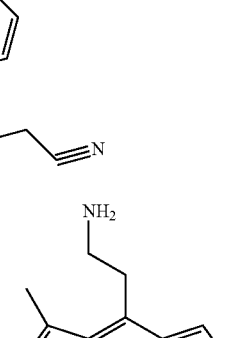 | 433.3 | 414.0 | 4.02 | 87% | 600 | 683 | 0.05 | 5.9 |
| BDM-4 | 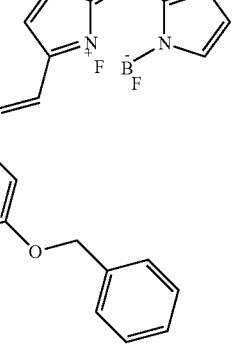 | 563.4 | 543.9 | 5.48 | 95% | 566 | 590 | 0.42 | 6.1 |

TABLE 1-continued

Chemical structures and characterization data for the BDM library.

| Code | Structure | Mcalc. | Mexp. | tR (min) | purity | λmax (ABS) | λmax (EM) | φ | mg |
|---|---|---|---|---|---|---|---|---|---|
| BDM-5 | 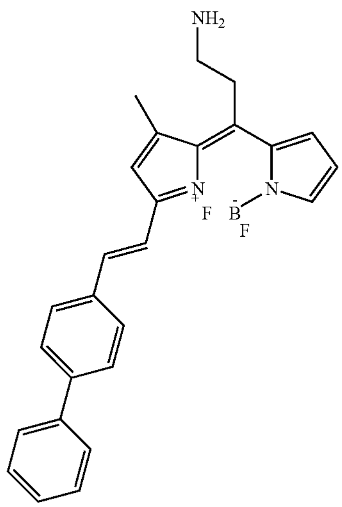 | 427.3 | 408.0 | 5.16 | 96% | 561 | 575 | 0.50 | 7.7 |
| BDM-6 | 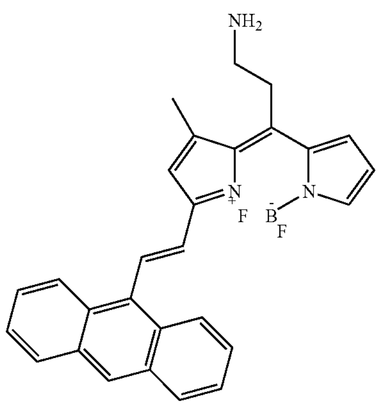 | 451.3 | 432.0 | 4.97 | 89% | 536 | 682 | 0.12 | 9.0 |
| BDM-7 | 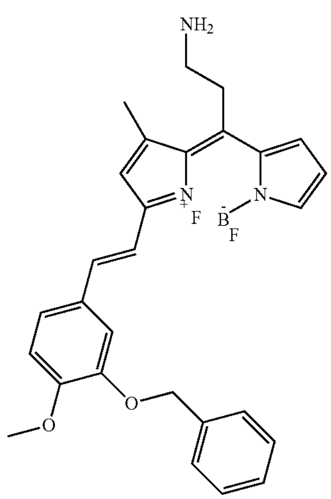 | 487.3 | 467.9 | 4.68 | 89% | 566 | 591 | 0.37 | 6.6 |

TABLE 1-continued

Chemical structures and characterization data for the BDM library.

| Code | Structure | Mcalc. | Mexp. | tR (min) | purity | λmax (ABS) | λmax (EM) | φ | mg |
|---|---|---|---|---|---|---|---|---|---|
| BDM-8 | 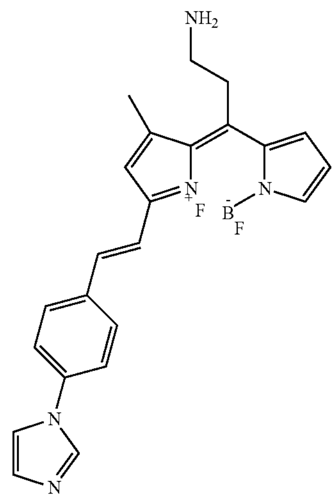 | 417.3 | 418.0 | 2.31 | 95% | 561 | 575 | 0.34 | 3.9 |
| BDM-9 | 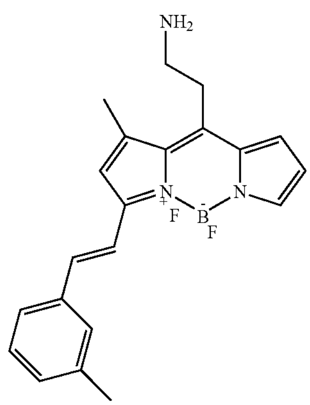 | 365.3 | 346.0 | 4.21 | 88% | 554 | 567 | 0.33 | 3.5 |
| BDM-12 | 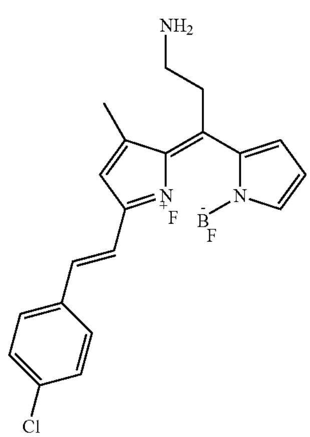 | 385.3 | 365.9 | 4.46 | 90% | 556 | 567 | 0.32 | 6.2 |

TABLE 1-continued

Chemical structures and characterization data for the BDM library.

| Code | Structure | Mcalc. | Mexp. | tR (min) | purity | λmax (ABS) | λmax (EM) | φ | mg |
|---|---|---|---|---|---|---|---|---|---|
| BDM-14 | 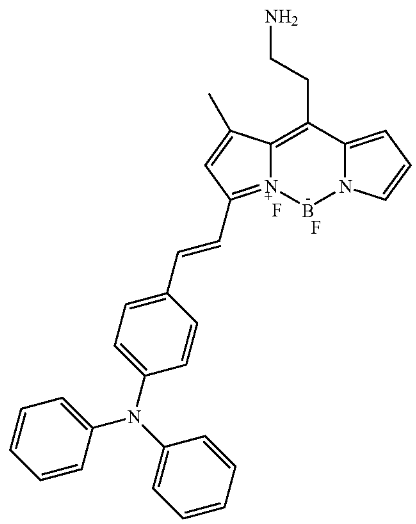 | 518.3 | 498.9 | 6.18 | 96% | 593 | 624 | 0.02 | 7.8 |
| BDM-16 | 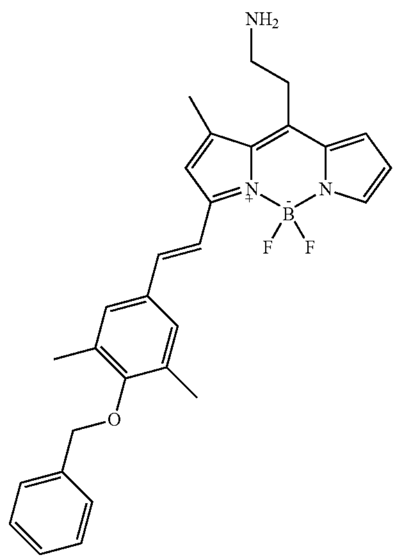 | 485.4 | 466.0 | 5.46 | 94% | 561 | 574 | 0.14 | 4.9 |
| BDM-18 | 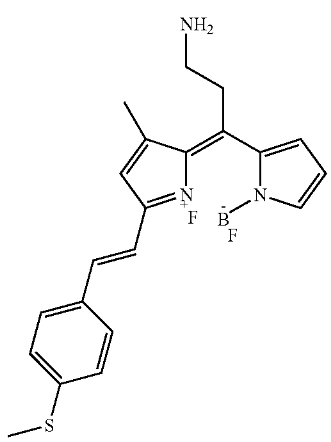 | 397.3 | 378.0 | 4.61 | 100% | 567 | 588 | 0.33 | 6.7 |

TABLE 1-continued

Chemical structures and characterization data for the BDM library.

| Code | Structure | Mcalc. | Mexp. | tR (min) | purity | λmax (ABS) | λmax (EM) | φ | mg |
|---|---|---|---|---|---|---|---|---|---|
| BDM-19 | 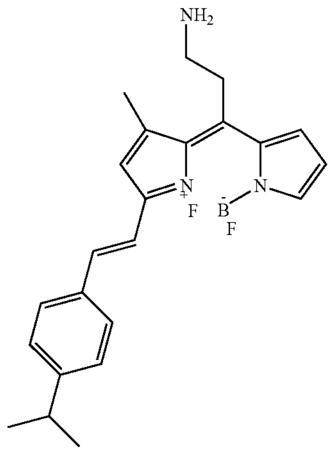 | 393.3 | 374.0 | 4.91 | 90% | 555 | 569 | 0.71 | 8.0 |
| BDM-22 | 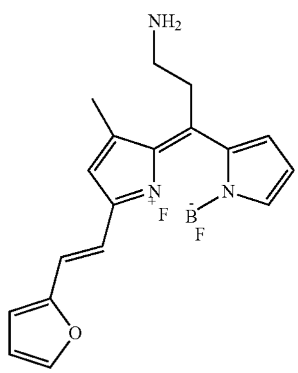 | 341.3 | 322.0 | 3.61 | 85% | 567 | 584 | 0.14 | 5.8 |
| BDM-30 | 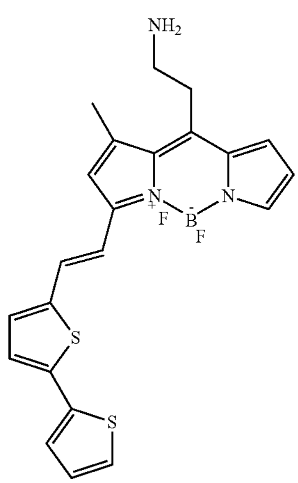 | 439.3 | 419.9 | 4.99 | 86% | 596 | 634 | 0.11 | 4.4 |

TABLE 1-continued

Chemical structures and characterization data for the BDM library.

| Code | Structure | Mcalc. | Mexp. | tR (min) | purity | λmax (ABS) | λmax (EM) | φ | mg |
|---|---|---|---|---|---|---|---|---|---|
| BDM-32 | 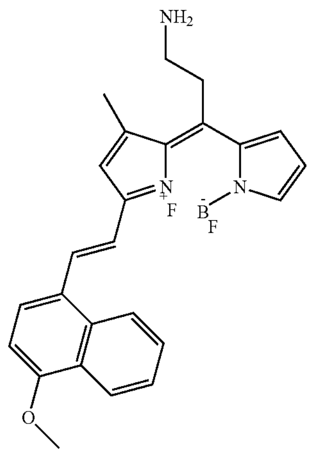 | 431.3 | 412.0 | 4.62 | 91% | 576 | 624 | 0.25 | 5.6 |
| BDM-33 | 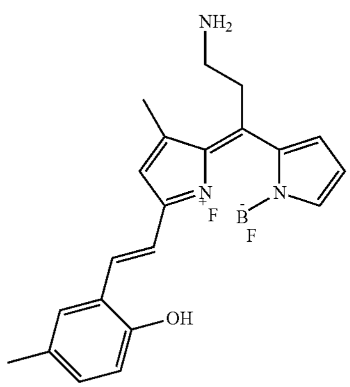 | 381.3 | 362.0 | 3.69 | 88% | 564 | 580 | 0.14 | 9.7 |
| BDM-34 | 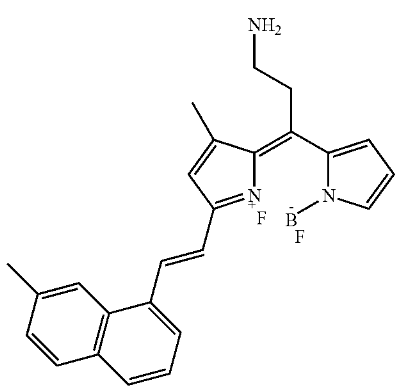 | 415.3 | 396.0 | 4.98 | 92% | 547 | 581 | 0.65 | 7.4 |

TABLE 1-continued

Chemical structures and characterization data for the BDM library.

| Code | Structure | Mcalc. | Mexp. | tR (min) | purity | λmax (ABS) | λmax (EM) | φ | mg |
| --- | --- | --- | --- | --- | --- | --- | --- | --- | --- |
| BDM-36 | | 415.3 | 396.0 | 5.02 | 94% | 568 | 595 | 0.23 | 6.9 |
| BDM-38 | | 432.3 | 411.9 | 3.71 | 87% | 565 | 579 | 0.06 | 9.8 |
| BDM-40 | | 427.3 | 408.0 | 4.94 | 88% | 554 | 567 | 0.53 | 5.6 |

TABLE 1-continued

Chemical structures and characterization data for the BDM library.

| Code | Structure | Mcalc. | Mexp. | tR (min) | purity | λmax (ABS) | λmax (EM) | φ | mg |
|---|---|---|---|---|---|---|---|---|---|
| BDM-42 | 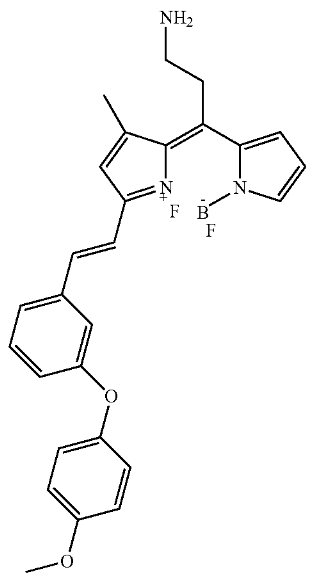 | 473.3 | 454.0 | 5.06 | 93% | 554 | 563 | 0.25 | 4.3 |
| BDM-43 | 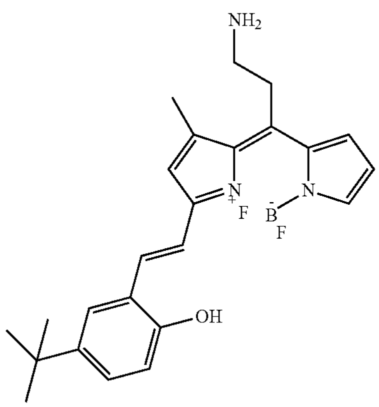 | 423.3 | 404.0 | 4.55 | 97% | 564 | 579 | 0.21 | 4.5 |
| BDM-45 | 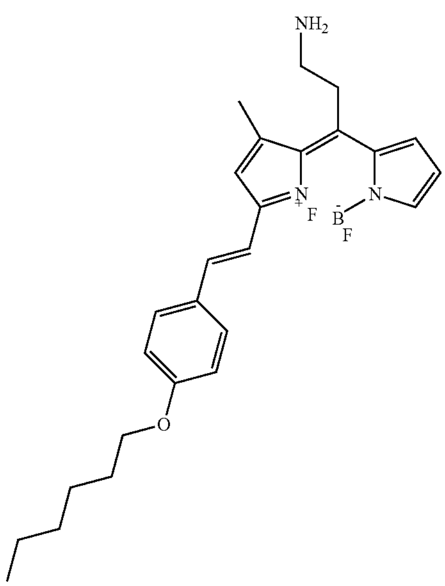 | 451.3 | 432.0 | 5.47 | 93% | 564 | 583 | 0.74 | 4.5 |

TABLE 1-continued

Chemical structures and characterization data for the BDM library.

| Code | Structure | Mcalc. | Mexp. | tR (min) | purity | λmax (ABS) | λmax (EM) | φ | mg |
|---|---|---|---|---|---|---|---|---|---|
| BDM-46 | 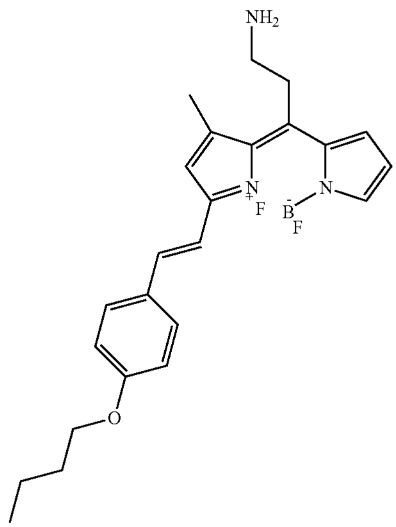 | 423.3 | 404.0 | 5.30 | 94% | 564 | 583 | 0.53 | 6.0 |
| BDM-48 | 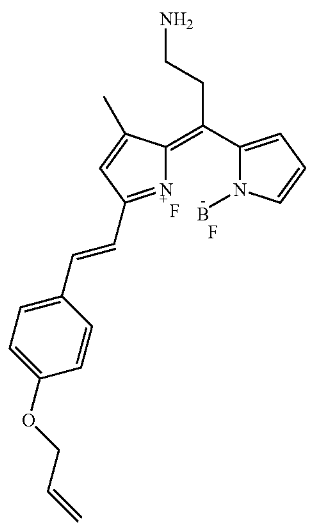 | 407.3 | 388.0 | 4.46 | 98% | 563 | 583 | 0.83 | 4.0 |
| BDM-49 | 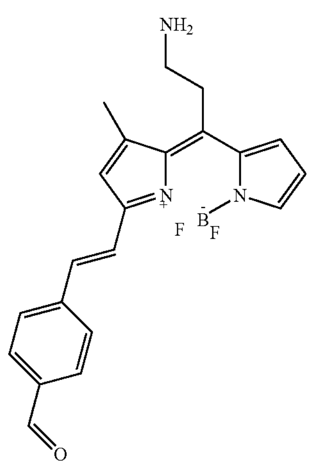 | 379.2 | 360.0 | 3.76 | 92% | 562 | 572 | 0.24 | 5.7 |

TABLE 1-continued

Chemical structures and characterization data for the BDM library.

| Code | Structure | Mcalc. | Mexp. | tR (min) | purity | λmax (ABS) | λmax (EM) | φ | mg |
|---|---|---|---|---|---|---|---|---|---|
| BDM-53 | 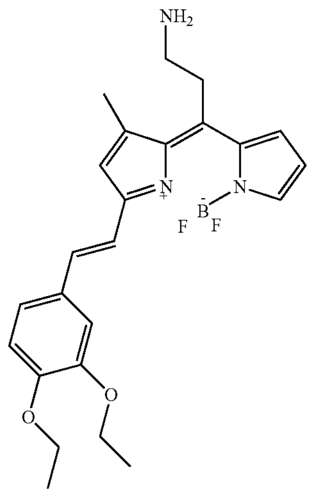 | 439.3 | 420.0 | 4.07 | 87% | 568 | 600 | 0.46 | 5.9 |
| BDM-54 | 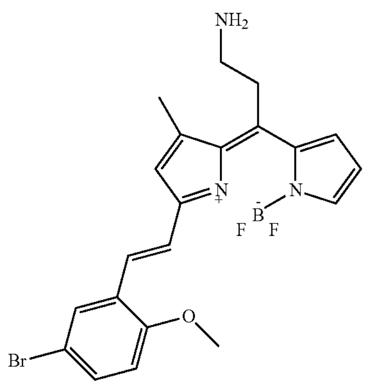 | 460.3 | 439.9 441.9 | 4.39 | 88% | 559 | 573 | 0.52 | 6.2 |
| BDM-61 | 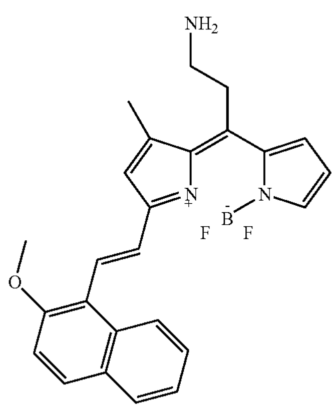 | 431.3 | 411.9 | 4.73 | 91% | 576 | 610 | 0.22 | 8.7 |

TABLE 1-continued

Chemical structures and characterization data for the BDM library.

| Code | Structure | Mcalc. | Mexp. | tR (min) | purity | λmax (ABS) | λmax (EM) | φ | mg |
|---|---|---|---|---|---|---|---|---|---|
| BDM-62 | 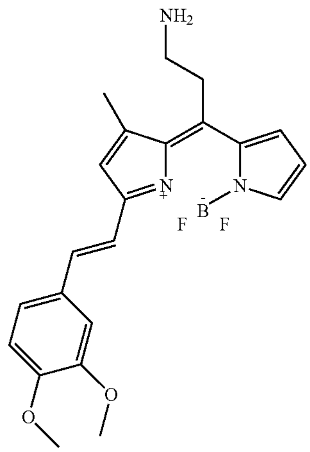 | 411.3 | 392.0 | 3.58 | 89% | 567 | 594 | 0.43 | |
| BDM-63 | 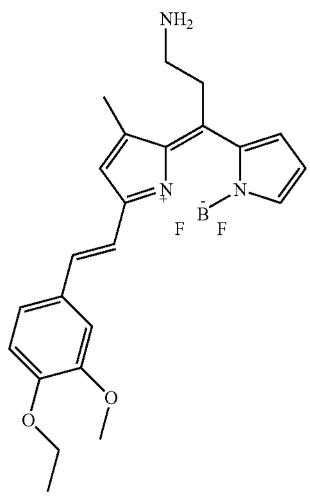 | 425.3 | 406.0 | 4.01 | 94% | 568 | 597 | 0.54 | 6.5 |
| BDM-65 | 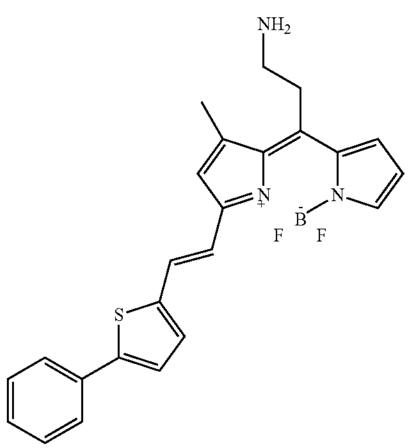 | 433.3 | 413.9 | 5.21 | 84% | 589 | 615 | 0.15 | 7.2 |

TABLE 1-continued
Chemical structures and characterization data for the BDM library.
| Code | Structure | Mcalc. | Mexp. | tR (min) | purity | λmax (ABS) | λmax (EM) | φ | mg |
|------|-----------|--------|-------|----------|--------|------------|-----------|---|-----|
| BDM-68 | 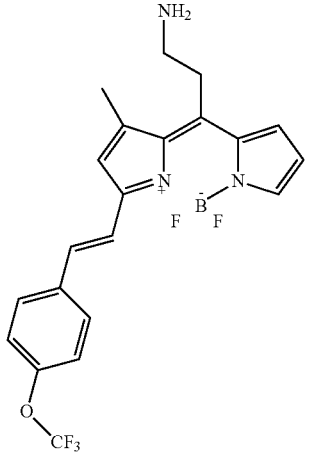 | 435.3 | 415.9 | 4.90 | 87% | 551 | 561 | 0.63 | 5.5 |
| BDM-69 | 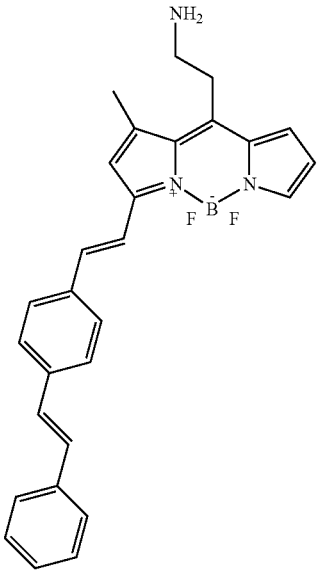 | 453.3 | 434.2 | 5.01 | 94% | 574 | 594 | 0.32 | 8.6 |
| BDM-70 | 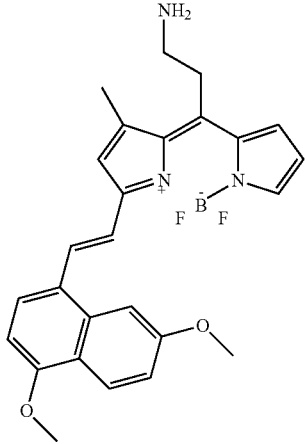 | 461.3 | 442.0 | 4.82 | 93% | 582 | 642 | 0.13 | 7.1 |

TABLE 1-continued
Chemical structures and characterization data for the BDM library.
| Code | Structure | Mcalc. | Mexp. | tR (min) | purity | λmax (ABS) | λmax (EM) | φ | mg |
|---|---|---|---|---|---|---|---|---|---|
| BDM-73 | 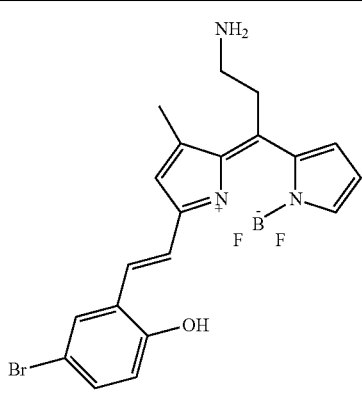 | 446.3 | 425.8 427.8 | 3.89 | 84% | 561 | 575 | 0.28 | 4.4 |
| BDM-75 | 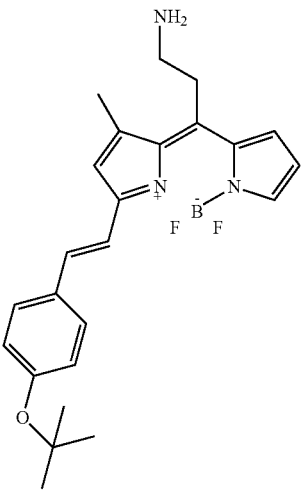 | 423.3 | 404.0 | 4.64 | 88% | 560 | 585 | 0.53 | 4.4 |
| BDM-76 | 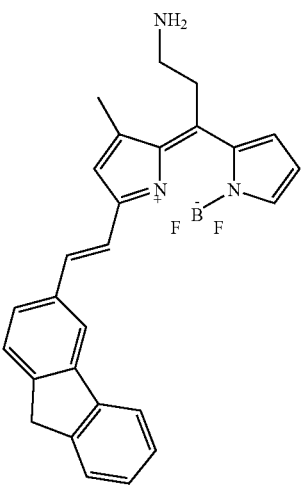 | 439.3 | 420.0 | 5.20 | 84% | 572 | 588 | 0.25 | 4.0 |

TABLE 1-continued

Chemical structures and characterization data for the BDM library.

| Code | Structure | Mcalc. | Mexp. | tR (min) | purity | λmax (ABS) | λmax (EM) | φ | mg |
|---|---|---|---|---|---|---|---|---|---|
| BDM-77 | 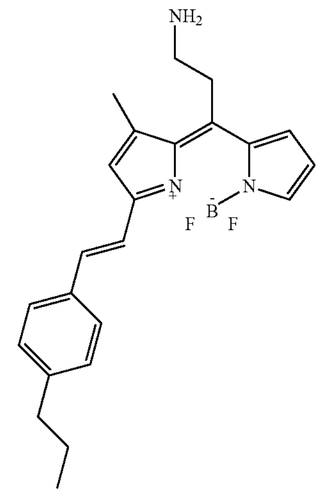 | 393.3 | 374.0 | 5.03 | 84% | 557 | 569 | 0.54 | 5.2 |
| BDM-78 | 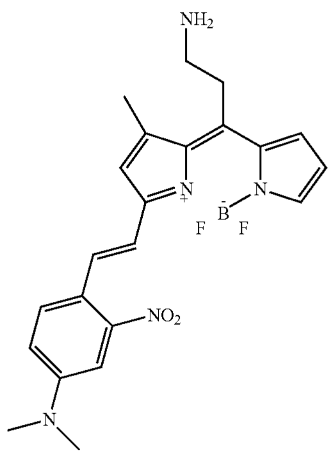 | 439.3 | 420.0 | 4.55 | 87% | 591 | n.d | 0.01 | 5.0 |
| BDM-88 | 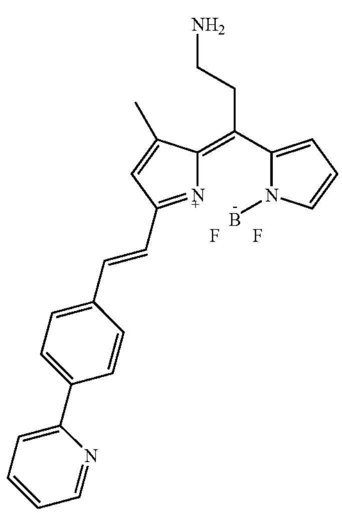 | 428.3 | 409.0 429.0 | 3.57 | 95% | 565 | 576 | 0.21 | 4.9 |

TABLE 1-continued

Chemical structures and characterization data for the BDM library.

| Code | Structure | Mcalc. | Mexp. | tR (min) | purity | λmax (ABS) | λmax (EM) | φ | mg |
|---|---|---|---|---|---|---|---|---|---|
| BDM-90 | 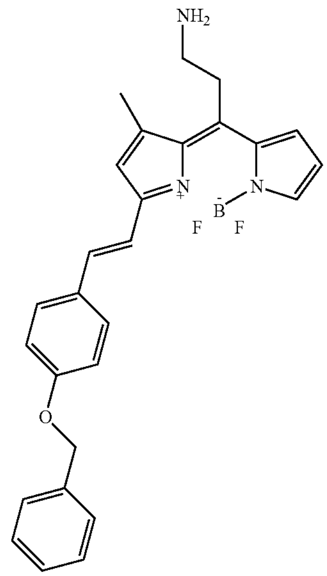 | 457.3 | 438.0 | 5.18 | 97% | 565 | 582 | 0.26 | 7.3 |
| BDM-91 | 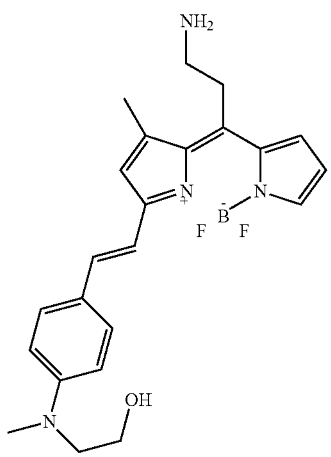 | 424.3 | 405.0 | 3.59 | 95% | 614 | 699 | 0.02 | 7.0 |
| BDM-93 | 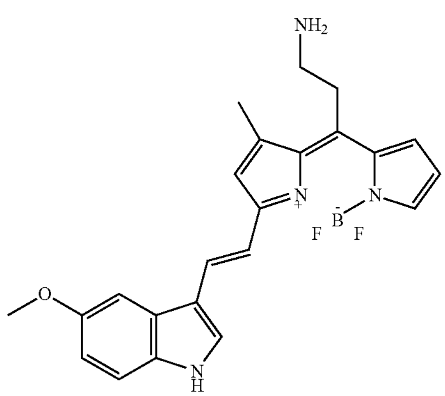 | 420.3 | 401.0 | 3.95 | 91% | 592 | 653 | 0.06 | 4.0 |

TABLE 1-continued
Chemical structures and characterization data for the BDM library.
| Code | Structure | Mcalc. | Mexp. | tR (min) | purity | λmax (ABS) | λmax (EM) | φ | mg |
|---|---|---|---|---|---|---|---|---|---|
| BDM-97 | 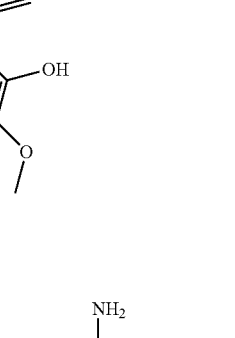 | 397.3 | 378.0 | 3.68 | 89% | 561 | 572 | 0.04 | 6.8 |
| BDM-107 | 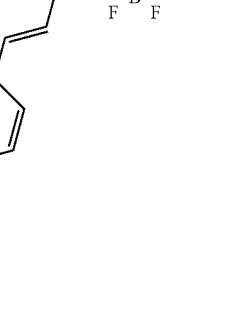 | 422.3 | 403.0 | 4.22 | 97% | 617 | 681 | 0.05 | 4.7 |
| BDM-108 | 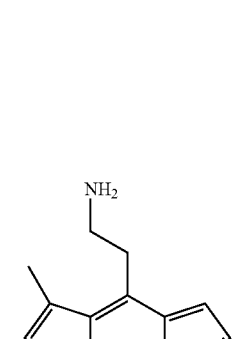 | 393.3 | 374.1 | 4.86 | 85% | 549 | 573 | 0.35 | 6.2 |

TABLE 1-continued
Chemical structures and characterization data for the BDM library.
| Code | Structure | Mcalc. | Mexp. | tR (min) | purity | λmax (ABS) | λmax (EM) | φ | mg |
|---|---|---|---|---|---|---|---|---|---|
| BDM-110 | 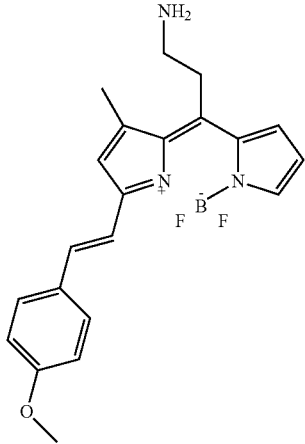 | 381.3 | 362.0 | 4.11 | 91% | 563 | 583 | 0.85 | 3.5 |
| BDM-111 | 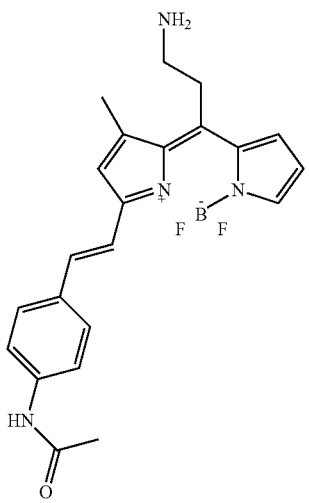 | 408.3 | 389.0 | 3.11 | 100% | 566 | 589 | 0.79 | 4.7 |
| BDM-132 | 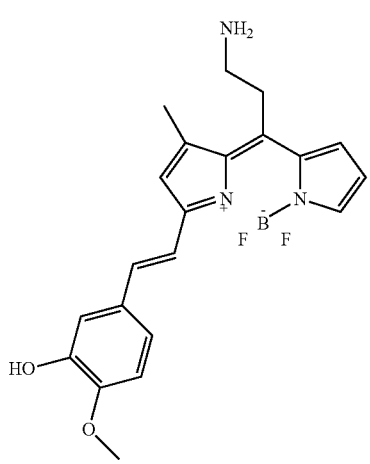 | 397.3 | 378.0 | 3.36 | 100% | 568 | 594 | 0.05 | 4.5 |

TABLE 1-continued

Chemical structures and characterization data for the BDM library.

| Code | Structure | Mcalc. | Mexp. | tR (min) | purity | λmax (ABS) | λmax (EM) | φ | mg |
|---|---|---|---|---|---|---|---|---|---|
| BDM-135 | 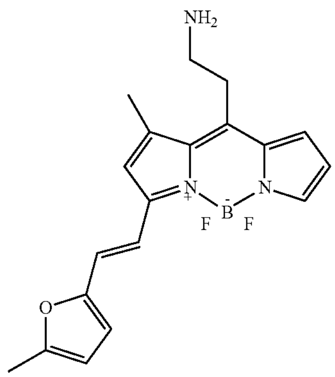 | 355.3 | 336.0 | 3.98 | 93% | 577 | 601 | 0.10 | 4.4 |
| BDM-137 | 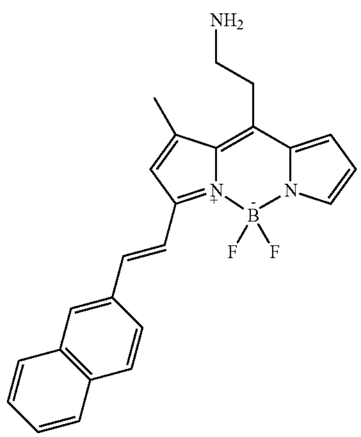 | 401.3 | 382.0 | 4.84 | 87% | 563 | 575 | 0.28 | 7.1 |
| BDM-139 | 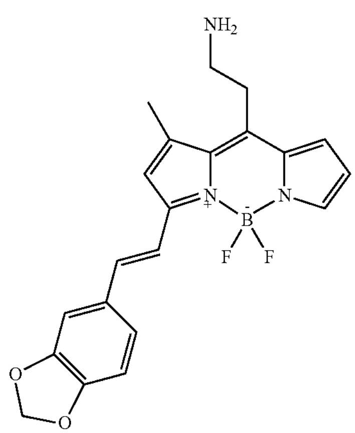 | 395.2 | 376.0 | 3.94 | 92% | 564 | 584 | 0.55 | 3.7 |

TABLE 1-continued

Chemical structures and characterization data for the BDM library.

| Code | Structure | Mcalc. | Mexp. | tR (min) | purity | λmax (ABS) | λmax (EM) | φ | mg |
|---|---|---|---|---|---|---|---|---|---|
| BDM-140 | 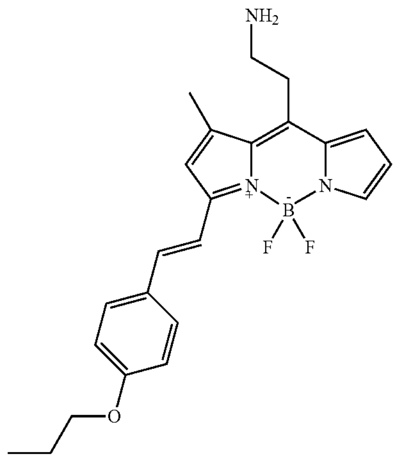 | 409.3 | 390.0 | 4.97 | 93% | 564 | 585 | 0.57 | 5.6 |
| BDM-143 | 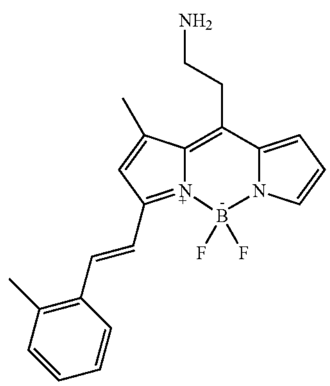 | 365.2 | 346.0 | 4.51 | 84% | 554 | 566 | 0.42 | 6.1 |
| BDM-144 | 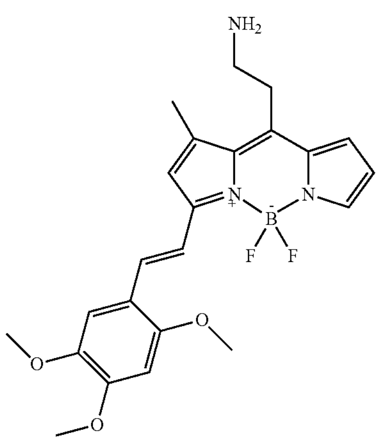 | 441.3 | 422.0 | 3.67 | 94% | 578 | 612 | 0.05 | 5.4 |

TABLE 1-continued
Chemical structures and characterization data for the BDM library.
| Code | Structure | Mcalc. | Mexp. | tR (min) | purity | λmax (ABS) | λmax (EM) | φ | mg |
|---|---|---|---|---|---|---|---|---|---|
| BDM-177 | 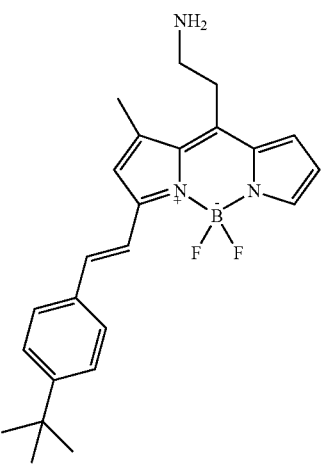 | 407.3 | 388.0 | 5.03 | 96% | 556 | 567 | 0.78 | 4.1 |
| BDM-178 | 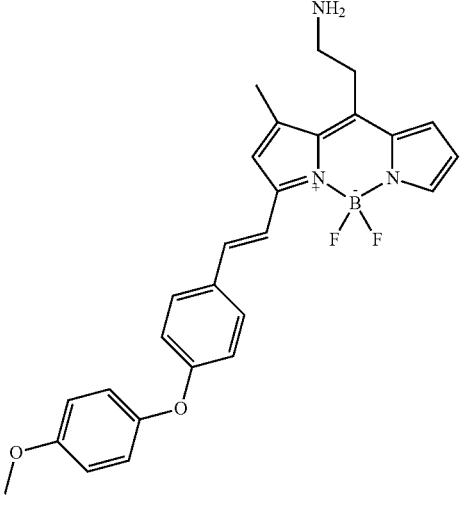 | 473.2 | 454.0 | 5.06 | 96% | 561 | 577 | 0.37 | 5.0 |
| BDM-186 | 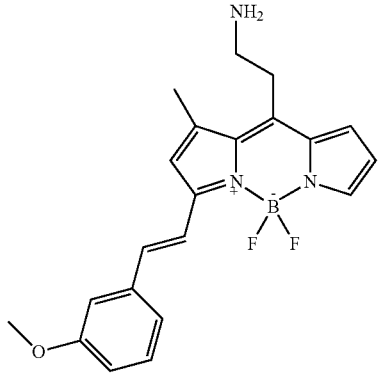 | 381.2 | 362.0 | 4.15 | 97% | 553 | 564 | 0.97 | 5.4 |

TABLE 1-continued

Chemical structures and characterization data for the BDM library.

| Code | Structure | Mcalc. | Mexp. | tR (min) | purity | λmax (ABS) | λmax (EM) | φ | mg |
|------|-----------|--------|-------|----------|--------|------------|-----------|---|-----|
| BDM-192 | 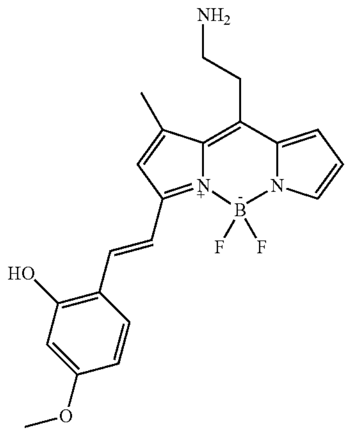 | 397.2 | 378.0 | 3.75 | 86% | 574 | 605 | 0.20 | 4.0 |
| BDM-195 | 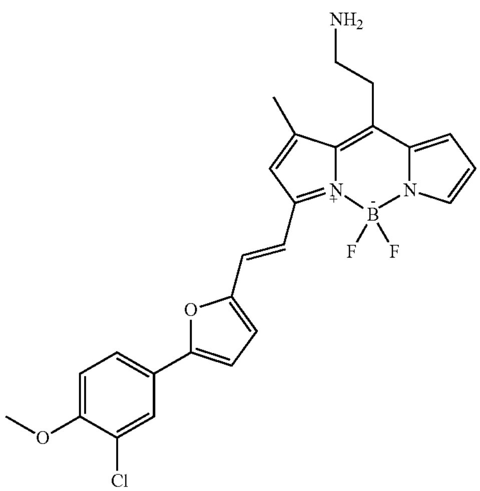 | 481.7 | 461.9 | 5.18 | 100% | 600 | 663 | 0.03 | 6.5 |
| BDM-101 | 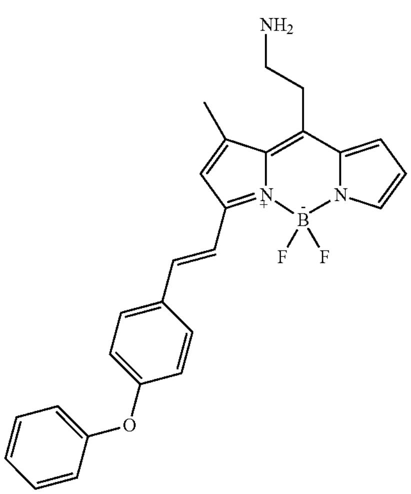 | 443.3 | 423.9 | 5.23 | 97% | 559 | 576 | 0.66 | 5.3 |

TABLE 1-continued

Chemical structures and characterization data for the BDM library.

| Code | Structure | Mcalc. | Mexp. | tR (min) | purity | λmax (ABS) | λmax (EM) | φ | mg |
|---|---|---|---|---|---|---|---|---|---|
| BDM-100 | 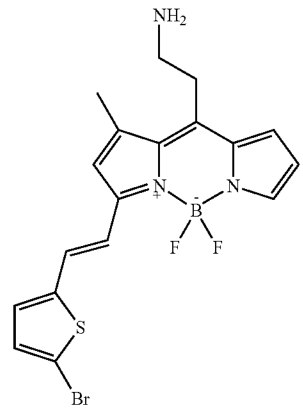 | 436.1 | 415.8 417.8 | 4.49 | 86% | 571 | 582 | 0.43 | 5.0 |
| BDM-20 | 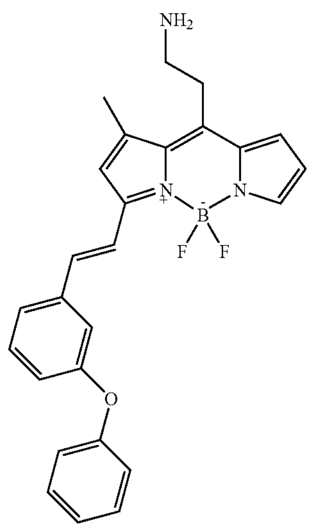 | 443.3 | 424.0 | 5.09 | 94% | 554 | 564 | 0.47 | 4.4 |
| BDM-202 | 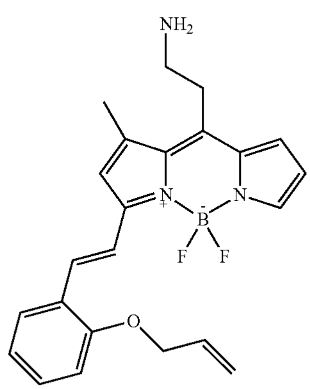 | 407.3 | 388.0 | 4.64 | 85% | 559 | 575 | 0.52 | 4.1 |

TABLE 1-continued
Chemical structures and characterization data for the BDM library.
| Code | Structure | Mcalc. | Mexp. | tR (min) | purity | λmax (ABS) | λmax (EM) | φ | mg |
|---|---|---|---|---|---|---|---|---|---|
| BDM-231 | 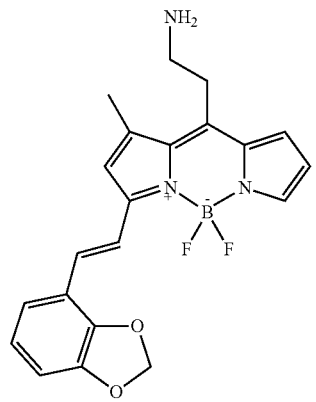 | 395.2 | 376.0 | 3.94 | 93% | 558 | 568 | 0.17 | 5.9 |
| BDM-198 | 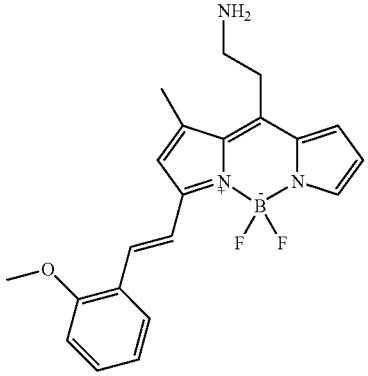 | 381.2 | 362.0 | 4.08 | 95% | 559 | 574 | 0.59 | 5.2 |
| BDM-218 | 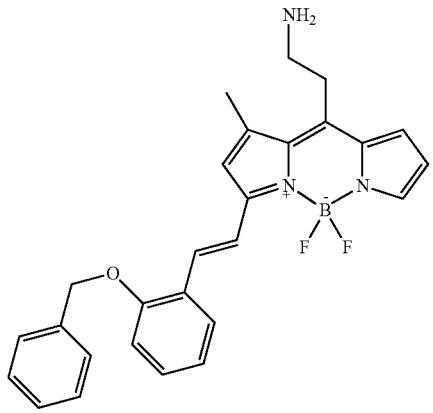 | 457.3 | 438.0 | 5.18 | 100% | 559 | 574 | 0.37 | 5.8 |

TABLE 1-continued

Chemical structures and characterization data for the BDM library.

| Code | Structure | Mcalc. | Mexp. | tR (min) | purity | λmax (ABS) | λmax (EM) | φ | mg |
|---|---|---|---|---|---|---|---|---|---|
| BDM-179 | 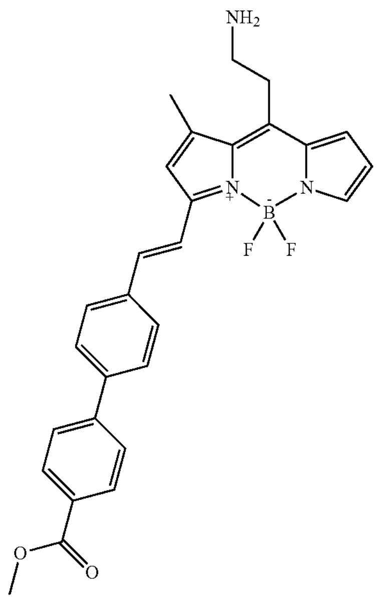 | 485.3 | 466.0 | 5.09 | 96% | 566 | 581 | 0.26 | 5.5 |
| BDM-199 | 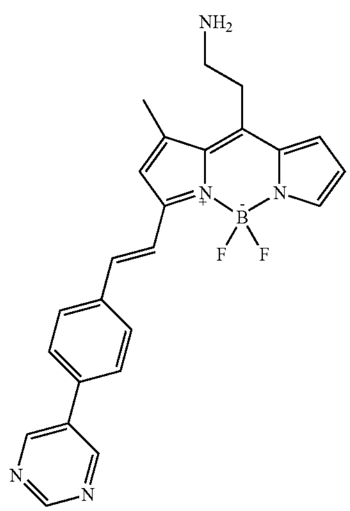 | 429.3 | 410.0 | 3.79 | 94% | 562 | 574 | 0.18 | 7.6 |
| BDM-207 | 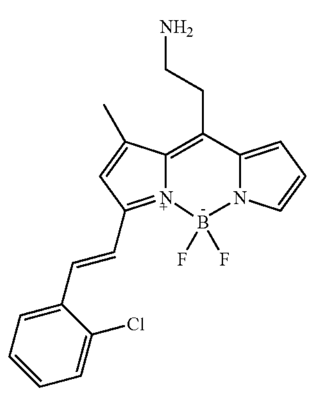 | 385.7 | 366.0 | 4.47 | 88% | 553 | 566 | 0.24 | 3.9 |

TABLE 1-continued

Chemical structures and characterization data for the BDM library.

| Code | Structure | Mcalc. | Mexp. | tR (min) | purity | λmax (ABS) | λmax (EM) | φ | mg |
|---|---|---|---|---|---|---|---|---|---|
| BDM-209 | 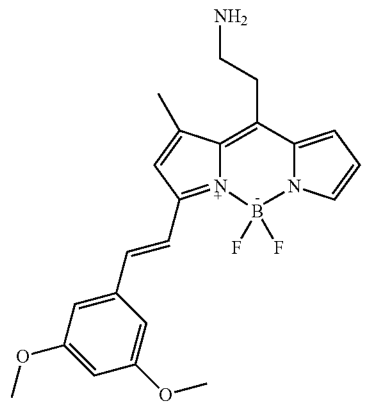 | 411.3 | 392.0 | 4.09 | 93% | 555 | 567 | 0.38 | 4.1 |
| BDM-237 | 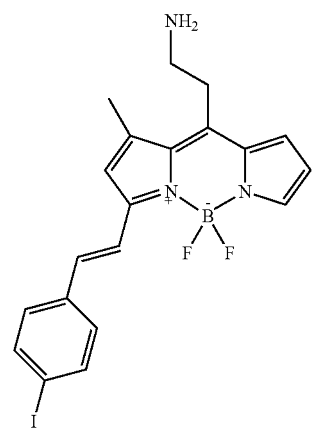 | 477.1 | 457.8 | 4.69 | 97% | 558 | 572 | 0.35 | 5.2 |
| BDM-228 | 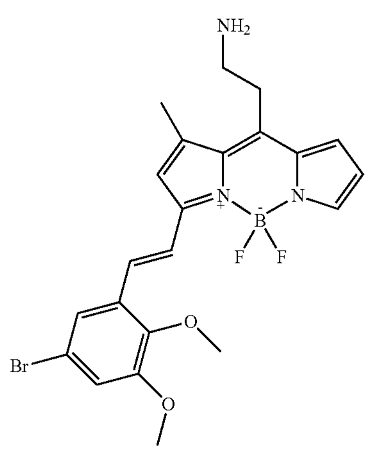 | 490.2 | 469.8<br>471.9 | 4.48 | 92% | 557 | 567 | 0.24 | 8.8 |

TABLE 1-continued
Chemical structures and characterization data for the BDM library.
| Code | Structure | Mcalc. | Mexp. | tR (min) | purity | λmax (ABS) | λmax (EM) | φ | mg |
|---|---|---|---|---|---|---|---|---|---|
| BDM-236 | 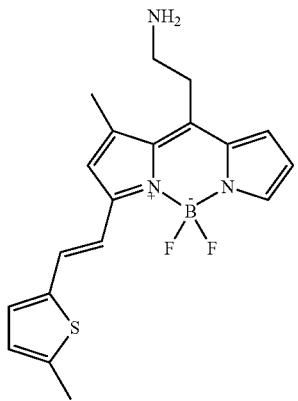 | 371.3 | 352.0 | 4.29 | 90% | 574 | 594 | 0.22 | 4.9 |
| BDM-208 | 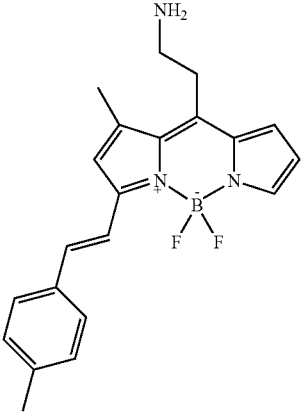 | 365.2 | 346.1 | 4.54 | 100% | 558 | 572 | 0.27 | 3.8 |
| BDM-27 | 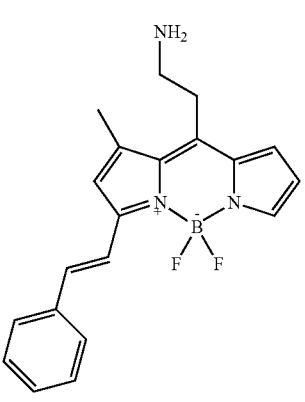 | 351.2 | 332.0 | 4.01 | 87% | 553 | 566 | 0.39 | 4.2 |

TABLE 1-continued

Chemical structures and characterization data for the BDM library.

| Code | Structure | Mcalc. | Mexp. | tR (min) | purity | λmax (ABS) | λmax (EM) | φ | mg |
|---|---|---|---|---|---|---|---|---|---|
| BDM-37 | 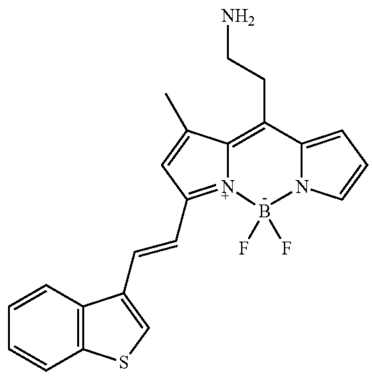 | 407.3 | 387.9 | 4.81 | 84% | 566 | 588 | 0.15 | 4.5 |
| BDM-163 | 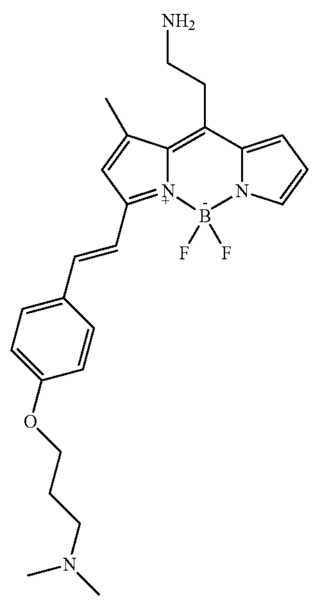 | 452.4 | 453.0 | 2.78 | 88% | 566 | 586 | 0.41 | 5.6 |
| BDM-239 | 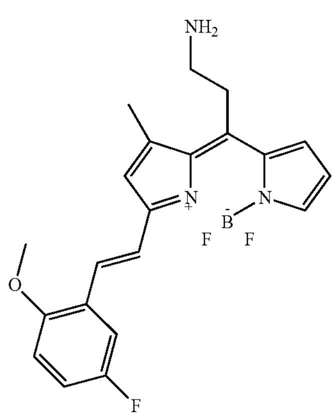 | 399.2 | 380.0 | 4.42 | 100% | 559 | 572 | 0.28 | 5.5 |

TABLE 1-continued

Chemical structures and characterization data for the BDM library.

| Code | Structure | Mcalc. | Mexp. | tR (min) | purity | λmax (ABS) | λmax (EM) | φ | mg |
|---|---|---|---|---|---|---|---|---|---|
| BDM-240 | 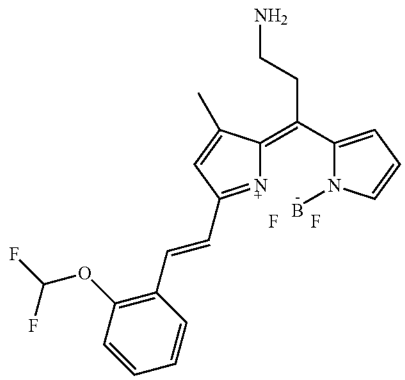 | 417.2 | 397.9 | 4.48 | 87% | 552 | 565 | 0.23 | 5.5 |
| BDM-241 | 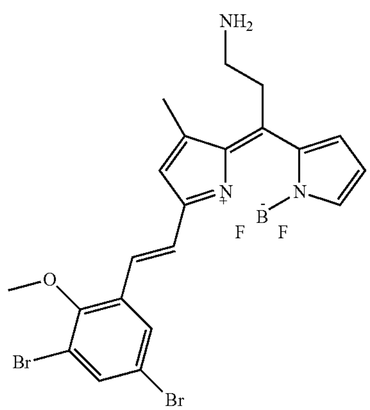 | 539.0 | 517.8 | 4.88 | 84% | 560 | 576 | 0.32 | 6.5 |
| BDM-243 | 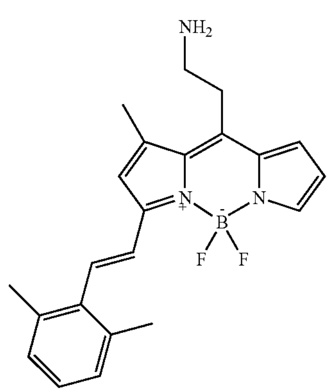 | 379.3 | 360.0 | 4.72 | 89% | 543 | 565 | 0.87 | 3.0 |

TABLE 1-continued

Chemical structures and characterization data for the BDM library.

| Code | Structure | Mcalc. | Mexp. | tR (min) | purity | λmax (ABS) | λmax (EM) | φ | mg |
|---|---|---|---|---|---|---|---|---|---|
| BDM-245 | 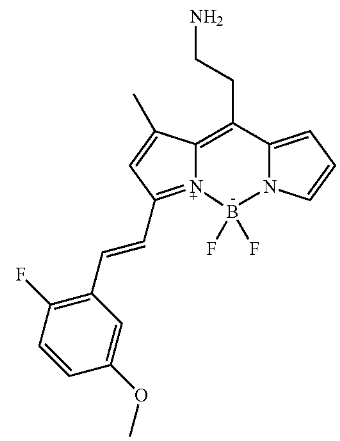 | 399.2 | 380.0 | 4.32 | 87% | 555 | 563 | 0.32 | 4.4 |
| BDM-246 | 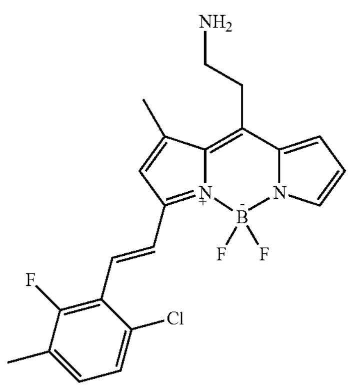 | 417.7 | 397.9 | 4.93 | 100% | 554 | 566 | 0.17 | 5.8 |
| BDM-247 | 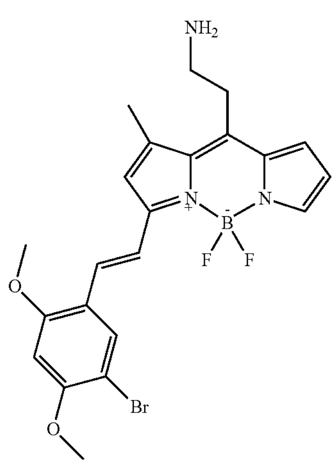 | 490.2 | 469.9<br>471.9 | 4.48<br>4.67 | 90% | 571 | 599 | 0.54 | 5.6 |

TABLE 1-continued

Chemical structures and characterization data for the BDM library.

| Code | Structure | Mcalc. | Mexp. | tR (min) | purity | λmax (ABS) | λmax (EM) | φ | mg |
|---|---|---|---|---|---|---|---|---|---|
| BDM-249 | 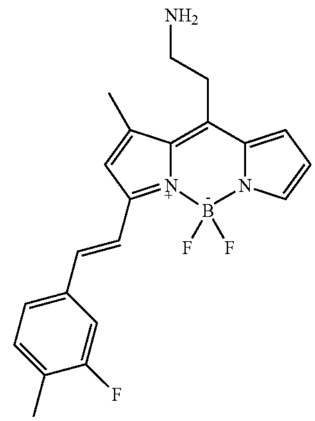 | 383.2 | 364.0 | 4.72 | 100% | 557 | 568 | 0.24 | 4.8 |
| BDM-251 | 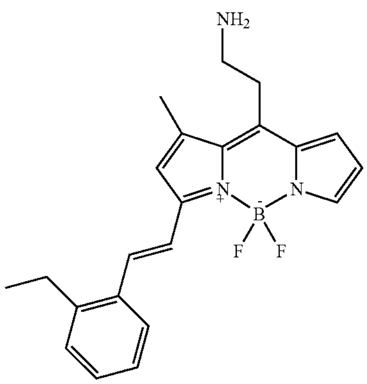 | 379.3 | 360.0 | 4.84 | 100% | 556 | 572 | 0.22 | 5.9 |
| BDM-252 | 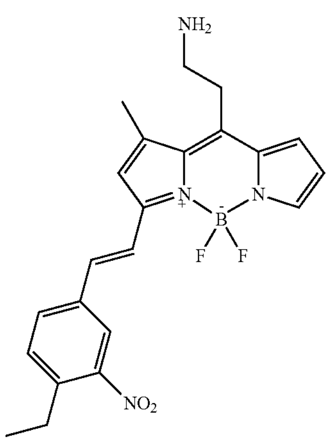 | 424.3 | 405.0 | 4.86 | 91% | 556 | 569 | 0.08 | 4.6 |

TABLE 1-continued

Chemical structures and characterization data for the BDM library.

| Code | Structure | Mcalc. | Mexp. | tR (min) | purity | λmax (ABS) | λmax (EM) | φ | mg |
|------|-----------|--------|-------|----------|--------|------------|-----------|---|-----|
| BDM-259 | 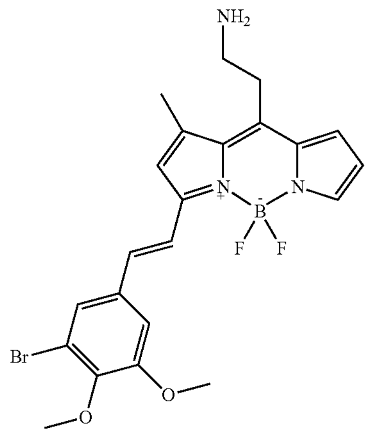 | 490.2 | 469.8 471.8 | 4.70 | 87% | 559 | 573 | 0.35 | 5.0 |
| BDM-260 | 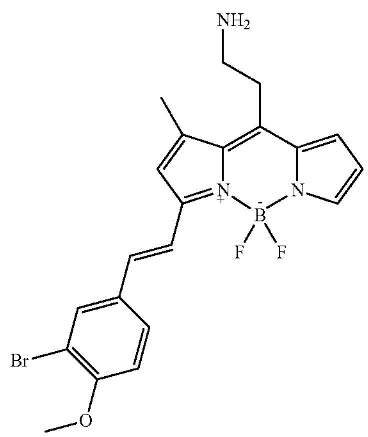 | 460.1 | 439.8 441.8 | 4.55 | 93%, | 564 | 582 | 0.05 | 4.0 |
| BDM-263 | 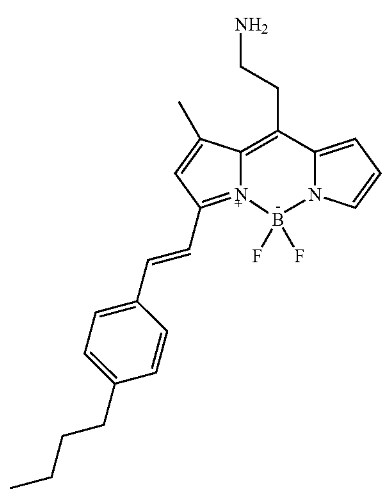 | 407.3 | 388.0 | 5.69 | 85% | 559 | 571 | 0.26 | 3.9 |

TABLE 1-continued
Chemical structures and characterization data for the BDM library.
| Code | Structure | Mcalc. | Mexp. | tR (min) | purity | λmax (ABS) | λmax (EM) | φ | mg |
|---|---|---|---|---|---|---|---|---|---|
| BDM-267 | 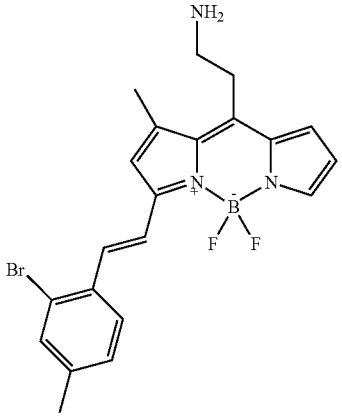 | 444.1 | 423.9 425.9 | 4.96 | 92% | 558 | 573 | 0.21 | |
| BDM-274 | 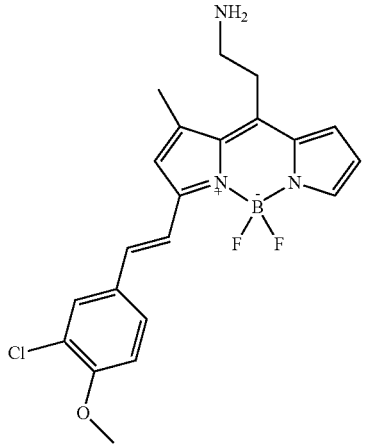 | 415.7 | 395.9 | 4.48 | 93% | 562 | 577 | 0.46 | 3.9 |
| BDM-275 | 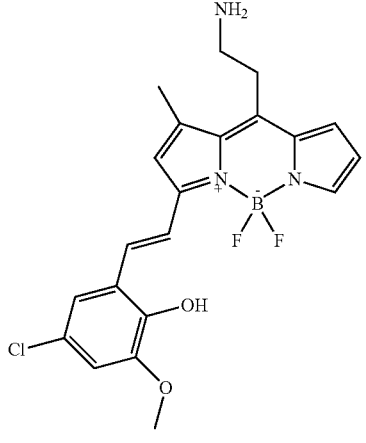 | 431.7 | 411.9 | 4.30 | 85% | 562 | n.d | 0.05 | 5.9 |

TABLE 1-continued

Chemical structures and characterization data for the BDM library.

| Code | Structure | Mcalc. | Mexp. | tR (min) | purity | λmax (ABS) | λmax (EM) | φ | mg |
|---|---|---|---|---|---|---|---|---|---|
| BDM-277 | 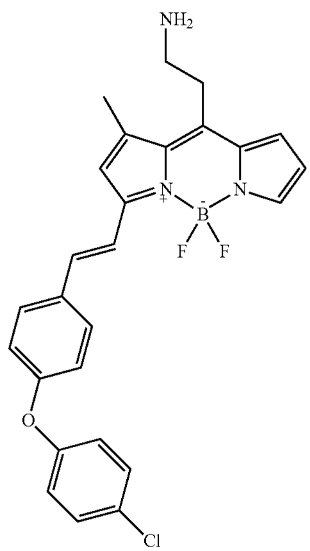 | 477.7 | 457.9 | 5.71 | 87% | 559 | 574 | 0.59 | 4.9 |
| BDM-281 | 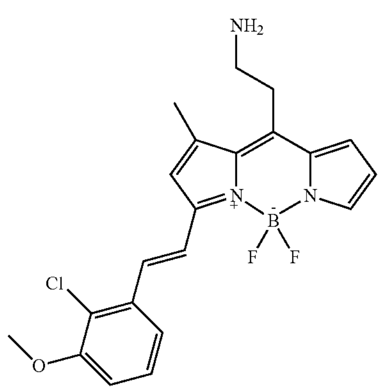 | 415.7 | 395.9 | 4.13 | 92% | 554 | 567 | 0.28 | 5.1 |
| BDM-282 | 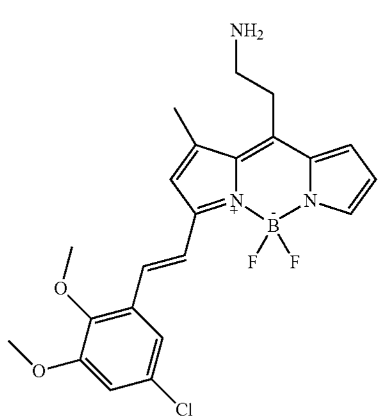 | 445.7 | 425.9 | 4.74 | 88% | 558 | 565 | 0.19 | 4.5 |

TABLE 1-continued

Chemical structures and characterization data for the BDM library.

| Code | Structure | Mcalc. | Mexp. | tR (min) | purity | λmax (ABS) | λmax (EM) | φ | mg |
|---|---|---|---|---|---|---|---|---|---|
| BDM-283 | 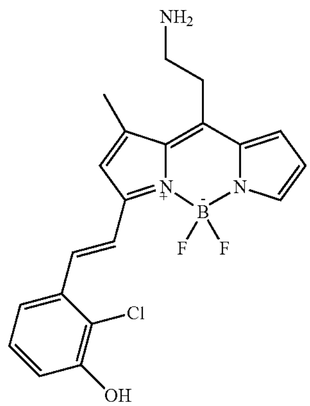 | 401.7 | 381.9 | 3.68 | 100% | 556 | 567 | 0.15 | 4.3 |
| BDM-284 | 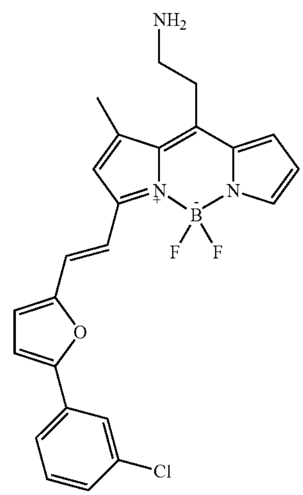 | 451.7 | 431.9 | 5.23 | 84% | 594 | 622 | 0.03 | 4.6 |
| BDM-285 | 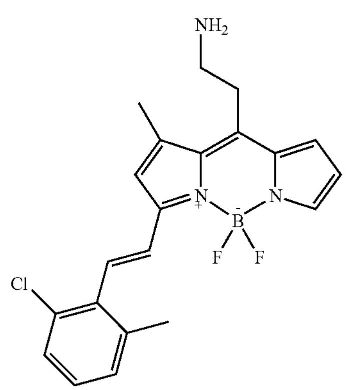 | 399.7 | 379.9 | 4.74 | 86% | 544 | 561 | 0.51 | 6.0 |

TABLE 1-continued

Chemical structures and characterization data for the BDM library.

| Code | Structure | Mcalc. | Mexp. | tR (min) | purity | λmax (ABS) | λmax (EM) | φ | mg |
|---|---|---|---|---|---|---|---|---|---|
| BDM-289 | 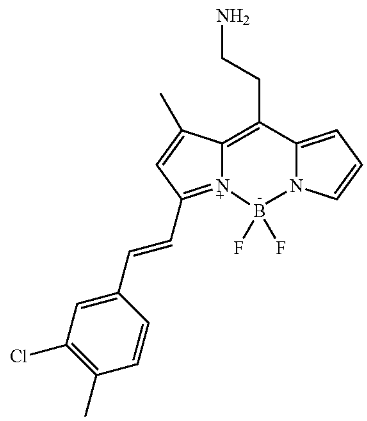 | 399.7 | 380.0 | 4.97 | 84% | 559 | 570 | 0.26 | 4.9 |
| BDM-290 | 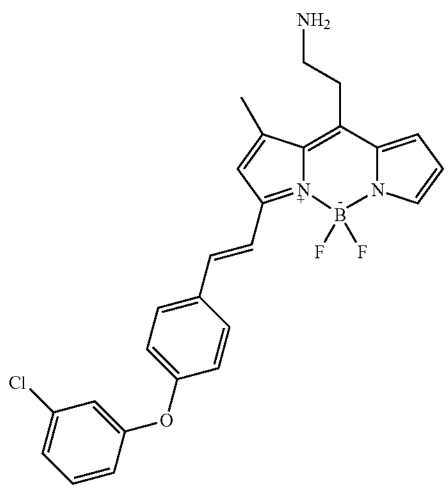 | 477.7 | 457.9 | 5.61 | 85% | 558 | 574 | 0.36 | 4.5 |
| BDM-298 | 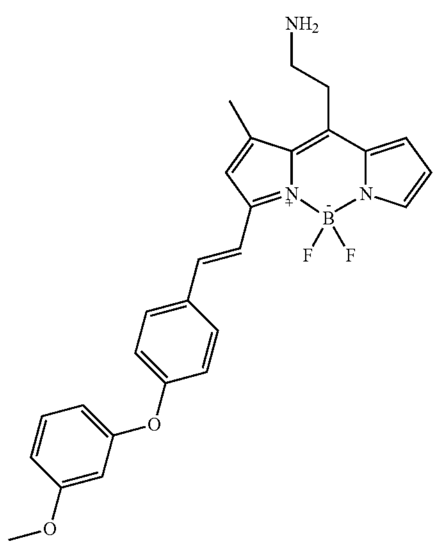 | 473.3 | 454.0 | 5.30 | 89% | 559 | 568 | 0.32 | 6.8 |

TABLE 1-continued
Chemical structures and characterization data for the BDM library.
| Code | Structure | Mcalc. | Mexp. | tR (min) | purity | λmax (ABS) | λmax (EM) | φ | mg |
|---|---|---|---|---|---|---|---|---|---|
| BDM-299 | 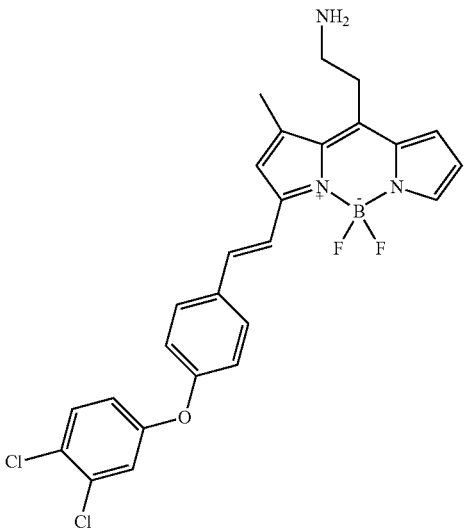 | 512.2 | 491.8 493.8 | 5.89 | 91% | 555 | 563 | 0.27 | 7.1 |
| BDM-300 | 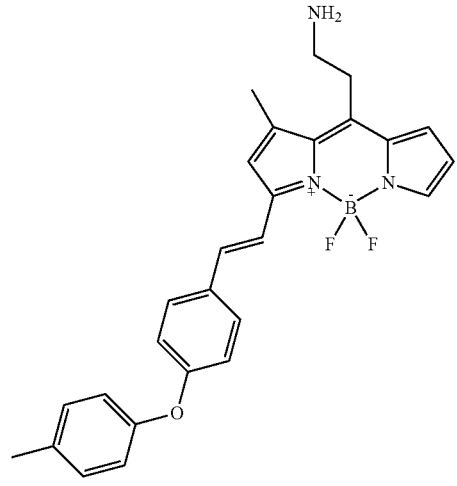 | 457.3 | 438.0 | 5.65 | 89% | 562 | 579 | 0.44 | 5.3 |
| BDM-301 | 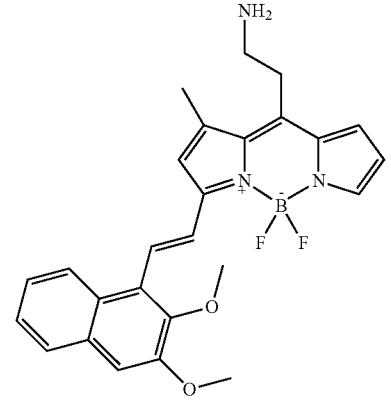 | 461.3 | 442.0 | 4.76 | 100% | 563 | 586 | 0.41 | 5.6 |

TABLE 1-continued

Chemical structures and characterization data for the BDM library.

| Code | Structure | Mcalc. | Mexp. | tR (min) | purity | λmax (ABS) | λmax (EM) | φ | mg |
|---|---|---|---|---|---|---|---|---|---|
| BDM-303 | 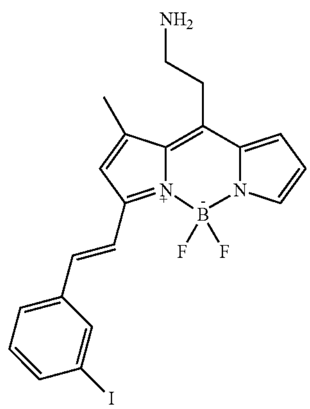 | 477.1 | 457.8 | 4.92 | 100% | 555 | 566 | 0.31 | 5.6 |
| BDM-305 | 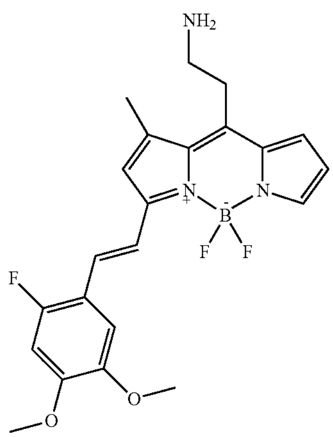 | 429.2 | 410.0 | 3.99 | 96% | 567 | 587 | 0.25 | 8.1 |
| BDM-307 | 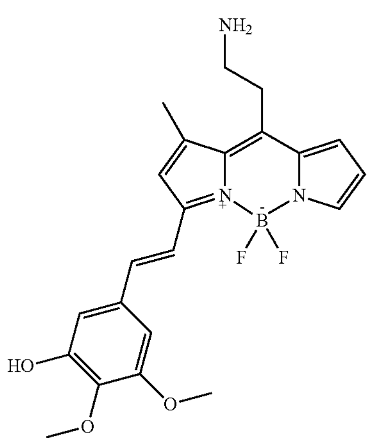 | 427.3 | 408.0 | 3.50 | 84% | 564 | 580 | 0.07 | 4.0 |

TABLE 1-continued

Chemical structures and characterization data for the BDM library.

| Code | Structure | Mcalc. | Mexp. | tR (min) | purity | λmax (ABS) | λmax (EM) | φ | mg |
|---|---|---|---|---|---|---|---|---|---|
| BDM-308 | 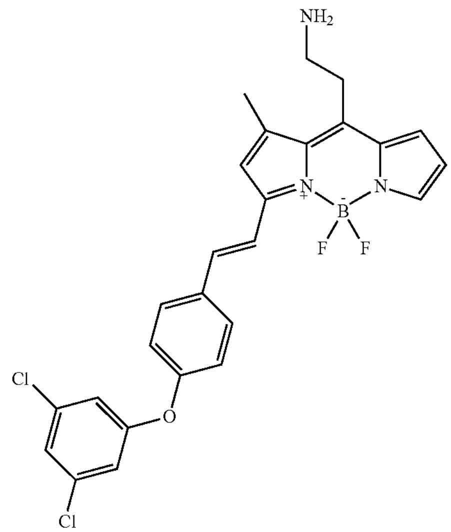 | 512.2 | 491.8 | 6.15 | 86% | 556 | 567 | 0.19 | 4.9 |
| BDM-310 | 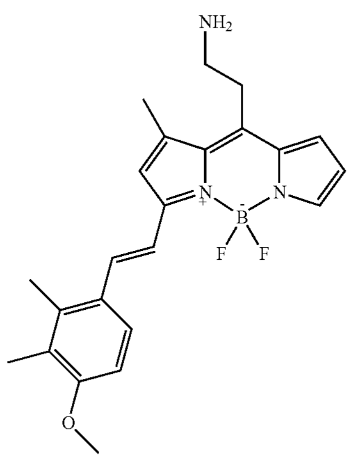 | 409.3 | 390.0 | 4.90 | 84% | 566 | 600 | 0.42 | 6.5 |
| BDM-311 | 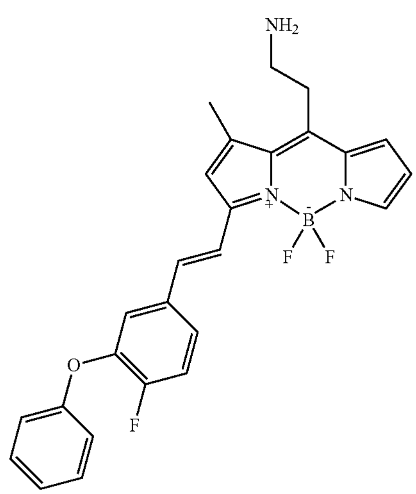 | 461.3 | 441.9 | 5.28 | 84% | 556 | 565 | 0.21 | 5.1 |

TABLE 1-continued
Chemical structures and characterization data for the BDM library.
| Code | Structure | Mcalc. | Mexp. | tR (min) | purity | λmax (ABS) | λmax (EM) | φ | mg |
|---|---|---|---|---|---|---|---|---|---|
| BDM-312 | 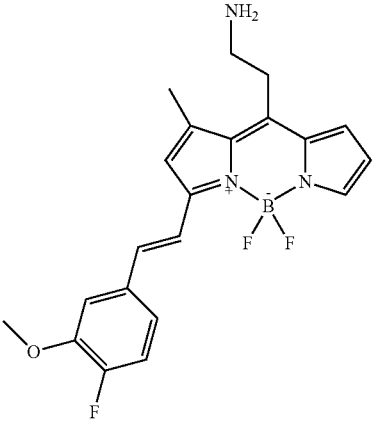 | 399.2 | 380.0 | 4.36 | 83% | 557 | 568 | 0.18 | 3.0 |
| BDM-314 | 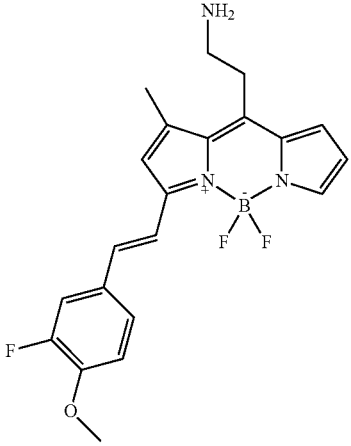 | 399.2 | 380.0 | 4.26 | 100% | 556 | 570 | 0.10 | 4.7 |
| BDM-316 | 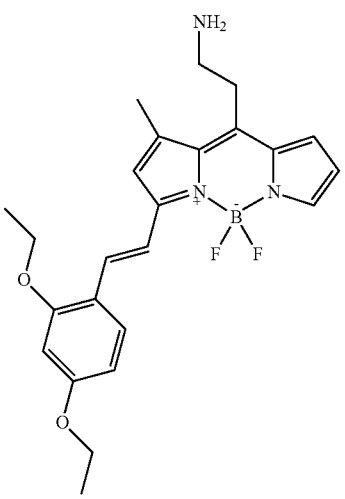 | 439.3 | 420.0 | 4.81 | 87%, 4.81 | 572 | 610 | 0.46 | 5.9 |

TABLE 1-continued

Chemical structures and characterization data for the BDM library.

| Code | Structure | Mcalc. | Mexp. | tR (min) | purity | λmax (ABS) | λmax (EM) | φ | mg |
|---|---|---|---|---|---|---|---|---|---|
| BDM-318 | 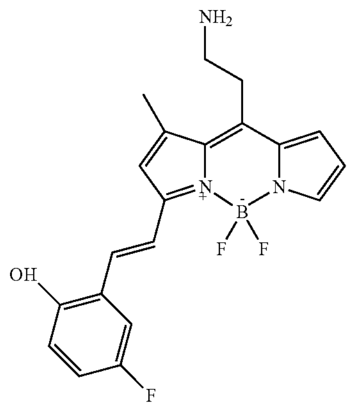 | 385.2 | 366.0 | 3.83 | 85%, 3.83 | 563 | 576 | 0.11 | 7.4 |
| BDM-320 | 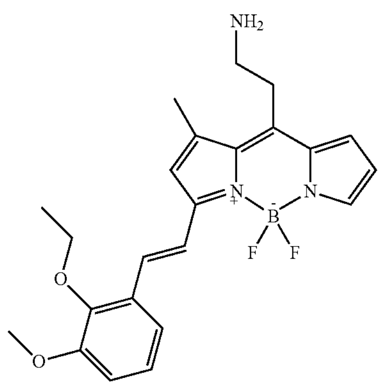 | 425.3 | 406.0 | 4.46 | 84% | 558 | 569 | 0.21 | 4.3 |
| BDM-322 | 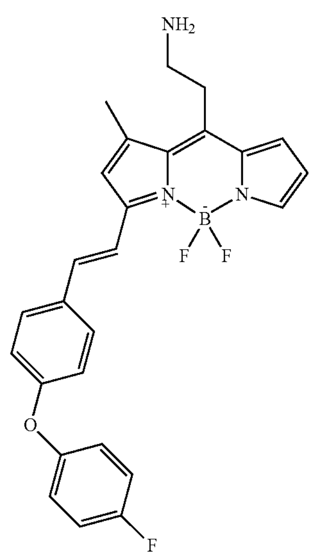 | 461.3 | 441.9 | 5.37 | 85% | 559 | 577 | 0.15 | 5.5 |

TABLE 1-continued

Chemical structures and characterization data for the BDM library.

| Code | Structure | Mcalc. | Mexp. | tR (min) | purity | λmax (ABS) | λmax (EM) | φ | mg |
|---|---|---|---|---|---|---|---|---|---|
| BDM-323 | 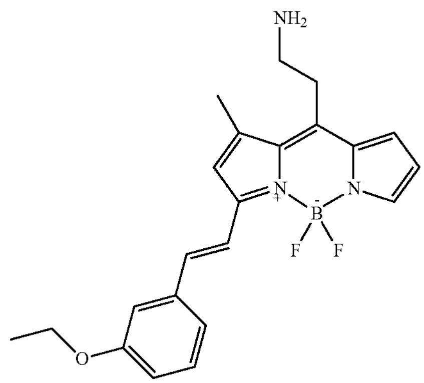 | 395.3 | 376.0 | 4.61 | 87% | 556 | 570 | 0.44 | 5.0 |
| BDM-325 | 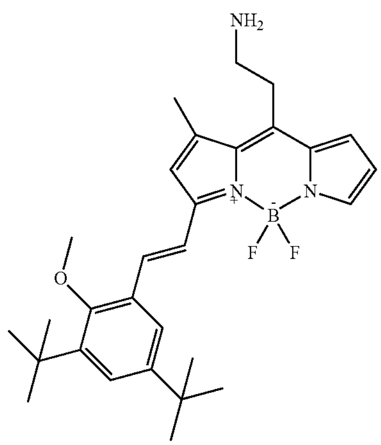 | 493.4 | 474.0 | 6.59 | 85% | 557 | 573 | 0.47 | 5.3 |
| BDM-326 | 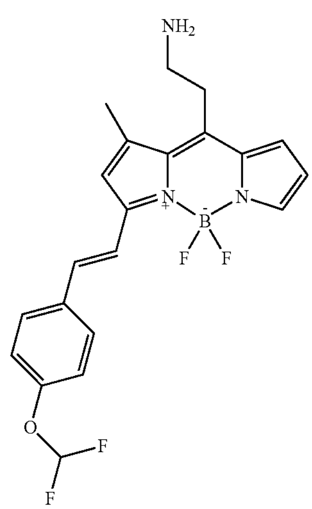 | 417.2 | 398.0 | 4.40 | 91% | 554 | 565 | 0.71 | 5.9 |

TABLE 1-continued

Chemical structures and characterization data for the BDM library.

| Code | Structure | Mcalc. | Mexp. | tR (min) | purity | λmax (ABS) | λmax (EM) | φ | mg |
|---|---|---|---|---|---|---|---|---|---|
| BDM-331 | 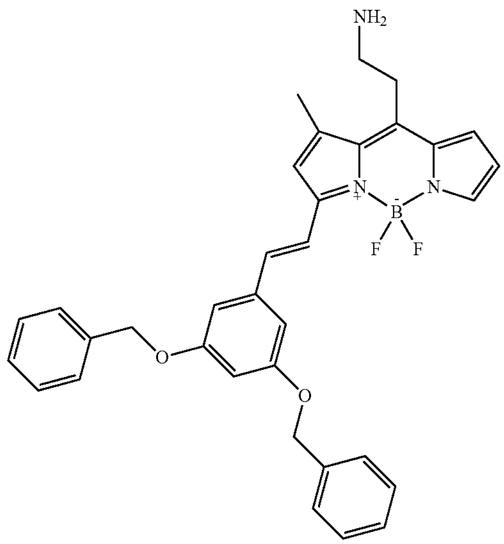 | 563.4 | 543.9 | 6.05 | 84% | 554 | 566 | 0.65 | 9.3 |
| BDM-332 | 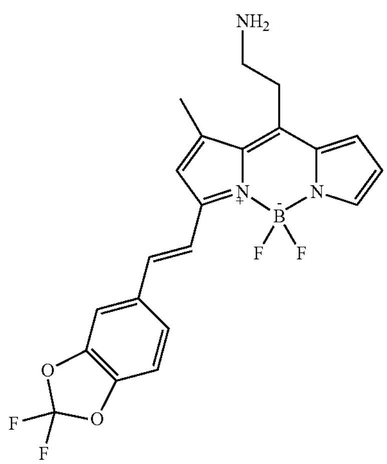 | 431.2 | 411.9 | 4.83 | 91% | 552 | 562 | 0.61 | 5.3 |
| BDM-333 | 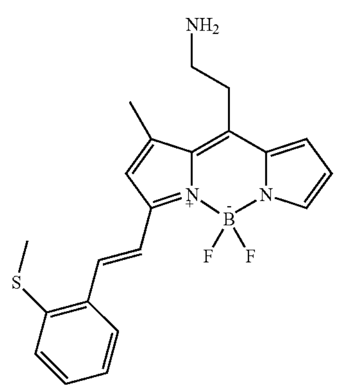 | 397.3 | 378.0 | 4.51 | 95% | 557 | 575 | 0.30 | 5.6 |

TABLE 1-continued

Chemical structures and characterization data for the BDM library.

| Code | Structure | Mcalc. | Mexp. | tR (min) | purity | λmax (ABS) | λmax (EM) | φ | mg |
|------|-----------|--------|-------|----------|--------|------------|-----------|---|-----|
| BDM-335 | 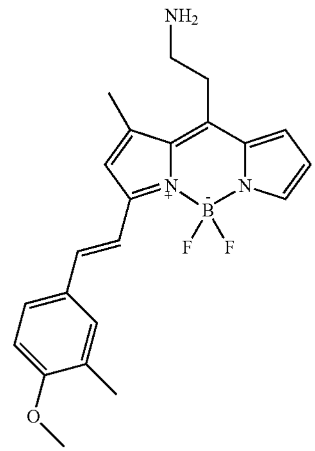 | 395.3 | 376.0 | 4.57 | 95% | 565 | 591 | 0.78 | 6.2 |
| BDM-336 | 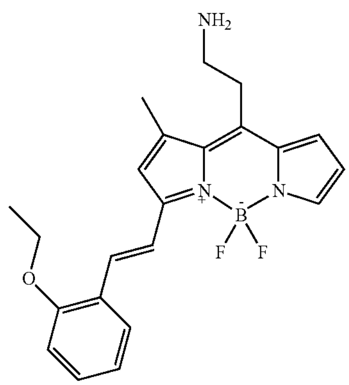 | 395.3 | 376.0 | 4.53 | 91% | 560 | 577 | 0.58 | 3.4 |
| BDM-340 | 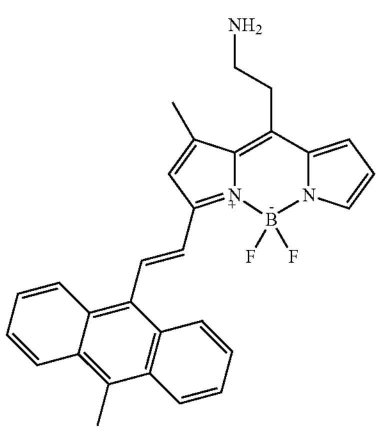 | 465.3 | 445.9 | 5.43 5.57 | 96% | 534 | 541 | 0.11 | 5.0 |

TABLE 1-continued

Chemical structures and characterization data for the BDM library.

| Code | Structure | Mcalc. | Mexp. | tR (min) | purity | λmax (ABS) | λmax (EM) | φ | mg |
| --- | --- | --- | --- | --- | --- | --- | --- | --- | --- |
| BDM-341 | 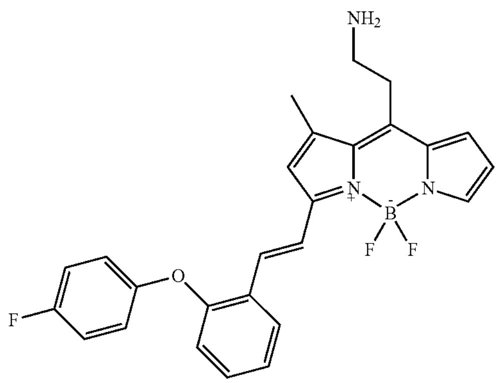 | 461.3 | 441.9 | 5.09 | 90% | 556 | 570 | 0.37 | 12.4 |
| BDM-343 | 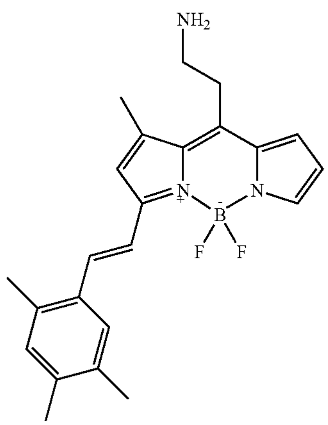 | 393.3 | 374.0 | 5.08 | 91% | 559 | 577 | 0.28 | 9.6 |
| BDM-345 | 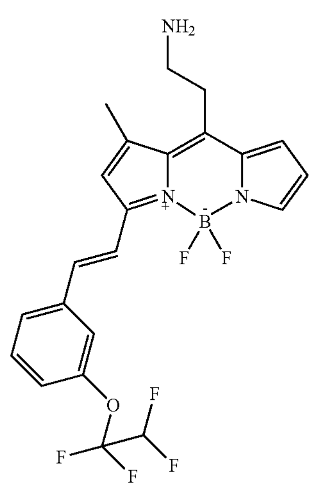 | 467.2 | 447.9 | 4.92 | 88% | 551 | 564 | 0.22 | 7.4 |

TABLE 1-continued
Chemical structures and characterization data for the BDM library.
| Code | Structure | Mcalc. | Mexp. | tR (min) | purity | λmax (ABS) | λmax (EM) | φ | mg |
|------|-----------|--------|-------|----------|--------|------------|-----------|---|-----|
| BDM-347 | 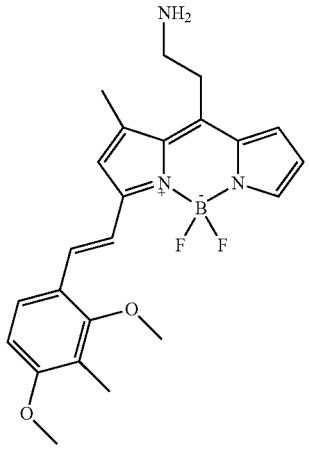 | 425.3 | 406.0 | 4.67 | 96% | 566 | 591 | 0.57 | 5.3 |
| BDM-350 | 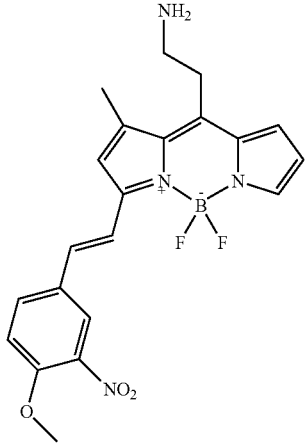 | 426.2 | 406.9 | 3.93 | 98% | 556 | 571 | 0.14 | 5.9 |
| BDM-356 | 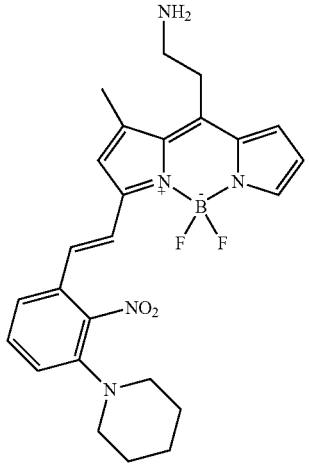 | 479.3 | 460.0 | 5.16 | 92% | 573 | 682 | 0.03 | 4.2 |

TABLE 1-continued
Chemical structures and characterization data for the BDM library.
| Code | Structure | Mcalc. | Mexp. | tR (min) | purity | λmax (ABS) | λmax (EM) | φ | mg |
|---|---|---|---|---|---|---|---|---|---|
| BDM-357 | 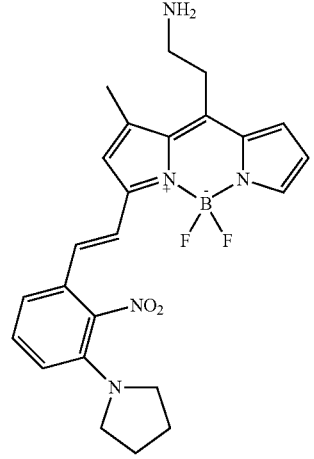 | 465.3 | 446.0 | 4.72 | 90% | 585 | 687 | 0.04 | 5.0 |
| BDM-359 | 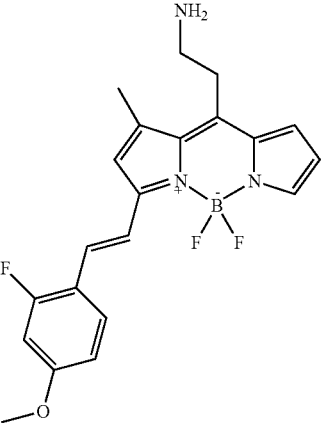 | 399.2 | 380.0 | 4.33 | 100% | 559 | 574 | 0.83 | 6.6 |
| BDM-363 | 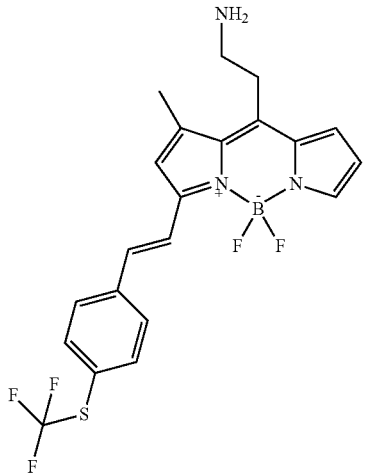 | 451.3 | 431.8 | 4.98 | 96% | 553 | 564 | 0.51 | 6.1 |

TABLE 1-continued

Chemical structures and characterization data for the BDM library.

| Code | Structure | Mcalc. | Mexp. | tR (min) | purity | λmax (ABS) | λmax (EM) | φ | mg |
|---|---|---|---|---|---|---|---|---|---|
| BDM-365 | 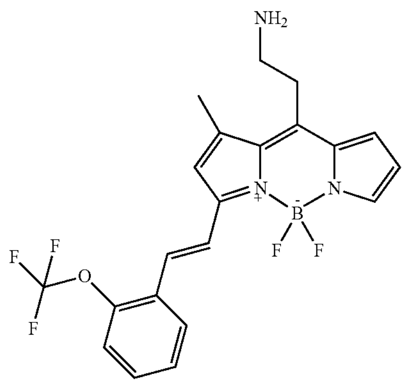 | 435.2 | 415.9 | 4.77 | 96% | 549 | 563 | 0.24 | 5.2 |
| BDM-369 | 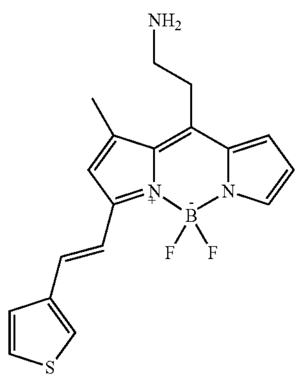 | 357.2 | 337.9 | 3.96 | 93% | 554 | 570 | 0.30 | 3.6 |
| BDM-371 | 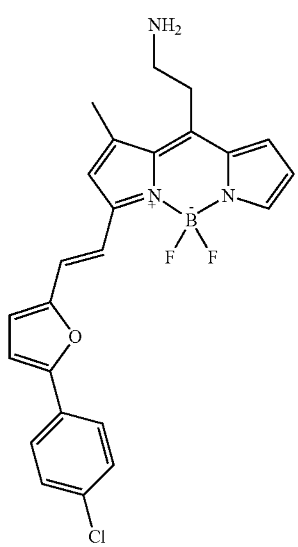 | 451.7 | 431.9 | 5.35 | 90% | 590 | 630 | 0.03 | 4.8 |

TABLE 1-continued
Chemical structures and characterization data for the BDM library.
| Code | Structure | Mcalc. | Mexp. | tR (min) | purity | λmax (ABS) | λmax (EM) | φ | mg |
|---|---|---|---|---|---|---|---|---|---|
| BDM-372 | 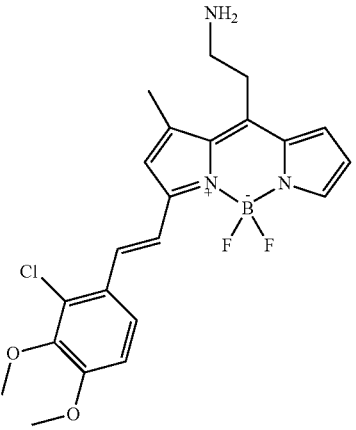 | 445.7 | 425.9 | 4.34 | 87% | 561 | 578 | 0.55 | 8.5 |
| BDM-377 | 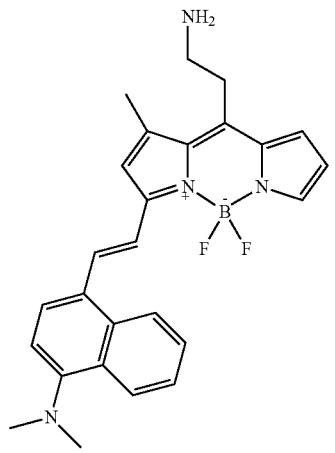 | 444.3 | 445.0 | 4.76 | 98% | 586 | n.d | 0.04 | 6.9 |
| BDM-378 | 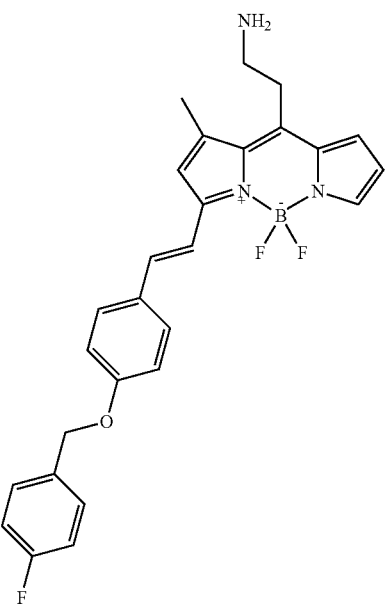 | 475.3 | 456.0 | 5.14 | 94% | 563 | 585 | 0.41 | 3.8 |

TABLE 1-continued

Chemical structures and characterization data for the BDM library.

| Code | Structure | Mcalc. | Mexp. | tR (min) | purity | λmax (ABS) | λmax (EM) | φ | mg |
|---|---|---|---|---|---|---|---|---|---|
| BDM-391 | 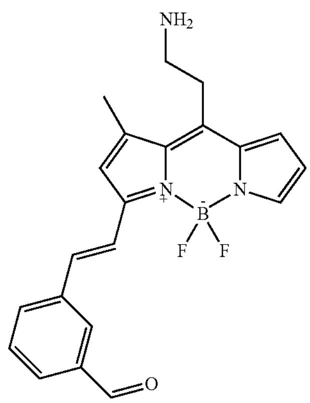 | 379.2 | 360.0 | 3.86 | 91% | 554 | 563 | 0.31 | 5.3 |
| BDM-397 | 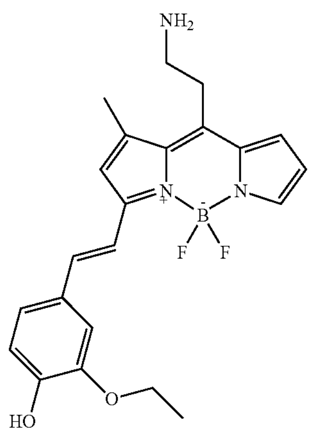 | 411.2 | 392.0 | 3.67 | 92% | 570 | 614 | 0.10 | 4.9 |
| BDM-401 | 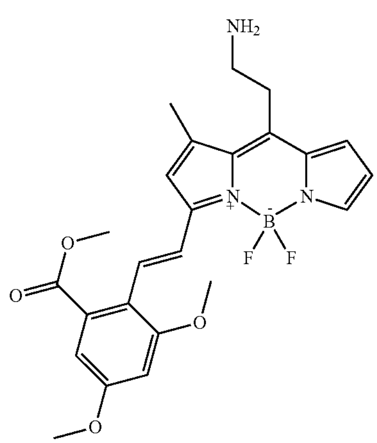 | 469.3 | 449.9 | 4.28 | 100% | 565 | 590 | 0.85 | 5.6 |

TABLE 1-continued
Chemical structures and characterization data for the BDM library.
| Code | Structure | Mcalc. | Mexp. | tR (min) | purity | λmax (ABS) | λmax (EM) | φ | mg |
|---|---|---|---|---|---|---|---|---|---|
| BDM-409 | 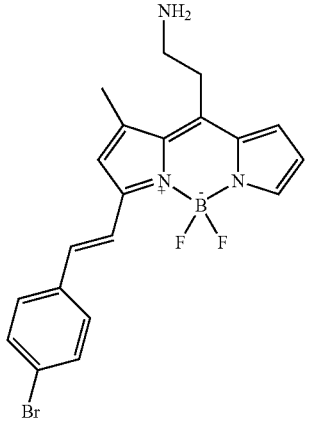 | 430.1 | 409.9 411.8 | 4.93 | 85% | 558 | 570 | 0.12 | 4.0 |
| BDM-425 | 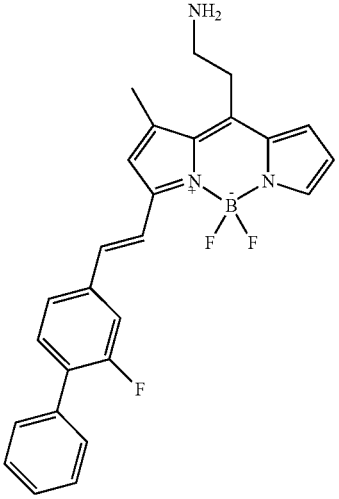 | 445.3 | 425.9 | 5.27 | 89% | 562 | 576 | 0.12 | 4.4 |
| BDM-429 | 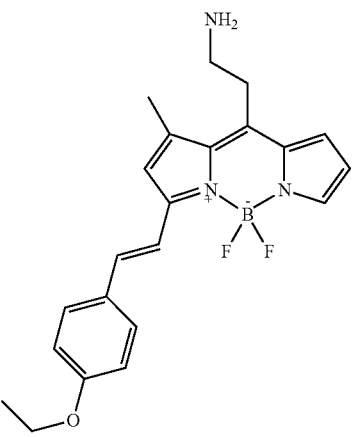 | 395.3 | 376.0 | 4.49 | 100% | 564 | 586 | 0.23 | 4.6 |

TABLE 1-continued

Chemical structures and characterization data for the BDM library.

| Code | Structure | Mcalc. | Mexp. | tR (min) | purity | λmax (ABS) | λmax (EM) | φ | mg |
|---|---|---|---|---|---|---|---|---|---|
| BDM-430 | 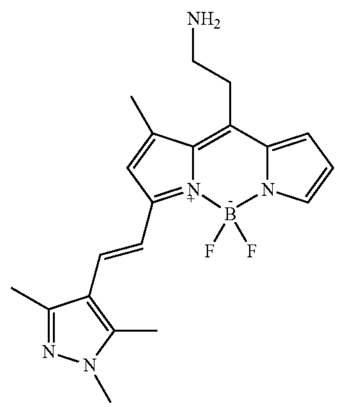 | 383.3 | 364.0 | 3.09 | 100% | 565 | 592 | 0.99 | 3.3 |
| BDM-435 | 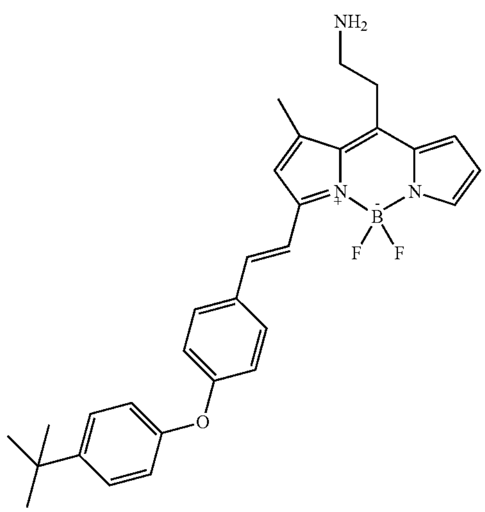 | 499.4 | 480.0 | 6.14 | 94% | 555 | 565 | 0.39 | 4.9 |
| BDM-437 | 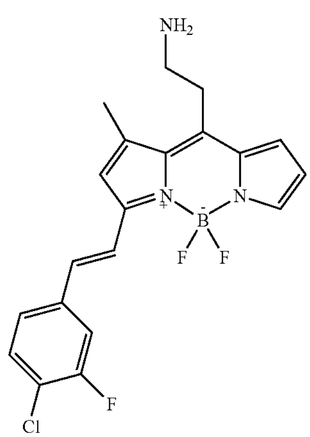 | 403.6 | 383.9 | 4.62 | 95% | 555 | 566 | 0.21 | 4.1 |

TABLE 1-continued

Chemical structures and characterization data for the BDM library.

| Code | Structure | Mcalc. | Mexp. | tR (min) | purity | λmax (ABS) | λmax (EM) | φ | mg |
|---|---|---|---|---|---|---|---|---|---|
| BDM-440 | 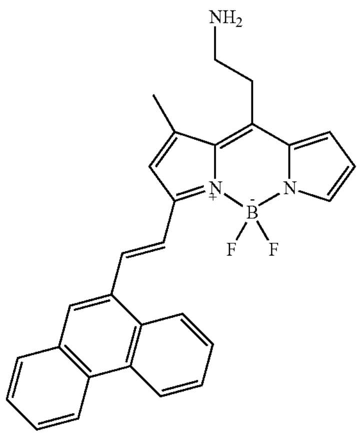 | 451.3 | 432.0 | 5.42 | 93% | 563 | 589 | 0.37 | 6.1 |
| BDM-89 | 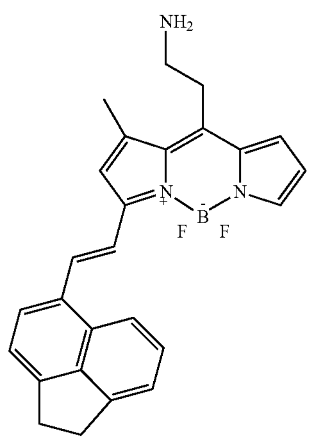 | 427.3 | 408.0 | 5.15 | 85% | 576 | 612 | 0.30 | 6.1 |
| BDM-384 | 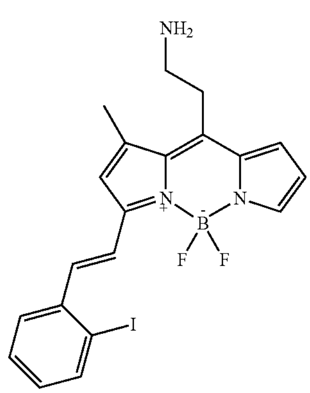 | 477.1 | 457.8 | 4.60 | 92% | 551 | 565 | 0.32 | 3.1 |

TABLE 1-continued

Chemical structures and characterization data for the BDM library.

| Code | Structure | Mcalc. | Mexp. | tR (min) | purity | λmax (ABS) | λmax (EM) | φ | mg |
|---|---|---|---|---|---|---|---|---|---|
| BDM-105 | 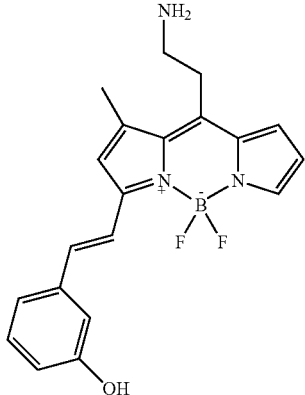 | 367.2 | 348.0 | 3.48 | 93% | 556 | 567 | 0.18 | 4.4 |
| BDM-82 | 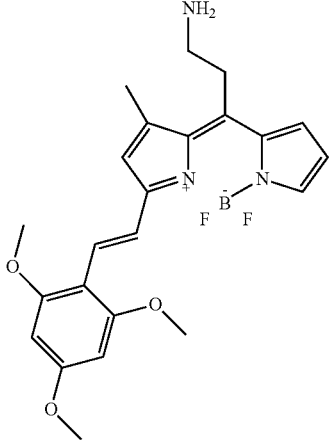 | 441.3 | 422.0 | 4.36 | 87% | 579 | 621 | 0.40 | 6.6 |
| BDM-17 | 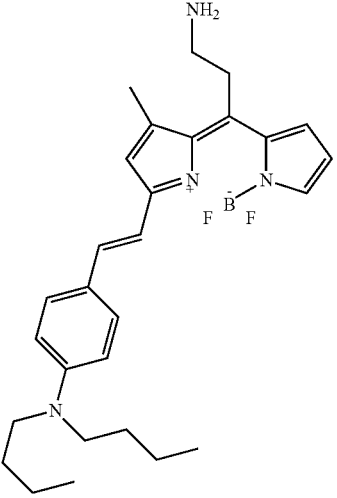 | 478.4 | 459.0 479.0 | 6.17 | 89% | 622 | 695 | 0.03 | 4.0 |

HPLC conditions: A: $H_2O$—HCOOH: 99.9:0.1. B: ACN—HCOOH: 99.9:0.1; gradient 5% B to 95% B (10 min), isocratic 95% B (2 min). Reverse-phase Agilent $C_{18}$ Zorbax column (2.1×30 mm2) 3.5 m, flow rate: 1 mL/min. Purity determined by integration of the absorbance peaks at 350 nm. ESI (+) m/z signals mostly correspond to the [M-F] fragmentation.

BODIPY has been widely used as a fluorophore due to its high photostability and extinction coefficient, high quantum yield and narrow excitation/emission bandwidth. However, solution-phase syntheses of BODIPY dyes often encompass tedious purification steps with typically low recovery yields, which seriously hampered the combinatorial derivatization of the BODIPY scaffold. With this first adaptation of the BODIPY scaffold to a solid-phase approach we accelerated the development of alkylamino BODIPY-based fluorescent probes. Alkylamino moieties can enhance protein/cell selectivity on BODIPY dyes, as demonstrated with the discovery of Ig Orange or CDy9, and can easily be modified with chemical or photoreactive tags for target identification studies. In addition, CDy9 showed an excellent potential for the imaging, isolation and characterization of mESC and it overcomes some limitations of the currently used-techniques (e.g. antibodies or genetically-modified cells) with a non-destructive, simple and cheap method for selectively staining mESC.

Alkylamino BODIPY tags can easily be modified with chemical or photoreactive tags (Scheme 3) for target identification studies, which is a key step and one of the bottlenecks of drug discovery and target validation programs. For the particular case of CDy9, this fluorescent probe showed an excellent staining selectivity on mESC when compared to a wide range of differentiated cell types, and thus could be used as a good research tool for imaging, isolation and characterization of mESC. Advantages of CDy9 over the conventional stem cell research tools involve a non-destructive and simple staining protocol—unlike antibodies of alkaline-phosphatase assays and do not require genetically-modified cells unlike GFP or luciferase-based mESC reporters.

DEFINITIONS

"Alkyl" means a saturated aliphatic branched or straight-chain monovalent hydrocarbon radical having the specified number of carbon atoms. Thus, "($C_1$-$C_6$) alkyl" means a radical having from 1-6 carbon atoms in a linear or branched arrangement. "($C_1$-$C_6$)alkyl" includes methyl, ethyl, propyl, isopropyl, butyl, isobutyl, sec-butyl, pentyl, and hexyl.

"Alkylene" means a saturated aliphatic straight-chain divalent hydrocarbon radical having the specified number of carbon atoms. Thus, "($C_1$-$C_6$)alkylene" means a divalent saturated aliphatic radical having from 1-6 carbon atoms in a linear arrangement. "($C_1$-$C_6$)alkylene" includes methylene, ethylene, propylene, butylene, pentylene and hexylene.

"Heterocycle" means a saturated or partially unsaturated (4-7 membered) monocyclic heterocyclic ring containing one nitrogen atom and optionally 1 additional heteroatom independently selected from N, O, or S. When one heteroatom is S, it can be optionally mono- or di-oxygenated (i.e., —S(O)— or —S(O)$_2$—). Examples of monocyclic heterocycle include, but are not limited to, azetidine, pyrrolidine, piperidine, piperazine, hexahydropyrimidine, tetrahydrofuran, tetrahydropyran, morpholine, thiomorpholine, thiomorpholine 1,1-dioxide, tetrahydro-2H-1,2-thiazin, tetrahydro-2H-1,2-thiazine 1,1-dioxide, isothiazolidine, or isothiazolidine 1,1-dioxide.

"Cycloalkyl" means a saturated aliphatic cyclic hydrocarbon ring. Thus, "$C_3$-$C_7$ cycloalkyl" means (3-7 membered) saturated aliphatic cyclic hydrocarbon ring. $C_3$-$C_7$ cycloalkyl includes, but is not limited to cyclopropyl, cyclobutyl, cyclopentyl, cyclohexyl and cycloheptyl.

The term "alkoxy" means —O-alkyl; "hydroxyalkyl" means alkyl substituted with hydroxy; "aryl alkyl" means alkyl substituted with an aryl group; "alkoxyalkyl" mean alkyl substituted with an alkoxy group; "alkylamine" means amine substituted with an alkyl group; "cycloalkylalkyl" means alkyl substituted with cycloalkyl; "dialkylamine" means amine substituted with two alkyl groups; "alkylcarbonyl" means —C(O)-A*, wherein A* is alkyl; "alkoxycarbonyl" means —C(O)—OA*, wherein A* is alkyl; and where alkyl is as defined above and OA* includes methoxy, ethoxy, propoxy, butoxy, pentoxy and hexoxy.

"Cycloalkoxy" means a cycloalkyl-O— group wherein the cycloalkyl is as defined above. Exemplary ($C_3$-$C_7$)cycloalkyloxy groups include cyclopropoxy, cyclobutoxy, cyclopentoxy, cyclohexoxy and cycloheptoxy.

Haloalkyl and halocycloalkyl include mono, poly, and perhaloalkyl groups where each halogen is independently selected from fluorine, chlorine, and bromine.

"Hetero" refers to the replacement of at least one carbon atom member in a ring system with at least one heteroatom selected from N, S, and O. A hetero ring system may have 1 or 2 carbon atom members replaced by a heteroatom.

"Halogen" and "halo" are interchangeably used herein and each refers to fluorine, chlorine, bromine, or iodine.

"Cyano" means —C≡N.

"Nitro" means —NO$_2$.

"Fmoc" is 9-Fluorenylmethyloxycarbonyl.

As used herein, an amino group may be a primary (—NH$_2$), secondary (—NHR$_x$), or tertiary (—NR$_x$R$_y$), wherein R$_x$ and R$_y$ may be any of the optionally substituted alkyls described above.

The terms "haloalkyl" and "haloalkoxy" mean alkyl or alkoxy, as the case may be, substituted with one or more halogen atoms. The term "halogen" means F, Cl, Br or I. Preferably the halogen in a haloalkyl or haloalkoxy is F.

The term "acyl group" means —C(O)B*, wherein B* is an optionally substituted alkyl group or aryl group (e.g., optionally substituted phenyl).

An "alkylene group" is represented by —[CH$_2$]$_z$—, wherein z is a positive integer, preferably from one to eight, more preferably from one to four.

An "alkenylene group" is an alkylene in which at least a pair of adjacent methylenes are replaced with —CH=CH—.

The term "($C_6$-$C_{10}$)aryl" used alone or as part of a larger moiety as in "arylalkyl", "arylalkoxy", or "aryloxyalkyl", means carbocyclic aromatic rings. The term "carbocyclic aromatic group" may be used interchangeably with the terms "aryl", "aryl ring" "carbocyclic aromatic ring", "aryl group" and "carbocyclic aromatic group". An aryl group typically has 6-14 ring atoms. A "substituted aryl group" is substituted at any one or more substitutable ring atom. The term "$C_{6-14}$ aryl" as used herein means a monocyclic, bicyclic or tricyclic carbocyclic ring system containing from 6 to 14 carbon atoms and includes phenyl, naphthyl, anthracenyl, 1,2-dihydronaphthyl, 1,2,3,4-tetrahydronaphthyl, fluorenyl, indanyl, indenyl and the like.

The term "heteroaryl", "heteroaromatic", "heteroaryl ring", "heteroaryl group" and "heteroaromatic group", used alone or as part of a larger moiety as in "heteroarylalkyl" or "heteroarylalkoxy", refers to aromatic ring groups having five to fourteen ring atoms selected from carbon and at least one (typically 1-4, more typically 1 or 2) heteroatoms (e.g., oxygen, nitrogen or sulfur). They include monocyclic rings and polycyclic rings in which a monocyclic heteroaromatic ring is fused to one or more other carbocyclic aromatic or heteroaromatic rings. The term "5-14 membered heteroaryl" as used herein means a monocyclic, bicyclic or tricyclic ring system containing one or two aromatic rings and from 5, to 14 atoms of which, unless otherwise specified, one, two, three, four or five are heteroatoms independently selected from N, NH, N($C_{1-6}$alkyl), O and S.

The term "2-4 member polycyclyl" is a cyclic compound with 2-4 hydrocarbon loop or ring structures (e.g., benzene rings). The term generally includes all polycyclic aromatic compounds, including the polycyclic aromatic hydrocarbons, the heterocyclic aromatic compounds containing sulfur, nitrogen, oxygen, or another non-carbon atoms, and substituted derivatives of these.

The term "Alkenyl" means a straight or branched hydrocarbon radical having a specified number of carbon atoms and includes at least one double bond. The $(C_6-C_{10})$aryl$(C_2-C_6)$ alkenyl group connects to the remainder of the molecule through the $(C_2-C_6)$alkenyl portion of $(C_6-C_{10})$aryl$(C_2-C_6)$ alkenyl.

Another embodiment of the present invention is a pharmaceutical composition comprising one or more pharmaceutically acceptable carrier and/or diluent and a compound disclosed herein or a pharmaceutically acceptable salt thereof.

"Pharmaceutically acceptable carrier" and "pharmaceutically acceptable diluent" means non-therapeutic components that are of sufficient purity and quality for use in the formulation of a composition of the invention that, when appropriately administered to an animal or human, typically do not produce an adverse reaction, and that are used as a vehicle for a drug substance (i.e. a compound of the present invention).

Pharmaceutically acceptable salts of the compounds of the present invention are also included. For example, an acid salt of a compound of the present invention containing an amine or other basic group can be obtained by reacting the compound with a suitable organic or inorganic acid, resulting in pharmaceutically acceptable anionic salt forms. Examples of anionic salts include the acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrobromide, hydrochloride, hydroxynaphthoate, iodide, isethionate, lactate, lactobionate, malate, maleate, mandelate, mesylate, methylsulfate, mucate, napsylate, nitrate, pamoate, pantothenate, phosphate/diphosphate, polygalacturonate, salicylate, stearate, subacetate, succinate, sulfate, tannate, tartrate, teoclate, tosylate, and triethiodide salts.

Salts of the compounds of the present invention containing a carboxylic acid or other acidic functional group can be prepared by reacting with a suitable base. Such a pharmaceutically acceptable salt may be made with a base which affords a pharmaceutically acceptable cation, which includes alkali metal salts (especially sodium and potassium), alkaline earth metal salts (especially calcium and magnesium), aluminum salts and ammonium salts, as well as salts made from physiologically acceptable organic bases such as trimethylamine, triethylamine, morpholine, pyridine, piperidine, picoline, dicyclohexylamine, N,N'-dibenzylethylenediamine, 2-hydroxyethylamine, bis-(2-hydroxyethyl)amine, tri-(2-hydroxyethyl)amine, procaine, dibenzylpiperidine, dehydroabietylamine, N,N'-bisdehydroabietylamine, glucamine, N-methylglucamine, collidine, quinine, quinoline, and basic amino acids such as lysine and arginine.

"FRET sensor" means a sensor utilized in measuring Foerster resonance energy transfer, which is a mechanism describing energy transfer between two chromophores.

"Surface plasmon resonance" is the property of the resonant, collective oscillation of valence electrons in a solid stimulated by incident light. Resonance is reached when the frequency of the light photons matches the frequency of the surface electrons.

A "ratiometric sensor" is a voltage-based sensor measuring fluorescence, wherein the voltage output from the sensor is proportional to the voltage input.

"Flow cytometry" is a laser-based method used for counting and sorting cells, as well as detecting biomarkers in a biological sample.

EXAMPLES

The following examples are provided to illustrate one or more preferred embodiments of the invention, but are not limited embodiments thereof. Numerous variations can be made to the following examples that lie within the scope of the invention.

Example 1

Synthesis of the Alkylamino BODIPY Scaffold 3 and its Derivitization in Solid-Phase to Render BDM Compounds Using relatively inexpensive starting materials (Fmoc-β-alanine and pyrrole), the 2-ketopyrrole 1 was prepared following slightly modified reported methods.[23]

(9H-fluoren-9-yl)methyl 3-oxo-3-(1H-pyrrol-2-yl) propylcarbamate (1)

Fmoc-β-Ala-OH (2.5 g, 8.0 mmol) was dissolved in dry THF. 2,2'-dipyridyl disulfide (2.7 g, 12.0 mmol) and $PPh_3$ (4.2 g, 16.0 mmol) were added, and the mixture was stirred under $N_2$ atmosphere at r.t for 24 h. In a separate flask, methylmagnesium bromide (12 mL of a 3.0 M solution in THF, 36.0 mmol) was added dropwise at −78° C. to a solution of pyrrole (3.3 mL, 48.0 mmol) in dry THF (50 mL). The mixture was stirred at −78° C. for 30 min and at −20° C. for another 30 min. Then the thioester crude mixture (after 24 h reaction) was added drop wise at −78° C., and the whole solution was stirred at −78° C. for 30 min and another 30 min at r.t. The reaction was quenched with a saturated solution of $NH_4Cl$. After dilution with diethyl ether, the organic layer was washed with water (3×100 mL) and brine (100 mL), dried over anhydrous sodium sulfate and evaporated under vacuum. Column chromatography (elution with hexane-ethyl acetate 1:1) rendered 2.53 g of 1 as a white solid (yield: 88%). ESI m/z ($C_{22}H_{20}N_2O_3$), calc: 359.2. found (M+Na$^+$): 382.9. $^1$HNMR (300 MHz, CDCl$_3$): 9.68 (bs, 1H), 7.75 (d, 2H, J=7.3 Hz), 7.57 (d, 2H, J=7.8 Hz), 7.38 (t, 2H, J=7.6 Hz), 7.28 (t, 2H, J=7.3 Hz), 7.04 (bs, 1H), 6.94 (bs, 1H), 6.28 (d, 1H, J=2.9 Hz), 5.48 (bt, 1H, J=5.9 Hz), 4.38 (d, 2H, J=7.0 Hz), 4.20 (t, 1H, J=7.0 Hz), 3.61 (dt, 2H, J=5.9 Hz, 6.1 Hz), 3.06 (t, 2H, J=5.9 Hz). $^{13}$C-NMR (75 MHz, CDCl$_3$): 189.0, 156.4, 143.9, 141.3, 131.7, 127.6, 127.0, 125.1, 124.9, 119.9, 116.8, 110.9, 66.7, 47.2, 37.6, 36.3.

Further condensation with 2,4-dimethylpyrrole and $POCl_3$, and in situ addition of the $BF_3.OEt_2$ yielded the BODIPY derivative 2.

10-(2-(((9H-fluoren-9-yl)methoxy)carbonylamino) ethyl)-5,5-difluoro-1,3-dimethyl-5H-dipyrrolo[1,2-c: 1',2'-f][1,3,2]diazaborinin-4-ium-5-uide (2)

1 (1.5 g, 4.2 mmol) and 2,4-dimethylpyrrole (692 μL, 6.7 mmol) were dissolved in $CH_2Cl_2$ at 0° C. After 10 min stirring, the mixture was treated drop wise with $POCl_3$ (1.3 g, 8.4 mmol), and the resulting solution was stirred at 0° C. for 1 h, and at 35° C. for 20 h. Afterwards, DIEA (2.9 mL, 16.8 mmol) and $BF_3.OEt_2$ (2.3 mL, 16.8 mmol) were added and the crude mixture was stirred for 4 h at r.t. Column chromatography (elution with hexane-ethyl acetate 4:1) rendered 1.2 g of 2 as a reddish solid (yield: 57%). ESI m/z ($C_{28}H_{26}BF_2N_3O_2$), calc: 485.2. found (M-F): 466.3. $^1$H-NMR (300 MHz, CDCl$_3$): 7.77 (d, 2H, J=7.6 Hz), 7.61 (bs, 1H), 7.56 (d, 2H, J=7.0 Hz), 7.41 (t, 2H, J=7.6 Hz), 7.31 (t, 2H, J=7.3 Hz), 7.11 (d, 1H, J=3.5 Hz), 6.42 (d, 1H, J=3.2 Hz), 6.17 (bs, 1H), 5.10 (bt, 1H, J=6.2 Hz), 4.43 (d, 2H, J=6.7 Hz), 4.19 (t, 1H, J=6.7 Hz), 3.50 (dt, 2H, J=6.7 Hz, 7.2 Hz), 3.18 (t, 2H, J=7.0 Hz), 2.58 (s, 3H), 2.46 (s, 3H). $^{13}$C-NMR (75 MHz, CDCl$_3$):

161.2, 156.3, 145.2, 145.1, 143.7, 142.3, 141.3, 138.2, 134.0, 127.7, 127.0, 125.0, 124.0, 123.8, 120.0, 116.1, 66.8, 47.2, 42.8, 30.1, 16.2, 15.0. $^{19}$F-NMR (282 MHz, CDCl$_3$): −70.31, −70.53 (dd, J=31 Hz, J=62 Hz, BF$_2$).

The treatment of 2 with DBU followed by quenching with aqueous HCl afforded 3 as a hydrochloride salt.

10-(2-aminoethyl)-5,5-difluoro-1,3-dimethyl-5H-dipyrrolo[1,2-c:1',2'-f][1,3,2]diazaborinin-4-ium-5-uide hydrochloride (3)

A solution of 2 (1.0 g, 2.06 mmol) in CH$_2$Cl$_2$ was treated with DBU every 15 min for a total of 4 times (4×73 μL, 4×0.51 mmol) and a total reaction time of 1 h. Afterwards, the reaction was quenched with a aqueous solution of 0.5 N HCl and stirred for 15 min at r.t. The resulting red solid was filtered off, and thoroughly washed with diethyl ether to render 350 mg of 3 as the hydrochloride salt (yield: 65%). ESI m/z (C$_{13}$H$_{16}$BF$_2$N$_3$), calc: 263.1. found (M-F): 244.1. $^1$H-NMR (300 MHz, DMSO-d$_6$): 8.51 (bs, 2H), 7.65 (s, 1H), 7.63 (s, 1H), 6.52 (s, 1H), 6.46 (s, 1H), 3.37 (m, 2H), 3.16 (s, 3H), 3.03 (m, 2H), 2.50 (s, 3H). $^{13}$C-NMR (75 MHz, DMSO-d$_6$): 161.6, 146.3, 141.0, 138.0, 133.5, 133.3, 124.7, 124.0, 116.1, 48.5, 47.8, 15.9, 14.6. $^{19}$F-NMR (282 MHz, DMSO-d$_6$): −66.97, −67.19 (dd, J=29 Hz, J=61 Hz, BF$_2$).

This product was loaded on CTC-PS resin so that the activated C$_3$-methyl group of the BODIPY structure could be modified in a solid-phase adapted Knoevenagel-type reaction.[24]

Synthesis of the BDM Library.

A solution of 3 (350 mg, 1.3 mmol) and DIEA (1.1 mL, 6.5 mmol) was dissolved in N-methylpyrrolidone (NMP) and added to 2-chlorotrityl chloride polystyrene resin (loading: 1.2 mmol/g, 3.3 g, 3.9 mmol). The reaction was shaken at r.t. for 16 h, after which the resin was capped with MeOH (0.8 mL/g resin) for 4 h, and finally filtered off and washed with NMP, DMF and DCM (×4 each solvent). For every compound, 50 mg of the loaded resin (corresponding to 0.06 mmol of 3) were re-suspended in 2 mL DMSO-ACN (1:1), and treated with pyrrolidine (75 μL, 0.9 mmol), AcOH (54 μL, 0.9 mmol) and the corresponding aldehydes (0.9 mmol). The resulting suspension was heated at 85° C. for 5 min, cooled down to r.t., filtered off, and washed with DMF and DCM (×4 each solvent). Afterward, the resins were treated with a solution of TFA-DCM (0.5:99.5) (2×10 min), and the resulting filtrates were combined and evaporated under pressure. BDM products were isolated as the free-amine compounds after silica-based SPE elution with DCM-MeOH (98:2) containing 1% NH$_3$ concentration in MeOH (full characterization data on Table 1). The procedure rendered aminoethyl styryl-BODIPY compounds (BDM) with purities averaging 91%. Ig Orange (BDM-69): $^1$H-NMR (300 MHz, CDCl$_3$): 7.57-7.61-7.69 (m, 8H), 7.39 (d, 4H, J=7.6 Hz), 7.17 (d, 4H, J=8.8 Hz), 6.80 (s, 1H), 6.50 (dd, 1H, J=2.1 Hz, J=4.0 Hz), 3.18 (d, 2H, J=6.4 Hz), 3.12 (d, 2H, J=6.4 Hz), 2.54 (s, 3H), 1.63 (bs, 2H). $^{13}$C-NMR (75 MHz, CDCl$_3$): 157.0, 143.9, 140.6, 139.2, 138.9, 137.8, 136.9, 135.0, 134.4, 129.8, 128.6, 128.2, 127.8, 127.8, 126.9, 126.5, 123.4, 122.1, 119.7, 118.0, 116.0, 77.2, 43.4, 31.8, 29.5, 16.2. $^{19}$F-NMR (282 MHz, CDCl$_3$): −65.82, −66.03 (dd, J=30 Hz, J=59 Hz, BF$_2$).

Example 2

Quantum Yield Measurements

Quantum yields were calculated by measuring the integrated emission area of the fluorescent spectra, and referring them to the area measured for Rhodamine B in EtOH after excitation at 510 nm ($\Phi_{Rho-B}$=0.70). Quantum yields for the BDM products were then calculated using equation below, where F represents the area of fluorescent emission, n is reflective index of the solvent, and Abs is absorbance at excitation wavelength selected for standards and samples. Emission was integrated from 540 nm to 800 nm.

$$\Phi_{flu}^{sample} = \Phi_{fl}^{reference}\left(\frac{F^{sample}}{F^{reference}}\right)\left(\frac{\eta^{sample}}{\eta^{reference}}\right)\left(\frac{Abs^{reference}}{Abs^{sample}}\right)$$

Example 3

Screening the BDM Library

Fluorescence intensities were measured using a Spectra Max Gemini XSF plate reader in a 384-well plate. BDM compounds were dissolved to a final concentration of 10 μM (20 mM HEPES buffer, pH 7.4, containing 1% DMSO) and incubated with different proteins and peptides at different serial concentrations in 20 mM HEPES buffer (pH 7.4) (FIG. 1a). The excitation wavelength was set at 510 nm, and the emission spectra were recorded from 560 to 700 nm. Fluorescence fold increase ratios were determined by referring the maximum fluorescence intensity emission of BDM compounds in the presence of the screened proteins and peptides to the maximum fluorescence intensity emission of BDM compounds in 20 mM HEPES buffer (pH 7.4) (FIG. 1b).

Extended Screening of IgG Orange (BDM-69).

Figure 2:
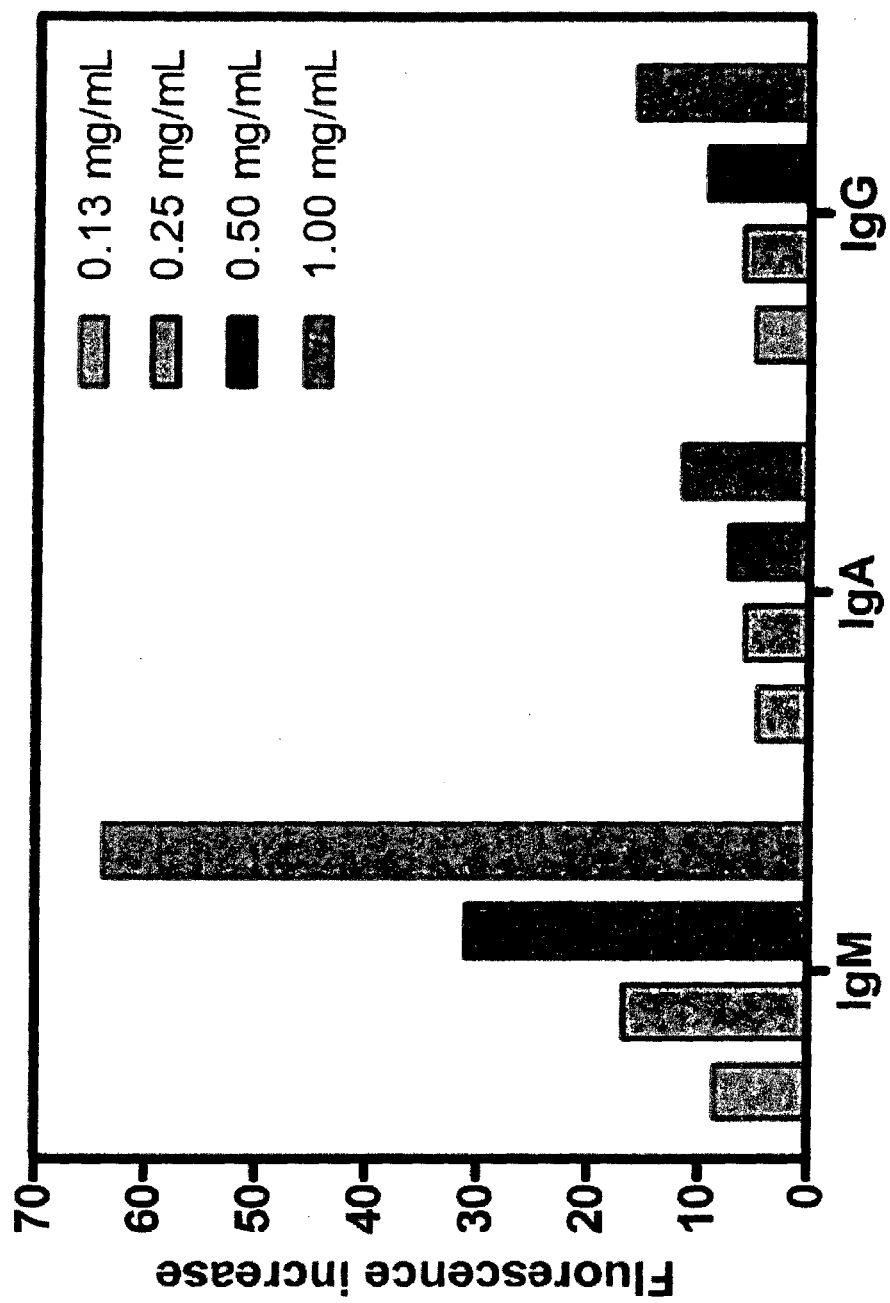
FIG. 2 shows the fluorescence response of Ig Orange upon incubation with different concentrations of human IgM, IgA, and IgG.

IgG Orange was dissolved to a final concentration of 10 μM (PBS buffer, pH 7.3, containing 1% DMSO) and incubated with human IgG, IgA and IgM at different concentrations in PBS buffer (pH 7.3) (FIG. 2). The excitation wavelength was set at 530 nm, and fluorescence fold increase ratios were determined by referring the maximum fluorescence intensity emission (590 nm) of Ig Orange in the presence of immunoglobulins to the maximum fluorescence intensity emission of Ig Orange in buffer.

Example 4

Ig Orange Response Against IgG in Human Serum Samples

Figure 3:
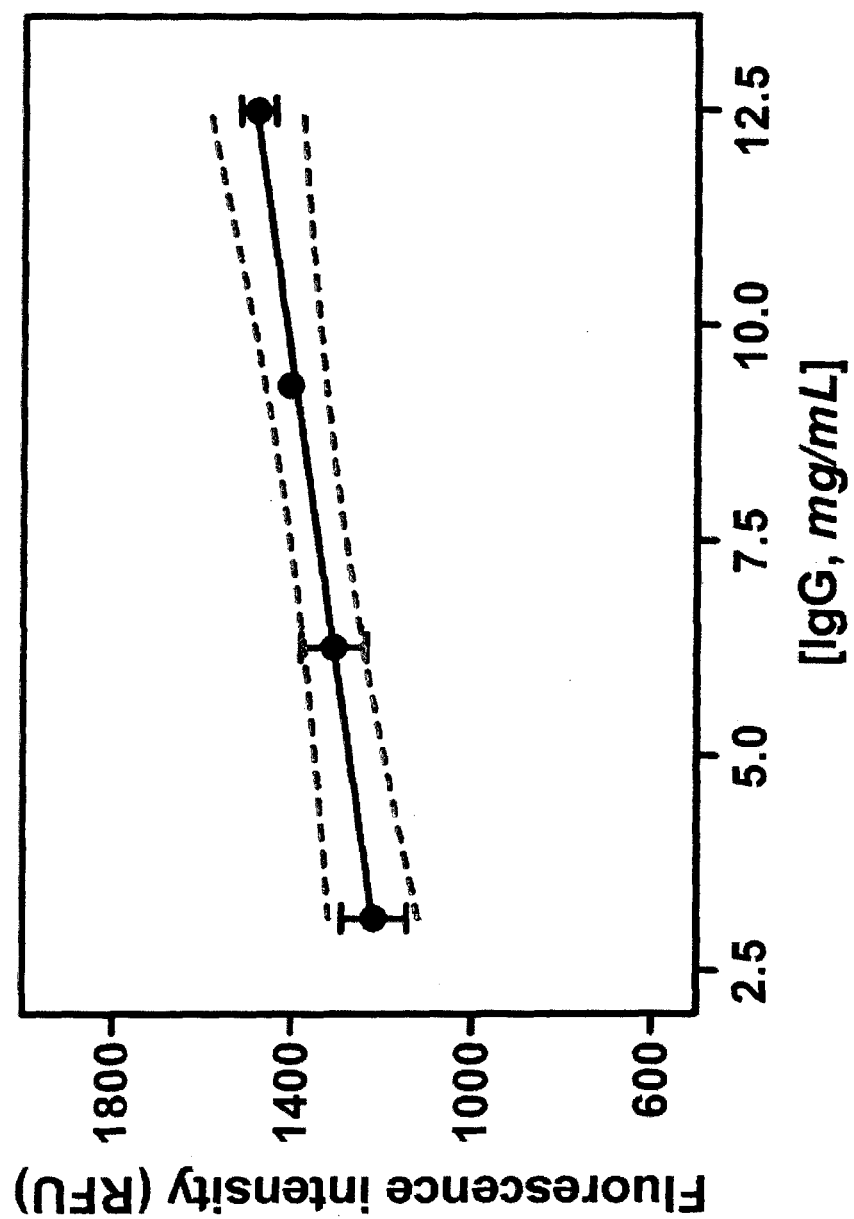
FIG. 3 shows the fluorescence response of Ig Orange against known concentrations of IgG in immunoglobulin-depleted human serum. Values are represented as means (n=3) and error bars as standard deviations. Dotted grey lines indicated a 95% reliability interval. Regression coefficient $(R^2)=0.99$.

Known amounts of human IgG covering the whole physiological range (3.3, 6.2, 9.4 and 12.5 mg/mL) were added to immunoglobulin (G, A, M)—depleted human serum (Sigma Aldrich). The resulting samples were diluted 10 times in PBS buffer (pH 7.3) to reach a final volume of 100 μL and Ig Orange (1 μL, 1 mM) was added (final Ig Orange concentration: 10 μM). Fluorescence intensities of the samples were recorded on a SpectraMax M2 plate reader (exc: 530 nm; emission: 590 nm) (FIG. 3). The experimental data was fitted to a linear regression using Graphpad Prism 5.0 software.

Example 5

Surface Plasmon Resonance and Job Plot Analysis

Figure 4:
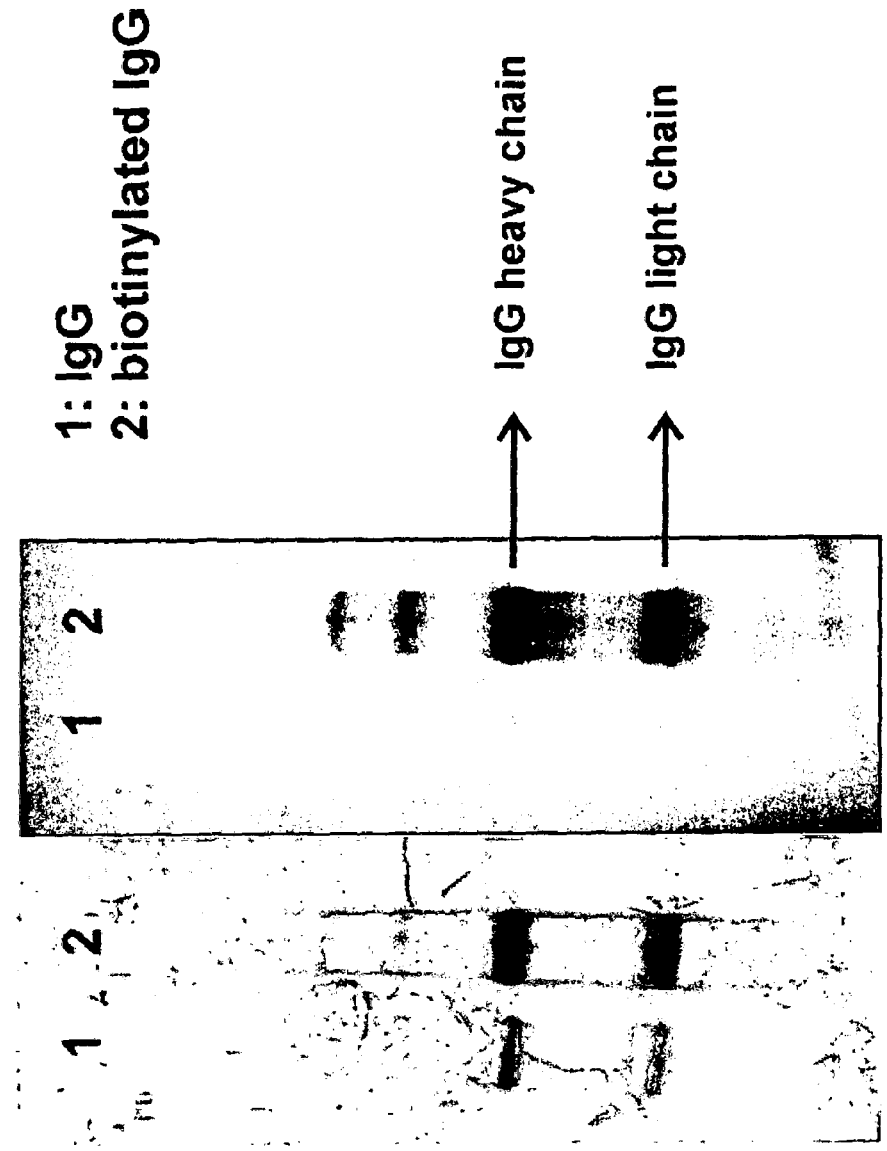
FIG. 4 shows the SDS-PAGE gel and Western blotting of human non-modified and biotinylated IgG. At left, samples were solved by SDS-PAGE and stained with Coomassie Blue, and at right, samples were solved by Western blotting and immunoblots were incubated with HRP-conjugated streptavidin.
Figure 5:
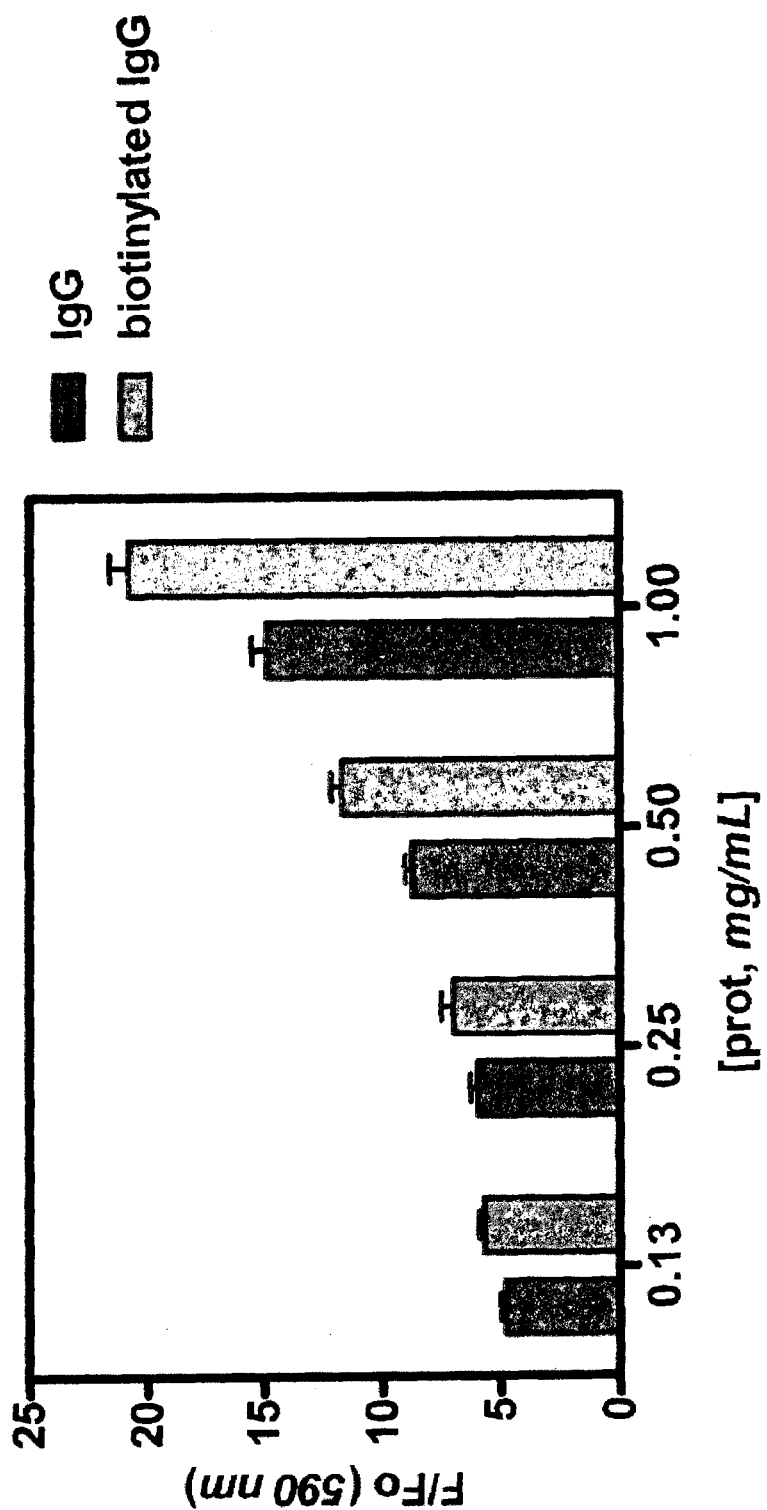
FIG. 5 shows comparative fluorescence increase of Ig Orange after incubation with different concentrations of non-modified and biotinylated human IgG. Values are represented as means (n=3) and error bars as standard deviations.

Human IgG (5.0 mg, 0.033 μmol) and biotin-OSu (0.11 mg, 0.33 μmol) were dissolved in 0.1 M NaHCO$_3$ (pH 8.5) and shaken for 1 h at 25° C. Excess of biotinylating reagent was removed by centrifugation with Microcon 30K filters (3 rounds at 14,000 rpm for 20 min at 4° C.). The purified biotinylated IgG was resuspended in PBS, and characterized by SDS-PAGE and Western blotting with HRP conjugated streptavidin (FIG. 4). The fluorescence response of Ig Orange to IgG and biotinylated IgG was compared (FIG. 5). The concentration of biotinylated IgG before fluorescence and SPR experiments was determined by Bradford assay. SPR measurements were performed on a T-200 instrument (Biacore AB, GE Healthcare) equipped with Series S sensor chip CM7 (Biacore AB, GE Healthcare). All experiments were performed at 25° C. Briefly, the carboxymethylated sensor surface was activated for 7 min with 1:1 of 0.2 M EDC(N-ethyl-N-[3-(diethylamino)propyl]carbodiimide) and 50 mM NHS(N-hydroxysuccinimide), then human IgG was coupled to 12,000 RU and finally the surface was deactivated for 7 min with 1 M ethanolamine HCl (pH 8.5). The immobilized immunoglobulin was probed with one positive- and one negative-binding fragment diluted into the running buffer (10 mM sodium phosphate buffer, 150 mM NaCl, 1% DMSO, pH 7.4) to ascertain its functionality. Ig Orange (0.07, 0.21, 0.62, 1.86, 5.57 and 16.7 µM, in duplicates) was injected across a control surface and the immobilized surface serially. Sensorgrams obtained were DMSO calibrated and buffer- and reference-subtracted (FIG. 6a). Responses at equilibrium were plotted against analyte concentration and fit to a simple isotherm to obtain the affinity constant using Scrubber 2 software (BioLogics Inc. Australia). Job Plot Analysis: Ig Orange (final concentrations: 0, 1.6, 3.2, 4.8, 6.4, 8.0, 9.6, 11.2, 12.8, 14.4, 16 µM) and human IgG (final concentrations: 16, 14.4, 12.8, 11.2, 9.6, 8.0, 6.4, 4.8, 3.2, 1.6, 0 µM) were incubated in PBS buffer (pH 7.3) containing 1% DMSO, and the fluorescence intensities of the different solutions were recorded on a SpectraMax M2 plate reader (excitation: 530 nm; emission: 590 nm). The Job plot is represented as [fluorescence fold increase × ratio Ig Orange] vs. ratio Ig Orange, with values as means (n=3) and error bars as standard deviations (FIG. 6b).

Example 6

Structure-Fluorescence Relationships of Ig Orange and Additional SPR Experiments Ig Orange (BDM-69) (10 µM) and BD-69 (10 µM) were incubated with different concentrations of human IgG in 20 mM HEPES buffer (pH 7.4) and the fluorescence intensities were recorded on a SpectraMax M2 plate reader (excitation: 530 nm; emission: 590 nm), as shown in FIG. 7a. Values are represented as means (n=3) of the fluorescence fold increase after incubation with the protein. FIG. 7b shows a binding sensorgram of the aminoethyl-free compound (BD-69).

Example 7

Binding of Ig Orange to polyclonal IgG and monoclonal IgG$_1$

Figure 8:
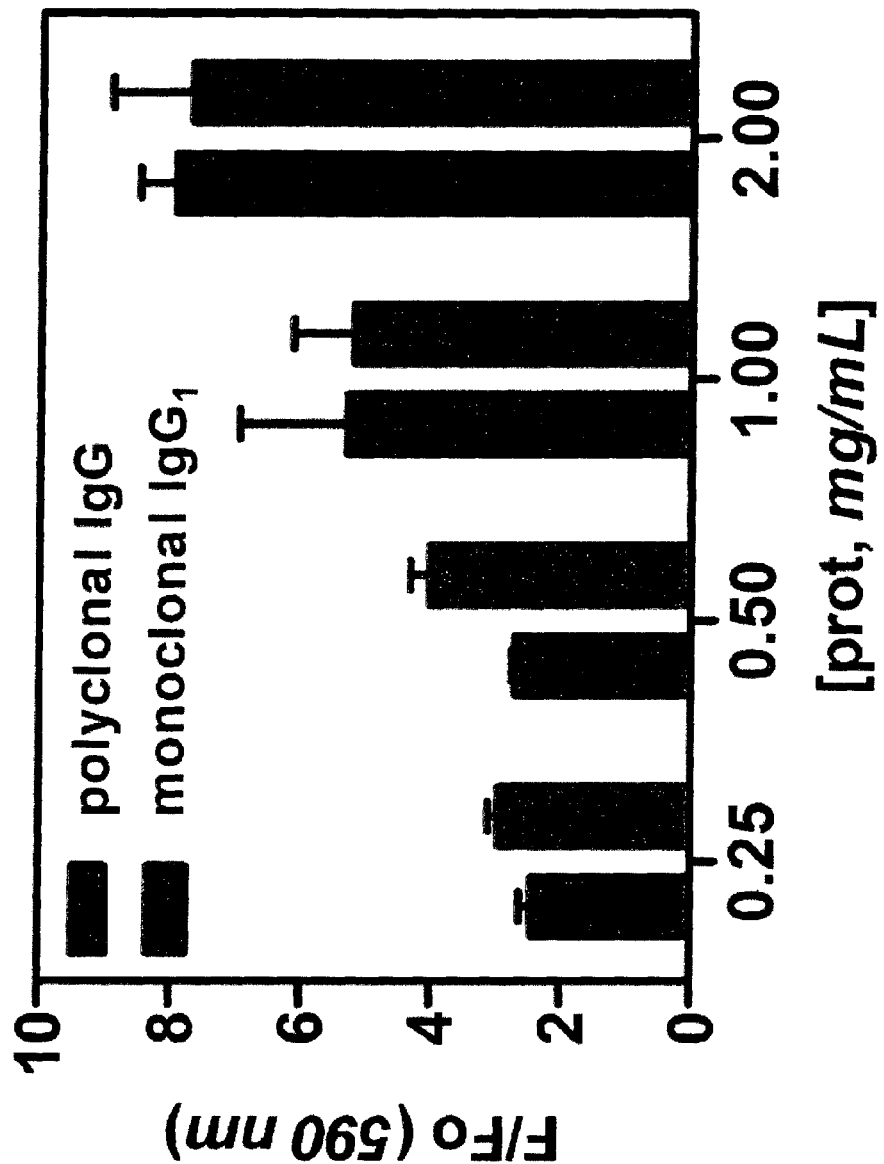
FIG. 8 shows the fluorescence intensities of Ig Orange after incubation with polyclonal human IgG and monoclonal human $IgG_1$. Values are represented as a means (n=3) and error bars as standard deviations.

Ig Orange (10 µM) was incubated with different concentrations of IgG from human serum (polyclonal IgG) and a monoclonal human IgG$_1$ in 20 mM HEPES buffer (pH 7.4). Fluorescence measurements were recorded on a SpectraMax M2 plate reader (excitation: 530 nm; emission: 590 nm) (FIG. 8).

Example 8

Fractional Saturation Curve Experiments of Ig Orange

Figure 9:
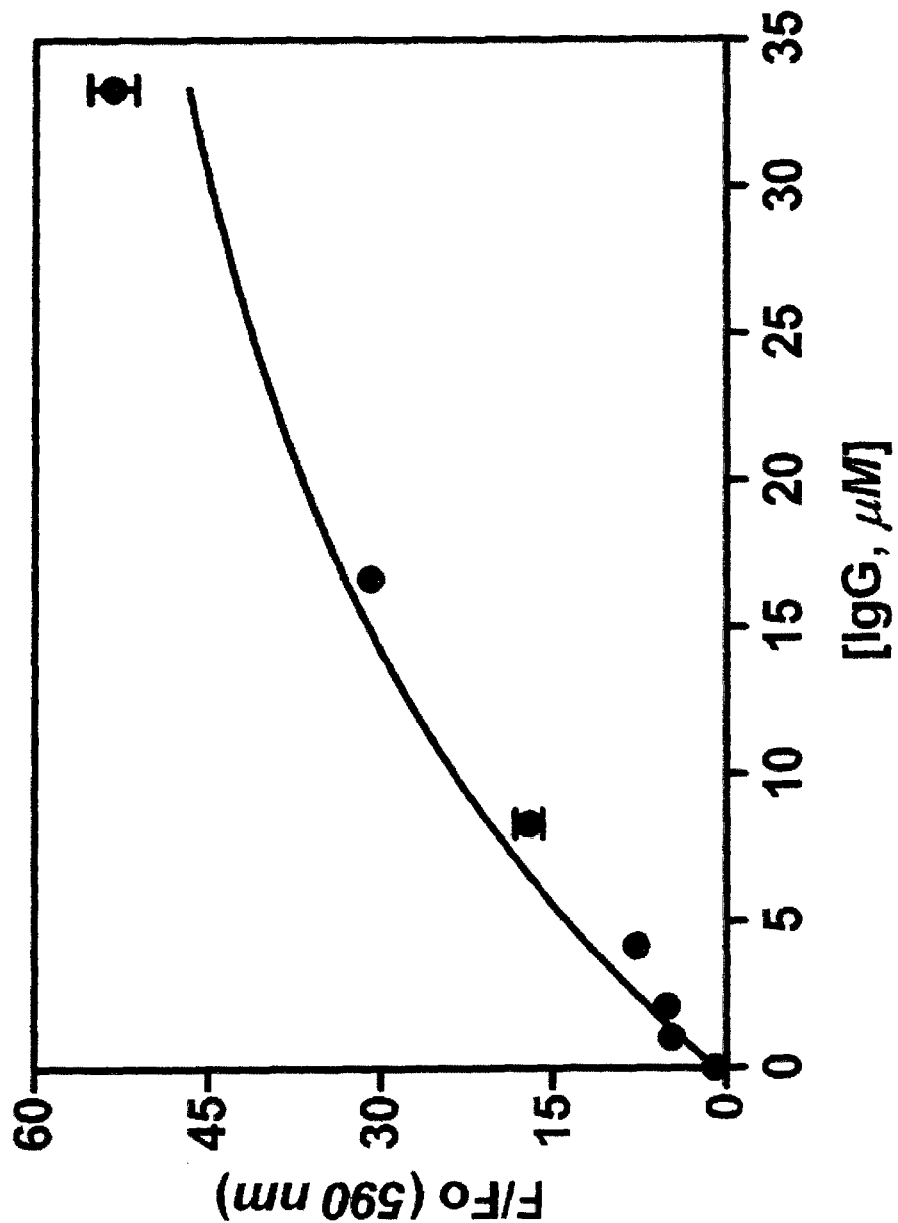
FIG. 9 shows a fluorescence-based fractional saturation curve of Ig Orange. Values were represented as means (n=3) of the fluorescence fold increase after incubation with the protein, and adjusted to a binding saturation curve (GraphPad Prism 5.0) to estimate a dissociation constant ($K_d$=14.1±0.9 µM).

Ig Orange (10 µM) was incubated with different concentrations of human IgG in 20 mM HEPES buffer (pH 7.4) and the fluorescence intensities were recorded on a SpectraMax M2 plate reader (excitation: 530 nm; emission: 590 nm) (FIG. 9).

Example 9

CDy9 Shows Specificity to mESC Versus MEF

The specificity of CDy9 to mESC was determined by high throughput screening. MEF was used as the negative control as these cells are often used as feeder cells for co-culture with mESC/iPSC. 1 uM of CDy9 was added to the mESC and MEF separately. 1× Hoechst was added to the cells to determine the nuclei staining. After 1 hour incubation, the staining pattern was visualized by image acquisition using the ImageXpress machine followed by image analysis using the MetaXpress software. To further validate and confirm the specificity of CDy9 to mESC, an intensity based analysis such as flow cytometry was carried out. Unstained mESC and MEF were used as control cells. As demonstrated by FIG. 10, CDy9 stains more specifically to mESC than MEF.

Example 10

Cell Panel Screening

Cell panel screening was performed to further confirm the specificity of CDy9. In this experiment, many different cell types from different lineages (endoderm, ectoderm, mesoderm) were tested together with mESC. After culturing the different cell types, 1 uM of CDy9 was added to the cells with 1 hour incubation. 1× Hoechst was added to the cells to determine nuclei staining. The cell staining pattern was then visualized by image acquisition using the ImageXpress machine with image analysis using the Metaxpress program. It was determined that CDy9 was highly specific to mESC when compared to all the other cell types.

Example 11

CD9 Wash-Out Experiment

Figure 12:
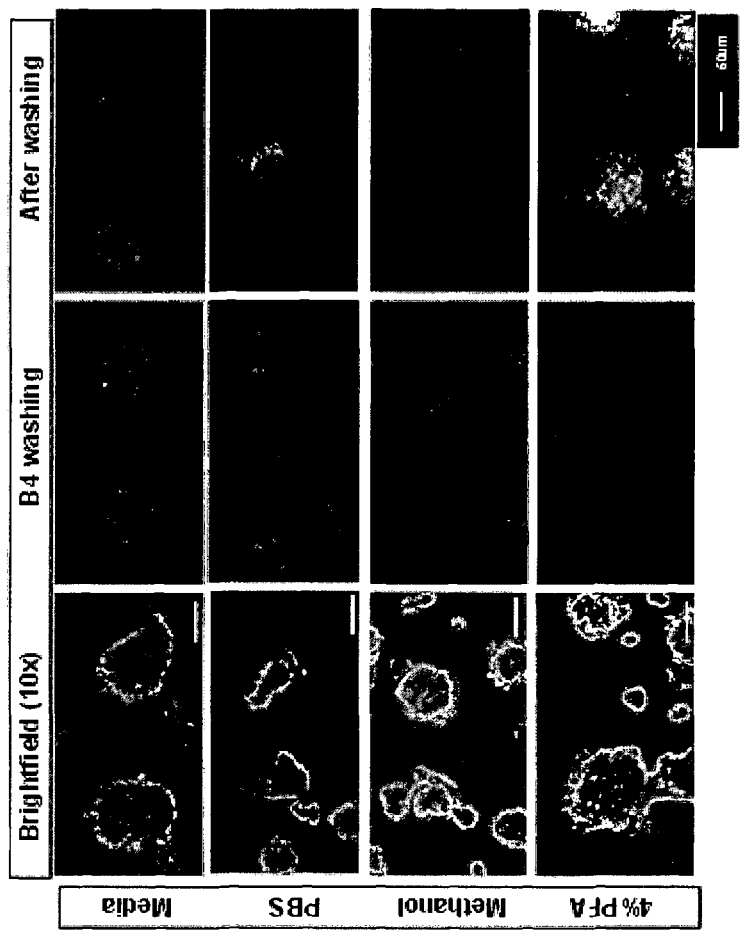
FIG. 12 shows a CDy9 wash-out experiment.

To investigate the properties of CDy9-stained mESC, a washing experiment was designed to examine survival of CDy9. 1 uM CDy9 was added to mESC. After incubation, the cells were washed with media, PBS, methanol, and 4% PFA, respectively. Utilizing the Ti microscope, 10× images were acquired. As demonstrated by FIG. 12, CDy9 was not washed out of the sample under any of the washing conditions.

Example 12

CDy9 Isolation of Stem Cells from a Mixture of MEF and mESC

Figure 13:
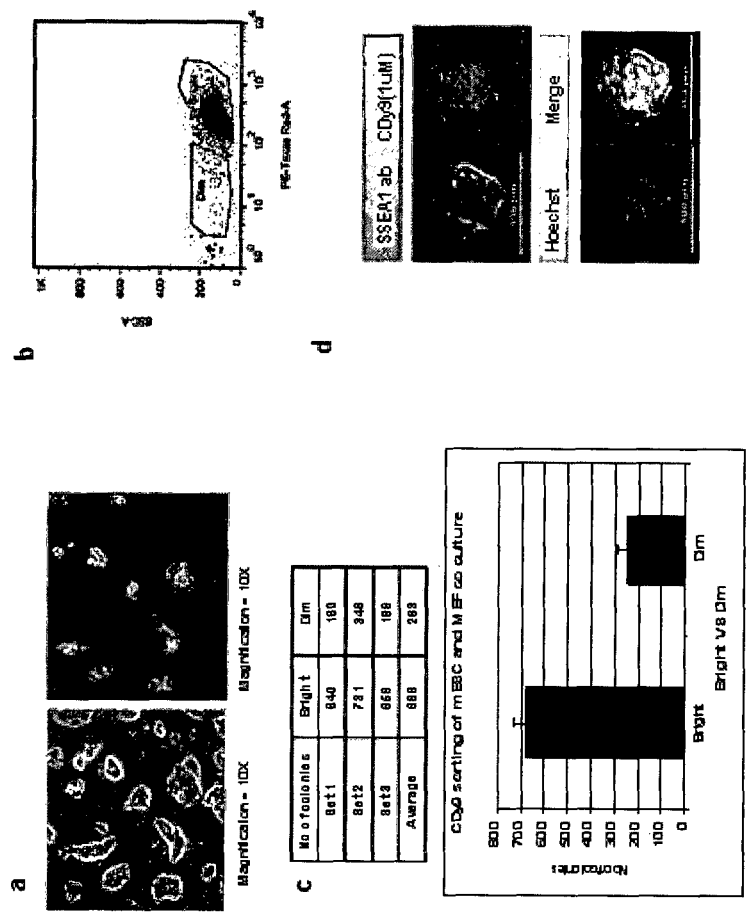
FIG. 13 shows CDy9 isolation of stem cells from a mixture of MEF and mESC.

We further examined the specificity of CDy9 when used in conjunction with a co-culture of mESC and MEF cells. 1 uM of CDy9 was added to these cells. As depicted in FIG. 13, after incubation, the cells were rinsed with PBS (3×) and prepared for FACs. During FACs analysis 10% of the brightest population and 10% of the dimmest population were sorted and collected. These cells were then seeded onto gelatin coated plates and grown for 4-5 days until mESC-like colonies started to appear. The number of colonies formed was counted and the graph was plotted after 5 days. It was noticed that the bright population formed at least 2 times more colonies than the dim population indicating that CDy9 stained mESC specifically. Immunohistochemistry was carried out on the colonies formed from the bright population. Primary antibody used was SSEA1 and secondary antibody used was AlexaFluor 488 goat anti mouse IgM.

Example 13

Isolation of Potential Pluripotent Stem Cells from Mouse Fat Pads Using CDy9

Figure 14:
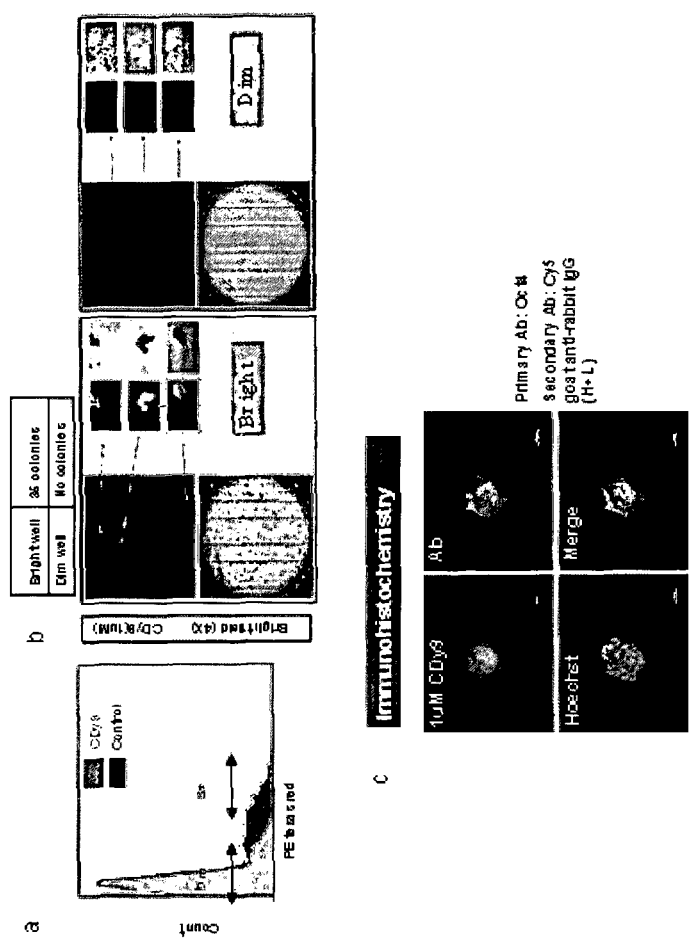
FIG. 14 shows the isolation of potential pluripotent stem cells from mouse fat pads using CDy9.

CDy9 was also utilized in the isolation of potential pluripotent stem cells from mouse fat pads using CDy9, depicted in FIG. 14. Mouse epididymal fat pads were collected and isolated into single cells using collagenase type 1. 1 uM of CDy9 was added to them and incubated for 1 hour before FACs. 10% of the dimmest and 10% of the brightest population were collected and seeded onto mitomycin treated feeder cells. After 14 days, 35 colonies were observed in the bright population compared to the dim population. 1 uM of CDy9 was added per well and 4× images of the entire wells were acquired. Right hand shows enlarged images of selected colonies. Immunohistochemistry was performed on the colonies. Primary antibody used was Oct4 while secondary antibody used was Cy5 goat anti-rabbit IgG (H+L).

DOCUMENTS CITED THROUGHOUT APPLICATION

1. A. Loudet and K. Burgess, Chem. Rev. 2007, 107, 4891.
2. G. Ulrich, R. Ziessel and A. Harriman, Angew. Chem., Int. Ed. 2008, 47, 1184.
3. G. Ulrich, R. Ziessel and A. Harriman, Angew. Chem. Int. Ed. 2007, 46, 2.
4. A. Coskun and E. U. Akkaya, J. Am. Chem. Soc. 2005, 127, 10464.
5. T. Yogo, Y. Urano, Y. Ishitsuka, F. Maniwa and T. Nagano, J. Am. Chem. Soc. 2005, 127, 12162.
6. Z. Li, E. Mintzer and R. Bittman, J. Org. Chem. 2006, 71, 1718.
7. X. Peng, J. Du, J. Fan, J. Wang, Y. Wu, J. Zhao, S. Sun and T. Xu, J. Am. Chem. Soc. 2007, 129, 1500.
8. T. Rohand, M. Baruah, W. Qin, N. Boens and W. Dehaen, Chem. Commun. 2006, 42, 266.
9. V. Leen, V. Z. Gonzalvo, W. M. Deborggraeve, N. Boens and W. Dehaen, Chem. Commun. 2010, 46, 4908.
10. W. Qin, T. Rohand, M. Baruah, A. Stefan, M. Van der Auweraer, W. Dehaen and N. Boens, Chem. Phys. Lett. 2006, 420, 562.
11. M. Kollmannsberger, K. Rurack, U. Resch-Genger and J. Daub, J. Phys. Chem. A 1998, 102, 10211.
12. K. Rurack, M. Kollmannsberger and J. Daub, Angew. Chem. Int. Ed. 2001, 40, 385.
13. C. F. Gomez-Duran, I. Garcia-Moreno, A. Costela, V. Martin, R. Sastre, J. Banuelos, F. Lopez Arbeloa, I. Lopez Arbeloa and E. Pena-Cabrera, Chem. Commun. 2010, 46, 5103.
14. J. Han, O. Gonzalez, A. Aguilar-Aguilar, E. Pena-Cabrera, and K. Burgess, Org. Biomol. Chem. 2009, 7, 34.
15. C. Thivierge, R. Bandichhor and K. Burgess, Org. Lett. 2007, 9, 2135.
16. E. Lager, J. Liu, A. Aguilar-Aguilar, B. Z. Tang and E. Pena-Cabrera, J. Org. Chem. 2009, 74, 2053.
17. V. Leen, E. Braeken, K. Luckermans, C. Jackers, M. Van der Auweraer, N. Boens and W. Dehaen, W. Chem. Commun. 2009, 45, 4515.
18. T. Rohand, W. Qin, N. Boens and W. Dehaen, Eur. J. Org. Chem. 2006, 4658.
19. H. Sunahara, Y. Urano, H. Kojima and Nagano, J. Am. Chem. Soc. 2007, 129, 5597.
20. J. S. Lee, N.Y. Kang, Y. K. Kim, A. Samanta, S. Feng, H. K. Kim, M. Vendrell, J. H. Park and Y. T. Chang, J. Am. Chem. Soc. 2009, 131, 10077.
21. J. S. Lee, H. K. Kim, S. Feng, M. Vendrell, and Y. T. Chang, Chem. Commun. 2011, 47, 2339.
22. L. D. Lavis and R. T. Raines, ACS Chem. Biol. 2008, 3, 142.
23. K. C. Nicolaou, D. A. Claremon and D. P. Papahatjis, Tetrahedron Lett. 1981, 22, 4647.
24. D. B. Ramachary and C. F. 3rd Barbas, Chemistry 2004, 10, 5323.
25. R. L. Rich and D. G. Myszka, J. Mol. Recognit. 2008, 21, 355.

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A compound represented by structural Formula (I) or pharmaceutically acceptable salts thereof:

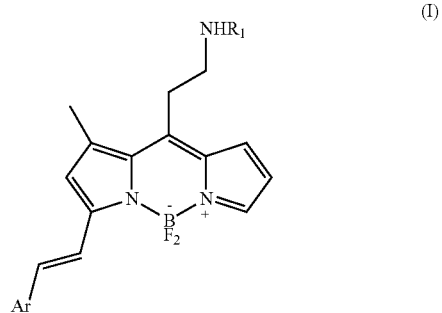

wherein:
Ar is

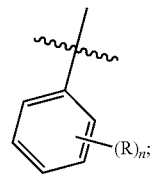

each R is independently selected from H, OH, halogen, nitro, amino, $(C_1-C_6)$alkyl, $(C=O)(C_1-C_6)$alkyl, $(C=O)H$, $(C=O)O(C_1-C_6)$alkyl, $NH(C=O)(C_1-C_6)$alkyl, $OCF_3$, $CH=CH(C_0-C_6)$alkyl aryl, $O(C_2-C_6)$alkenyl, $(C_0-C_6)$alkyl$CH=O$, $O(C_1-C_6)$alkyl, $S(C_1-C_6)$alkyl, $S(C_1-C_6)$haloalkyl, $O(C_1-C_6)$haloalkyl, $OCHF_2$, $O(C_1-C_6)$alkylamino, $(C_6-C_{10})$aryl, $(C_5-C_{10})$heteroaryl, $(C_5-C_{10})$heterocyclyl, $(C_1-C_6)$alkyl aryl, $O(C_0-C_6)$alkyl aryl, $O(CH_2)_m CHCH_2$ or 2-5-membered polycyclyl ring fused to Ar, creating a polycyclic ring system, wherein each 2-5-membered polycycle optionally and independently contains 1-2 ring heteroatoms selected from oxygen, nitrogen and sulfur;

n is 1, 2, 3 or 4;

m is 0, 1, 2, 3 or 4;

wherein, when n is 2 or greater, the R substituents may be optionally taken together to form a fused polycyclic aromatic ring system;

and wherein each R is optionally substituted with 1-4 $R_2$ substituents independently selected from:

H, $(C_1-C_6)$alkyl, halo$(C_1-C_6)$alkyl, hydroxy$(C_1-C_6)$alkyl, $(C_6-C_{10})$aryl, halo$(C_6-C_{10})$aryl, hydroxy$(C_6-C_{10})$aryl, $O(C_1-C_6)$alkyl, $O(C_1-C_6)$haloalkyl, $(C_3-C_8)$cycloalkyl, halo$(C_6-C_{10})$aryl$(C_1-C_6)$alkoxy, halogen, amino, $(C_1-C_6)$alkoxy$(C_6-C_{10})$aryl$(C_1-C_6)$alkoxy, nitro, hydroxy, $(C_0-C_6)$alkyl$(C_6-C_{10})$aryl$(C_0-C_6)$alkoxy, $(C_5-C_{10})$heterocycle, $OCF_3$, $O(C_1-C_6)$alkylamino, $(C_6-C_{10})$aryl$(C_2-C_6)$alkenyl, $(C_2-C_6)$alkenyl$(C_1-C_6)$alkoxy, $(C_1-C_6)$sulfoxy, $(C=O)O(C_1-C_6)$alkyl or $N(CH_3)(C_1-C_6)OH$;

$R_1$ is H, $C=O(C_0-C_6)$haloalkyl, $C=O(C_0-C_6)$alkyl, $C=O(C_0-C_6)$alkylene or $C=O(C_6-C_{10})$aryl.

2. The compound of claim 1, wherein:

Ar is

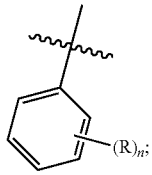

R is $CH=CH(C_0-C_6)$alkyl aryl; and n is 1.

3. The compound of claim 2, wherein:

R is $(CH=CH)$phenyl.

4. The compound of claim 2, wherein:

each $R_2$ is independently H, halogen, $(C_1-C_6)$haloalkyl or $(C_1-C_6)$alkyl.

5. The compound of claim 4, wherein the compound is represented by structural Formula (II):

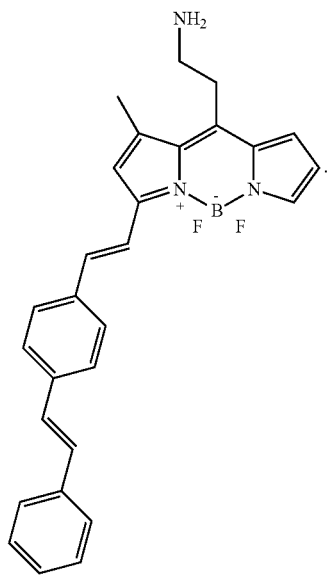

6. A method for a solid phase synthesis of a compound of structural Formula (I) or pharmaceutically acceptable salts thereof:

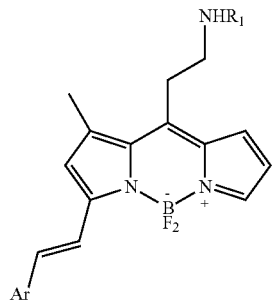

wherein:

Ar is

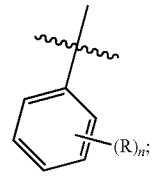

each R is independently selected from H, OH, halogen, nitro, amino, $(C_1-C_6)$alkyl, $(C=O)(C_1-C_6)$alkyl, $(C=O)H$, $(C=O)O(C_1-C_6)$alkyl, $NH(C=O)(C_1-C_6)$alkyl, $OCF_3$, $CH=CH(C_0-C_6)$alkylaryl, $O(C_2-C_6)$alkenyl, $(C_0-C_6)$alkylCH=O, $O(C_1-C_6)$alkyl, $S(C_1-C_6)$alkyl, $S(C_1-C_6)$haloalkyl, $O(C_1-C_6)$haloalkyl, $OCHF_2$, $O(C_1-C_6)$alkylamino $(C_6-C_{10})$aryl, $(C_5-C_{10})$heteroaryl, $(C_5-C_{10})$heterocyclyl, $(C_1-C_6)$alkyl aryl, $O(C_0-C_6)$alkyl aryl, $O(CH_2)_m CHCH_2$ or 2-5-membered polycyclyl ring fused to Ar, creating a polycyclic ring system, wherein each 2-5-membered polycycle optionally and independently contains 1-2 ring heteroatoms selected from oxygen, nitrogen and sulfur;

n is 1, 2, 3 or 4;

m is 0, 1, 2, 3 or 4;

wherein, when n is 2 or greater, the R substituents may be optionally taken together to form a fused polycyclic aromatic ring system;

and wherein each R is optionally substituted with 1-4 $R_2$ substituents independently selected from:

H, $(C_1-C_6)$alkyl, halo$(C_1-C_6)$alkyl, hydroxy$(C_1-C_6)$alkyl, $(C_6-C_{10})$aryl, halo$(C_6-C_{10})$aryl, hydroxy$(C_6-C_{10})$aryl, $O(C_1-C_6)$alkyl, $O(C_1-C_6)$haloalkyl, $(C_3-C_8)$cycloalkyl, halo$(C_6-C_{10})$aryl$(C_1-C_6)$alkoxy, halogen, amino, $(C_1-C_6)$alkoxy$(C_6-C_{10})$aryl$(C_1-C_6)$alkoxy, nitro, hydroxy, $(C_0-C_6)$alkyl$(C_6-C_{10})$aryl$(C_0-C_6)$alkoxy, $(C_5-C_{10})$heterocycle, $OCF_3$, $O(C_1-C_6)$alkylamino, $(C_6-C_{10})$aryl$(C_2-C_6)$alkenyl, $(C_2-C_6)$alkenyl$(C_1-C_6)$alkoxy, $(C_1-C_6)$sulfoxy, $(C=O)O(C_1-C_6)$alkyl or $N(CH_3)(C_1-C_6)OH$;

$R_1$ is H, $C=O(C_0-C_6)$haloalkyl, $C=O(C_0-C_6)$alkyl, $C=O(C_0-C_6)$alkylene or $C=O(C_6-C_{10})$aryl;

comprising the steps of:

a) reacting an Fmoc-protected amino acid and pyrrole to prepare 2-ketopyrrole (a derivative 1):

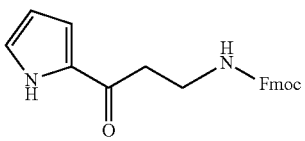

1 b) condensing derivative 1 with 2,4-dimethylpyrrole and an activating agent, and adding $BF_3 \cdot OEt_2$ in situ to obtain derivative 2:

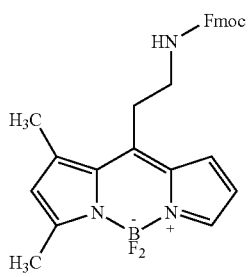

2 c) reacting derivative 2 with a base;
d) quenching the reaction mixture of step c) with an aqueous HCl to produce derivative 3:

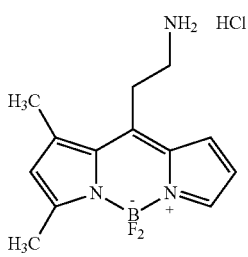

3 e) loading derivative 3 on 2-chlorotrityl chloride polystyrene resin to produce a loaded resin; and
f) reacting the loaded resin from step e) with an aldehyde to produce the compound of Formula I, and subsequently extracting the compound of Formula I from step e) by a solid-phase extraction.

7. The method of claim 6, wherein:
Ar is

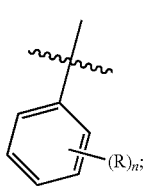

R is CH=CH($C_0$-$C_6$)alkyl aryl; and
n is 1.

8. The method of claim 7, wherein the compound is represented by structural Formula (II):

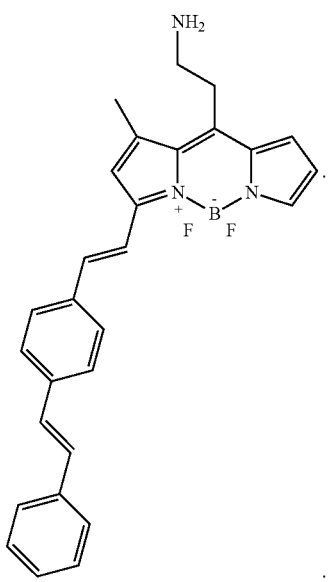

(II)

9. A method for visually detecting immunoglobulins in a sample, comprising:
   a) incubating the immunoglobulins with the compound of claim 1 under conditions sufficient to form an incubated mixture; and
   b) exposing the incubated mixture to a wavelength of light sufficient to visualize the immunoglobulins using fluorescence spectroscopy.

10. The compound of claim 1, wherein the compound is represented by the structural Formula (IV)

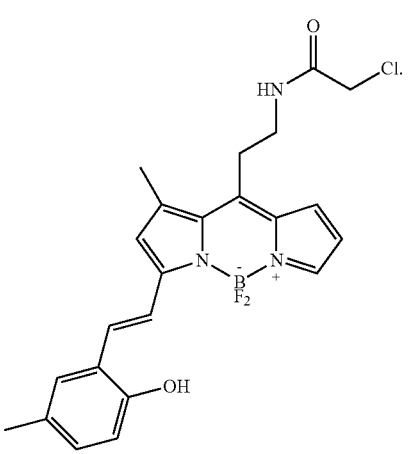

(IV)

11. A method for staining stem cells, comprising:
   a) incubating the stem cells with the compound of claim 1 under conditions sufficient to form an incubated mixture; and
   b) exposing the incubated mixture to a wavelength of light sufficient to visualize the stem cells using fluorescence spectroscopy.

* * * * *